United States Patent
Lopez-Ulibarri et al.

(10) Patent No.: US 12,133,542 B2
(45) Date of Patent: Nov. 5, 2024

(54) ANIMAL FEED COMPOSITIONS AND USES THEREOF

(71) Applicants: Novozymes A/S, Bagsvaerd (DK); DSM IP Assets B.V., Heerlen (NL)

(72) Inventors: Rual Lopez-Ulibarri, Kaiseraugst (CH); Estefania Perez Calvo, Kaiseraugst (CH); Wolfgang Schliffka, Kaiseraugst (CH)

(73) Assignees: Novozymes A/S, Bagsvaerd (DK); DSM IP Assets B.V., Heerlen (NL)

( * ) Notice: Subject to any disclaimer, the term of this patent is extended or adjusted under 35 U.S.C. 154(b) by 976 days.

(21) Appl. No.: 17/047,771

(22) PCT Filed: Apr. 25, 2019

(86) PCT No.: PCT/EP2019/060635
§ 371 (c)(1),
(2) Date: Oct. 15, 2020

(87) PCT Pub. No.: WO2019/207053
PCT Pub. Date: Oct. 31, 2019

(65) Prior Publication Data
US 2021/0112827 A1    Apr. 22, 2021

(30) Foreign Application Priority Data

Apr. 25, 2018  (EP) .................................... 18169185

(51) Int. Cl.
| | |
|---|---|
| A23K 20/147 | (2016.01) |
| A23K 10/18 | (2016.01) |
| A23K 10/30 | (2016.01) |
| A23K 20/174 | (2016.01) |
| A23K 20/189 | (2016.01) |
| A23K 50/30 | (2016.01) |
| A23K 50/75 | (2016.01) |
| C12N 9/36 | (2006.01) |

(52) U.S. Cl.
CPC ............ *A23K 20/147* (2016.05); *A23K 10/18* (2016.05); *A23K 10/30* (2016.05); *A23K 20/174* (2016.05); *A23K 20/189* (2016.05); *A23K 50/30* (2016.05); *A23K 50/75* (2016.05); *C12N 9/2462* (2013.01); *C12Y 302/01017* (2013.01)

(58) Field of Classification Search
CPC ................ A23K 20/147; A23K 20/174; A23K 20/198; A23K 50/30; A23K 50/75; A23K 10/18; A23K 10/30; C12N 9/2462; C12Y 302/01017
See application file for complete search history.

(56) References Cited

U.S. PATENT DOCUMENTS

| | | | |
|---|---|---|---|
| 6,221,404 B1 * | 4/2001 | Nguyen ............... | A23K 20/189 426/807 |
| 2016/0030528 A1 * | 2/2016 | Metcalf ................... | C12N 9/24 435/352 |

FOREIGN PATENT DOCUMENTS

| | | |
|---|---|---|
| CN | 103750052 A | 4/2014 |
| WO | 2011/075138 A1 | 6/2011 |
| WO | 2017/001703 A1 | 1/2017 |
| WO | 2017/064092 A1 | 4/2017 |
| WO | 2017/202979 A1 | 11/2017 |

OTHER PUBLICATIONS

Adeola et al., J. Anim. Sci., vol. 89, pp. 3189-3218 (2011).
Santos et al., Animal Nutrition, vol. 3, pp. 121-126 (2017).

* cited by examiner

*Primary Examiner* — Donald R Spamer
*Assistant Examiner* — Assaf Zilbering
(74) *Attorney, Agent, or Firm* — Adam Rucker

(57) ABSTRACT

The present invention relates to animal feed compositions comprising at least one probiotic and polypeptides having muramidase activity.

19 Claims, No Drawings

Specification includes a Sequence Listing.

ANIMAL FEED COMPOSITIONS AND USES THEREOF

CROSS-REFERENCE TO RELATED APPLICATIONS

This application is a 35 U.S.C. 371 national application of international application no. PCT/EP2019/060635 filed Apr. 25, 2019, which claims priority or the benefit under 35 U.S.C. 119 of European application no. EP 18169185.8 filed Apr. 25, 2018. The content of these applications is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to animal feed compositions comprising polypeptides having muramidase activity and probiotics and uses thereof.

Description of the Related Art

Muramidase is an O-glycosyl hydrolase produced as a defensive mechanism against bacteria by many organisms. The enzyme causes the hydrolysis of bacterial cell walls by cleaving the glycosidic bonds of peptidoglycan; an important structural molecule in bacteria. After having their cell walls weakened by muramidase action, bacterial cells lyse as a result of umbalanced osmotic pressure.

Muramidase naturally occurs in many organisms such as viruses, plants, insects, birds, reptiles and mammals. In mammals, Muramidase has been isolated from nasal secretions, saliva, tears, intestinal content, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide of many microorganisms.

Muramidase has been classified into five different glycoside hydrolase (GH) families (CAZy, www.cazy.org): hen egg-white lysozyme (GH22), goose egg-white lysozyme (GH23), bacteriophage T4 muramidase (GH24), *Sphingomonas flagellar* protein (GH73) and *Chalaropsis muramidases* (GH25). Lysozyme extracted from hen egg white (a GH22 muramidase) is the primary product available on the commercial market, and traditionally has just been referred to as a lysozyme even though nowadays there are many other known lysozymes.

Probiotics are live micro-organisms that when administered in adequate amounts, are associated with a health benefit on the host. Probiotics may defend against pathogens in the intestine to provide health benefits. Probiotics may compete against pathogens for the same essential nutrients, leaving less available for the pathogen to utilize. Alternatively, they may bind to adhesion sites, preventing pathogen attachment by reducing the surface area available for pathogen colonization. A postulated mechanism includes signaling of immune cells by probiotics may result in the secretion of cytokines, targeting the pathogen for destruction. Finally, some have proposed probiotics may attack pathogenic organisms by releasing bacteriocins, killing them directly.

It has been shown in WO 2017/001703 that microbial muramidases improve animal performance. However, combining different types of enzymes often doesn't result in any beneficial results over the single enzyme, see T. T. dos Santos et al., "Protease, protease and superdosing phytase interactions in broiler performance, carcass yield and digesta transit time", Animal Nutrition (2017), 3, 121-126 and Adeola and Cowieson, "Opportunities and challenges in using exogenous enzymes to improve nonruminant animal production", *J Anim Sci*, (2011), 89, 189-3218.

Improving the growth performance of farm animals is needed in a world with a growing population eating more animal protein, and it is the object of the present invention to devise solutions which helps meet this challenge.

SUMMARY OF THE INVENTION

The inventors of the present application surprisingly found that the combination of polypeptides having muramidase activity and at least one probiotic have a great potential for use in animal nutrition, e.g. for improving the feed conversion ratio (FCR) and/or weight gain and/or for the modulation of the gut flora and/or for improving bioavailability of probiotics. Further, the inventors surprisingly found that the novel feed compositions have also activity against Gram+ microorganisms resulting in a reduced mortality.

The present invention relates to a composition, animal feed additive or animal feed comprising one or more polypeptides having muramidase activity and at least one probiotic. The present invention is furthermore directed to animal feed comprising an animal feed additive, one or more protein sources and one or more energy sources characterised in the animal feed further comprises one or more probiotic and one or more fungal polypeptides having muramidase activity.

The present invention further relates to a method of improving one or more performance parameters in an animal comprising administering to one or more animals an animal feed or animal feed additive comprising at least one probiotic and one or more polypeptides having muramidase activity, wherein the one or more performance parameters is selected from the group consisting of the European Production Efficiency Factor (EPEF) and Feed Conversion Ratio (FCR).

The present invention further relates to methods of improving the European Production Efficiency Factor (EPEF) and/or Feed Conversion Ratio (FCR) of an animal comprising administering to the animal the animal feed or the animal feed additive of the invention; use of the animal feed or animal feed additive of the invention for improving the European Production Efficiency Factor (EPEF) and/or Feed Conversion Ration (FCR); an animal feed or animal feed additive of the invention for use in the treatment of a *Clostridium perfringens* infection; and a method of increasing the population of bacteria of the genus *Faecalibacterium* in the microbiota of the GI tract of an animal, comprising administering to the animal an animal feed or animal feed additive of the invention.

A further aspect of the invention is directed to a method of improving European production efficiency factor (EPEF), body weight gain (BWG) and/or feed conversion ratio (FCR) of a mono-gastric animal comprising:
  (a) preparing the animal feed comprising an animal feed additive, one or more protein sources and one or more energy sources characterised in the animal feed further comprises one or more probiotic and one or more fungal polypeptides having muramidase activity; and (b) providing the animal feed to the mono-gastric animal.

The invention is directed to a use of at least one probiotic in combination with a polypeptide having muramidase activity in a feed composition for improving feed conversion ratio and/or daily weight gain and/or for the modulation of the gut flora and/or for improving bioavailability of the probiotic, wherein the polypeptide having muramidase activity is a fungal GH24 muramidase or GH25 muramidase and wherein the probiotic is selected from the group consisting of a *Lactobacillus*, a *Bifidobacterium*, a *Saccharomyces*, an *Enterococcus*, a *Streptococcus*, a *Pediococcus*, a *Leuconostoc*, a *Lactococcus*, an *Oenococcus*, a *Bacillus*, *Carnobacterium*, *Propionibacterium*, *Clostridium*, *Megasphaera* and an *Escherichia* or combinations thereof.

A further aspect of the invention is directed to a feed composition or a premix composition, or a feed additive for animals comprising at least one polypeptide having muramidase activity and at least one probiotic, wherein the polypeptide having muramidase activity is a fungal GH24 muramidase or GH25 muramidase and wherein the probiotic is selected from the group consisting of a *Lactobacillus*, a *Bifidobacterium*, a *Saccharomyces*, an *Enterococcus*, a *Streptococcus*, a *Pediococcus*, a *Leuconostoc*, a *Lactococcus*, an *Oenococcus*, a *Bacillus*, *Carnobacterium*, *Propionibacterium*, *Clostridium*, *Megasphaera* and an *Escherichia* or combinations thereof.

OVERVIEW OF SEQUENCE LISTING

SEQ ID NO: 1 is the mature amino acid sequence of a GH25 muramidase from *Acremonium alcalophilum* as described in WO2013/076253 (SEQ ID NO: 4)

SEQ ID NO: 2 is the mature amino acid sequence of a GH25 muramidase from 35 *Acremonium alcalophilum* as described in WO2013/076253 (SEQ ID NO: 8).

SEQ ID NO: 3 is the mature amino acid sequence of a GH25 muramidase from *Aspergillus fumigatus* as described in WO2011/104339 (SEQ ID NO: 3).

SEQ ID NO: 4 is the mature amino acid sequence of a GH25 muramidase from *Trichoderma reesei* as described in WO2009/102755 (SEQ ID NO: 4).

SEQ ID NO: 5 is the mature amino acid sequence of a GH25 muramidase from *Trametes cinnabarina* as described in WO2005/080559 (SEQ ID NO: 2).

SEQ ID NO: 6 is the mature amino acid sequence of a GH25 muramidase from *Sporormia fimetaria* as described in PCT/CN2017/075978 (SEQ ID NO: 3).

SEQ ID NO: 7 is the mature amino acid sequence of a GH25 muramidase from *Poronia punctata* as described in PCT/CN2017/075978 (SEQ ID NO: 6).

SEQ ID NO: 8 is the mature amino acid sequence of a GH25 muramidase from *Poronia punctata* as described in PCT/CN2017/075978 (SEQ ID NO: 9).

SEQ ID NO: 9 is the mature amino acid sequence of a GH25 muramidase from *Lecanicillium* sp. WMM742 as described in PCT/CN2017/075978 (SEQ ID NO: 12).

SEQ ID NO: 10 is the mature amino acid sequence of a GH25 muramidase from *Lecanicillium* sp. WMM742 as described in PCT/CN2017/075978 (SEQ ID NO: 15).

SEQ ID NO: 11 is the mature amino acid sequence of a GH25 muramidase from *Onygena equina* as described in PCT/CN2017/075978 (SEQ ID NO: 18).

SEQ ID NO: 12 is the mature amino acid sequence of a GH25 muramidase from *Purpureocillium lilacinum* as described in PCT/CN2017/075978 (SEQ ID NO: 21).

SEQ ID NO: 13 is the mature amino acid sequence of a GH25 muramidase from *Trichobolus zukalii* as described in PCT/CN2017/075978 (SEQ ID NO: 24).

SEQ ID NO: 14 is the mature amino acid sequence of a GH25 muramidase from *Penicillium citrinum* as described in PCT/CN2017/075978 (SEQ ID NO: 27).

SEQ ID NO: 15 is the mature amino acid sequence of a GH25 muramidase from *Cladorrhinum bulbilosum* as described in PCT/CN2017/075978 (SEQ ID NO: 30).

SEQ ID NO: 16 is the mature amino acid sequence of a GH25 muramidase from *Umbelopsis westeae* as described in PCT/CN2017/075978 (SEQ ID NO: 33).

SEQ ID NO: 17 is the mature amino acid sequence of a GH25 muramidase from *Zygomycetes* sp. XZ2655 as described in PCT/CN2017/075978 (SEQ ID NO: 36).

SEQ ID NO: 18 is the mature amino acid sequence of a GH25 muramidase from 30 *Chaetomium cupreum* as described in PCT/CN2017/075978 (SEQ ID NO: 39).

SEQ ID NO: 19 is the mature amino acid sequence of a GH25 muramidase from *Cordyceps cardinalis* as described in PCT/CN2017/075978 (SEQ ID NO: 42).

SEQ ID NO: 20 is the mature amino acid sequence of a GH25 muramidase from *Penicillium* sp. 'qii' as described in PCT/CN2017/075978 (SEQ ID NO: 45).

SEQ ID NO: 21 is the mature amino acid sequence of a GH25 muramidase from *Aspergillus* sp. novXZ2609 as described in PCT/CN2017/075978 (SEQ ID NO: 48).

SEQ ID NO: 22 is the mature amino acid sequence of a GH25 muramidase from *Paecilomyces* sp. XZ2658 as described in PCT/CN2017/075978 (SEQ ID NO: 51).

SEQ ID NO: 23 is the mature amino acid sequence of a GH25 muramidase from *Paecilomyces* sp. XZ2658 as described in PCT/CN2017/075978 (SEQ ID NO: 54).

SEQ ID NO: 24 is the mature amino acid sequence of a GH25 muramidase from *Pycnidiophora cf dispera* as described in PCT/CN2017/075978 (SEQ ID NO: 60).

SEQ ID NO: 25 is the mature amino acid sequence of a GH25 muramidase from *Thermomucor indicae-seudaticae* as described in PCT/CN2017/075978 (SEQ ID NO: 63).

SEQ ID NO: 26 is the mature amino acid sequence of a GH25 muramidase from *Isaria farinosa* as described in PCT/CN2017/075978 (SEQ ID NO: 66).

SEQ ID NO: 27 is the mature amino acid sequence of a GH25 muramidase from *Lecanicillium* sp. WMM742 as described in PCT/CN2017/075978 (SEQ ID NO: 69).

SEQ ID NO: 28 is the mature amino acid sequence of a GH25 muramidase from *Zopfiella* sp. t180-6 as described in PCT/CN2017/075978 (SEQ ID NO: 72).

SEQ ID NO: 29 is the mature amino acid sequence of a GH25 muramidase from *Malbranchea flava* as described in PCT/CN2017/075978 (SEQ ID NO: 75).

SEQ ID NO: 30 is the mature amino acid sequence of a GH25 muramidase from *Hypholoma polytrichi* as described in PCT/CN2017/075978 (SEQ ID NO: 80).

SEQ ID NO: 31 is the mature amino acid sequence of a GH25 muramidase from *Aspergillus deflectus* as described in PCT/CN2017/075978 (SEQ ID NO: 83).

SEQ ID NO: 32 is the mature amino acid sequence of a GH25 muramidase from *Ascobolus stictoideus* as described in PCT/CN2017/075978 (SEQ ID NO: 86).

SEQ ID NO: 33 is the mature amino acid sequence of a GH25 muramidase from *Coniochaeta* sp. as described in PCT/CN2017/075978 (SEQ ID NO: 89).

SEQ ID NO: 34 is the mature amino acid sequence of a GH25 muramidase from *Daldinia fissa* as described in PCT/CN2017/075978 (SEQ ID NO: 92).

SEQ ID NO: 35 is the mature amino acid sequence of a GH25 muramidase from *Rosellinia* sp. as described in PCT/CN2017/075978 (SEQ ID NO: 95).

SEQ ID NO: 36 is the mature amino acid sequence of a GH25 muramidase from *Ascobolus* sp. ZY179 as described in PCT/CN2017/075978 (SEQ ID NO: 98).

SEQ ID NO: 37 is the mature amino acid sequence of a GH25 muramidase from *Curreya* sp. XZ2623 as described in PCT/CN2017/075978 (SEQ ID NO: 101).

SEQ ID NO: 38 is the mature amino acid sequence of a GH25 muramidase from *Coniothyrium* sp. as described in PCT/CN2017/075978 (SEQ ID NO: 104).

SEQ ID NO: 39 is the mature amino acid sequence of a GH25 muramidase from *Hypoxylon* sp. as described in PCT/CN2017/075978 (SEQ ID NO: 107).

SEQ ID NO: 40 is the mature amino acid sequence of a GH25 muramidase from *Xylariaceae* sp. 1653h as described in PCT/CN2017/075978 (SEQ ID NO: 110).

SEQ ID NO: 41 is the mature amino acid sequence of a GH25 muramidase from *Hypoxylon* sp. as described in PCT/CN2017/075978 (SEQ ID NO: 113).

SEQ ID NO: 42 is the mature amino acid sequence of a GH25 muramidase from *Yunnania penicillata* as described in PCT/CN2017/075978 (SEQ ID NO: 116).

SEQ ID NO: 43 is the mature amino acid sequence of a GH25 muramidase from *Engyodontium album* as described in PCT/CN2017/075978 (SEQ ID NO: 119).

SEQ ID NO: 44 is the mature amino acid sequence of a GH25 muramidase from *Metapochonia bulbillosa* as described in PCT/CN2017/075978 (SEQ ID NO: 122).

SEQ ID NO: 45 is the mature amino acid sequence of a GH25 muramidase from *Hamigera paravellanea* as described in PCT/CN2017/075978 (SEQ ID NO: 125).

SEQ ID NO: 46 is the mature amino acid sequence of a GH25 muramidase from *Metarhizium iadini* as described in PCT/CN2017/075978 (SEQ ID NO: 128).

SEQ ID NO: 47 is the mature amino acid sequence of a GH25 muramidase from *Thermoascus aurantiacus* as described in PCT/CN2017/075978 (SEQ ID NO: 131).

SEQ ID NO: 48 is the mature amino acid sequence of a GH25 muramidase from *Clonostachys rossmaniae* as described in PCT/CN2017/075978 (SEQ ID NO: 134).

SEQ ID NO: 49 is the mature amino acid sequence of a GH25 muramidase from *Simplicillium obclavatum* as described in PCT/CN2017/075978 (SEQ ID NO: 137).

SEQ ID NO: 50 is the mature amino acid sequence of a GH25 muramidase from *Aspergillus inflatus* as described in PCT/CN2017/075978 (SEQ ID NO: 140).

SEQ ID NO: 51 is the mature amino acid sequence of a GH25 muramidase from *Paracremonium inflatum* as described in PCT/CN2017/075978 (SEQ ID NO: 143).

SEQ ID NO: 52 is the mature amino acid sequence of a GH25 muramidase from *Westerdykella* sp. as described in PCT/CN2017/075978 (SEQ ID NO: 146).

SEQ ID NO: 53 is the mature amino acid sequence of a GH25 muramidase from *Stropharia semiglobata* as described in PCT/CN2017/075978 (SEQ ID NO: 155).

SEQ ID NO: 54 is the mature amino acid sequence of a GH25 muramidase from *Gelasinospora cratophora* as described in PCT/CN2017/075978 (SEQ ID NO: 158).

SEQ ID NO: 55 is the mature amino acid sequence of a GH25 muramidase from *Flammulina velutipes* as described in PCT/CN2017/075978 (SEQ ID NO: 221).

SEQ ID NO: 56 is the mature amino acid sequence of a GH25 muramidase from *Deconica coprophila* as described in PCT/CN2017/075978 (SEQ ID NO: 224).

SEQ ID NO: 57 is the mature amino acid sequence of a GH25 muramidase from *Rhizomucor pusillus* as described in PCT/CN2017/075978 (SEQ ID NO: 227).

SEQ ID NO: 58 is the mature amino acid sequence of a GH25 muramidase from *Stropharia semiglobata* as described in PCT/CN2017/075978 (SEQ ID NO: 230).

SEQ ID NO: 59 is the mature amino acid sequence of a GH25 muramidase from *Stropharia semiglobata* as described in PCT/CN2017/075978 (SEQ ID NO: 233).

SEQ ID NO: 60 is the mature amino acid sequence of a GH25 muramidase from *Myceliophthora fergusii* as described in PCT/CN2017/075960 (SEQ ID NO: 3).

SEQ ID NO: 61 is the mature amino acid sequence of a GH25 muramidase from *Mortierella alpina* as described in PCT/CN2017/075960 (SEQ ID NO: 15).

SEQ ID NO: 62 is the mature amino acid sequence of a GH25 muramidase from *Penicillium atrovenetum* as described in PCT/CN2017/075960 (SEQ ID NO: 27).

SEQ ID NO: 63 is the mature amino acid sequence of a GH24 muramidase from *Trichophaea saccata* as described in WO2017/000922 (SEQ ID NO: 257).

SEQ ID NO: 64 is the mature amino acid sequence of a GH24 muramidase from *Chaetomium thermophilum* as described in WO2017/000922 (SEQ ID NO: 264).

SEQ ID NO: 65 is the mature amino acid sequence of a GH24 muramidase from *Trichoderma harzianum* as described in WO2017/000922 (SEQ ID NO: 267).

SEQ ID NO: 66 is the mature amino acid sequence of a GH24 muramidase from *Trichophaea minuta* as described in WO2017/000922 (SEQ ID NO: 291).

SEQ ID NO: 67 is the mature amino acid sequence of a GH24 muramidase from *Chaetomium* sp. ZY287 as described in WO2017/000922 (SEQ ID NO: 294).

SEQ ID NO: 68 is the mature amino acid sequence of a GH24 muramidase from *Mortierella* sp. ZY002 as described in WO2017/000922 (SEQ ID NO: 297).

SEQ ID NO: 69 is the mature amino acid sequence of a GH24 muramidase from *Metarhizium* sp. XZ2431 as described in WO2017/000922 (SEQ ID NO: 300).

SEQ ID NO: 70 is the mature amino acid sequence of a GH24 muramidase from *Geomyces auratus* as described in WO2017/000922 (SEQ ID NO: 303).

SEQ ID NO: 71 is the mature amino acid sequence of a GH24 muramidase from *Ilyonectria rufa* as described in WO2017/000922 (SEQ ID NO: 306).

Definitions

Animal: The term "animal" refers to any animal except humans. Examples of animals are monogastric animals, including but not limited to pigs or swine (including, but not limited to, piglets, growing pigs, and sows); poultry such as turkeys, ducks, quail, guinea fowl, geese, pigeons (including squabs) and chicken (including but not limited to broiler chickens (referred to herein as broiles), chicks, layer hens (referred to herein as layers)); horses (including but not limited to hotbloods, coldbloods and warm bloods) crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish).

Animal feed: The term "animal feed" refers to any compound, preparation, or mixture suitable for, or intended for intake by an animal. Animal feed for a monogastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Body Weight Gain: The term "body weight gain" means an increase in live weight of an animal during a given period of time e.g. the increase in weight from day 1 to day 21.

Concentrates: The term "concentrates" means feed with high protein and energy concentrations, such as fish meal, molasses, oligosaccharides, sorghum, seeds and grains (eitherwhole or prepared by crushing, milling, etc. from e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

European Production Efficiency Factor (EPEF): The European Production Efficiency Factor is a way of comparing the performance of animals. This single-figure facilitates comparison of performance within and among farms and can be used to assess environmental, climatic and animal management variables. The EPEF is calculated as [(liveability (%)×Liveweight (kg))/(Age at depletion (days)×FCR)]× 100, wherein livability is the percentage of animals alive at slaughter, Liveweight is the average weight of the animals at slaughter, age of depletion is the age of the animals at slaughter and FCR is the feed conversion ratio at slaughter.

Feed Conversion Ratio (FCR): FCR is a measure of an animal's efficiency in converting feed mass into increases of the desired output. Animals raised for meat—such as swine, poultry and fish—the output is the mass gained by the animal. Specifically FCR is calculated as feed intake divided by weight gain, all over a specified period. Improvement in FCR means reduction of the FCR value. A FCR improvement of 2% means that the FCR was reduced by 2%.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, brassica (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Fragment: The term "fragment" means a polypeptide or a catalytic domain having one or more (e.g., several) amino acids absent from the amino and/or carboxyl terminus of a mature polypeptide or domain; wherein the fragment has muramidase activity.

In one aspect, a fragment of a GH24 muramidase (such as one of SEQ ID NO: 63 to 71) comprises at least 230 amino acids, such as at least 235 amino acids, at least 240 amino acids, or at least 245 amino acids and has muramidase activity. In another aspect, a fragment of a GH24 muramidase (such as one of SEQ ID NO: 63 to 71) comprises at least 90% of the length of the mature polypeptide, such as at least 92%, at least 94%, at least 96%, at least 98% or at least 99% of the length of the mature polypeptide and has muramidase activity.

In one aspect, a fragment of a GH25 muramidase (such as one of SEQ ID NO: 1 to 72) comprises at least 180 amino acids, such as at least 185 amino acids, at least 190 amino acids, at least 195 amino acids, at least 200 amino acids, at least 205 amino acids or at least 210 amino acids and has muramidase activity. In another aspect, a fragment of a GH25 muramidase (such as one of SEQ ID NO: 1 to 72) comprises at least 90% of the length of the mature polypeptide, such as at least 92%, at least 94%, at least 96%, at least 98% or at least 99% of the length of the mature polypeptide and has muramidase activity.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Muramidase activity: The term "muramidase activity" means the enzymatic hydrolysis of the 1,4-beta-linkages between N-acetylmuramic acid and N-acetyl-D-glucosamine residues in a peptidoglycan or between N-acetyl-D-glucosamine residues in chitodextrins, resulting in bacteriolysis due to osmotic pressure. Muramidase belongs to the enzyme class EC 3.2.1.17. Muramidase activity is typically measured by turbidimetric determination. The method is based on the changes in turbidity of a suspension of *Micrococcus luteus* ATCC 4698 induced by the lytic action of muramidase. In appropriate experimental conditions these changes are proportional to the amount of muramidase in the medium (c.f. INS 1105 of the Combined Compendium of Food Additive Specifications of the Food and Agriculture Organisation of the UN (www.fao.org)). For the purpose of the present invention, muramidase activity is determined according to the turbidity assay described in example 3 ("Determination of Muramidase Activity") and the polypeptide has muramidase activity if it shows activity against one or more bacteria, such as *Micrococcus luteus* ATCC 4698 and/or *Exiguobacterium undea* (DSM14481). In one aspect, the GH25 muramidase of the present invention has at least 20%, e.g., at least 40%, at least 50%, at least 60%, at least 70%, at least 80%, at least 90%, at least 95%, or at least 100% of the muramidase activity of SEQ ID NO: 1. In one aspect, the GH24 muramidase of the present invention have at least 20%, e.g., at least 40%, at least 50%, at least 60%, at least 70%, at least 80%, at least 90%, at least 95%, or at least 100% of the muramidase activity of SEQ ID NO: 63.

Mature polypeptide: The term "mature polypeptide" means a polypeptide in its final form following translation and any post-translational modifications, such as N-terminal processing, C-terminal truncation, glycosylation, phosphorylation, etc.

Obtained or obtainable from: The term "obtained or obtainable from" means that the polypeptide may be found in an organism from a specific taxonomic rank. In one embodiment, the polypeptide is obtained or obtainable from the kingdom Fungi, wherein the term kingdom is the taxonomic rank. In a preferred embodiment, the polypeptide is obtained or obtainable from the phylum Ascomycota, wherein the term phylum is the taxonomic rank. In another preferred embodiment, the polypeptide is obtained or obtainable from the subphylum Pezizomycotina, wherein the term subphylum is the taxonomic rank. In another preferred embodiment, the polypeptide is obtained or obtainable from the class Eurotiomycetes, wherein the term class is the taxonomic rank.

If the taxonomic rank of a polypeptide is not known, it can easily be determined by a person skilled in the art by performing a BLASTP search of the polypeptide (using e.g. the National Center for Biotechnology Information (NCIB) website http://www.ncbi.nlm.nih.gov/) and comparing it to the closest homologues. The skilled person can also compare the sequence to those of the application as filed. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Roughage: The term "roughage" means dry plant material with high levels of fiber, such as fiber, bran, husks from seeds and grains and crop residues (such as stover, copra, straw, chaff, sugar beet waste).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment– Total Number of Gaps in Alignment)

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having muramidase activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position.

In one aspect, a muramidase variant may comprise from 1 to 10 alterations, i.e. 1, 2, 3, 4, 5, 6, 7, 8, 9 or 10 alterations and have at least 20%, e.g., at least 40%, at least 50%, at least 60%, at least 70%, at least 80%, at least 90%, at least 95%, or at least 100% of the muramidase activity of the parent muramidase, such as SEQ ID NO: 1 or SEQ ID NO: 63.

DETAILED DESCRIPTION OF THE INVENTION

Animal Feed and Animal Feed Additive Comprising Polypeptides Having Muramidase Activity and at Least One Probiotic It has been surprisingly found that supplementing an animal feed comprising an animal feed additive, one or more protein sources and one or more energy sources with a muramidase (preferably a fungal muramidase) and a probiotic gives an additional performance benefit in animals compared to the same animal feed but without the muramidase present.

Thus, in a first aspect, the invention relates to an animal feed comprising an animal feed additive, one or more protein sources and one or more energy sources characterised in the animal feed further comprises one or more probiotic and one or more fungal polypeptides having muramidase activity.

In one embodiment, the muramidase is a GH24 muramidase, preferably a fungal GH24 muramidase, preferably obtained or obtainable from the phylum Ascomycota, more preferably from the class Eurotiomycetes. In one embodiment, the muramidase is a GH25 muramidase, preferably a fungal GH25 muramidase, preferably obtained or obtainable from the phylum Ascomycota, more preferably from the class Eurotiomycetes. In a preferred embodiment, the muramidase is a GH25 muramidase.

In one embodiment, the invention relates to an animal feed comprising an animal feed additive, one or more protein sources and one or more energy sources characterised in that the animal feed or feed additive further comprises one or more probiotic and one or more fungal polypeptides having muramidase activity, wherein the fungal polypeptide having muramidase activity is selected from the group consisting of:

(a) a polypeptide having at least 80%, e.g., at least 85%, at least 90%, at least 95%, or 100% sequence identity to SEQ ID NO: 1;
(b) a polypeptide having at least 80%, e.g., at least 85%, at least 90%, at least 95%, or 100% sequence identity to SEQ ID NO: 2;
(c) a polypeptide having at least 80%, e.g., at least 85%, at least 90%, at least 95%, or 100% sequence identity to SEQ ID NO: 3;
(d) a polypeptide having at least 80%, e.g., at least 85%, at least 90%, at least 95%, or 100% sequence identity to SEQ ID NO: 4;
(e) a polypeptide having at least 80%, e.g., at least 85%, at least 90%, at least 95%, or 100% sequence identity to SEQ ID NO: 5;
(f) a polypeptide having at least 80%, e.g., at least 85%, at least 90%, at least 95%, or 100% sequence identity to SEQ ID NO: 6;
(g) a polypeptide having at least 80%, e.g., at least 85%, at least 90%, at least 95%, or 100% sequence identity to SEQ ID NO: 7;
(h) a polypeptide having at least 80%, e.g., at least 85%, at least 90%, at least 95%, or 100% sequence identity to SEQ ID NO: 8;
(i) a polypeptide having at least 80%, e.g., at least 85%, at least 90%, at least 95%, or 100% sequence identity to SEQ ID NO: 9;
(j) a polypeptide having at least 80%, e.g., at least 85%, at least 90%, at least 95%, or 100% sequence identity to SEQ ID NO: 10;
(k) a polypeptide having at least 80%, e.g., at least 85%, at least 90%, at least 95%, or 100% sequence identity to SEQ ID NO: 11;
(l) a polypeptide having at least 80%, e.g., at least 85%, at least 90%, at least 95%, or 100% sequence identity to SEQ ID NO: 12;
(m) a polypeptide having at least 80%, e.g., at least 85%, at least 90%, at least 95%, or 100% sequence identity to SEQ ID NO: 13;
(n) a polypeptide having at least 80%, e.g., at least 85%, at least 90%, at least 95%, or 100% sequence identity to SEQ ID NO: 14;
(o) a polypeptide having at least 80%, e.g., at least 85%, at least 90%, at least 95%, or 100% sequence identity to SEQ ID NO: 15;
(p) a polypeptide having at least 80%, e.g., at least 85%, at least 90%, at least 95%, or 100% sequence identity to SEQ ID NO: 16;
(q) a polypeptide having at least 80%, e.g., at least 85%, at least 90%, at least 95%, or 100% sequence identity to SEQ ID NO: 17;
(r) a polypeptide having at least 80%, e.g., at least 85%, at least 90%, at least 95%, or 100% sequence identity to SEQ ID NO: 18;
(s) a polypeptide having at least 80%, e.g., at least 85%, at least 90%, at least 95%, or 100% sequence identity to SEQ ID NO: 19;
(t) a polypeptide having at least 80%, e.g., at least 85%, at least 90%, at least 95%, or 100% sequence identity to SEQ ID NO: 20;
(u) a polypeptide having at least 80%, e.g., at least 85%, at least 90%, at least 95%, or 100% sequence identity to SEQ ID NO: 21;
(v) a polypeptide having at least 80%, e.g., at least 85%, at least 90%, at least 95%, or 100% sequence identity to SEQ ID NO: 22;
(w) a polypeptide having at least 80%, e.g., at least 85%, at least 90%, at least 95%, or 100% sequence identity to SEQ ID NO: 23;
(x) a polypeptide having at least 80%, e.g., at least 85%, at least 90%, at least 95%, or 100% sequence identity to SEQ ID NO: 24;
(y) a polypeptide having at least 80%, e.g., at least 85%, at least 90%, at least 95%, or 100% sequence identity to SEQ ID NO: 25;
(z) a polypeptide having at least 80%, e.g., at least 85%, at least 90%, at least 95%, or 100% sequence identity to SEQ ID NO: 26;
(aa) a polypeptide having at least 80%, e.g., at least 85%, at least 90%, at least 95%, or 100% sequence identity to SEQ ID NO: 27;
(ab) a polypeptide having at least 80%, e.g., at least 85%, at least 90%, at least 95%, or 100% sequence identity to SEQ ID NO: 28;
(ac) a polypeptide having at least 80%, e.g., at least 85%, at least 90%, at least 95%, or 100% sequence identity to SEQ ID NO: 29;
(ad) a polypeptide having at least 80%, e.g., at least 85%, at least 90%, at least 95%, or 100% sequence identity to SEQ ID NO: 30;
(ae) a polypeptide having at least 80%, e.g., at least 85%, at least 90%, at least 95%, or 100% sequence identity to SEQ ID NO: 31;
(af) a polypeptide having at least 80%, e.g., at least 85%, at least 90%, at least 95%, or 100% sequence identity to SEQ ID NO: 32;
(ag) a polypeptide having at least 80%, e.g., at least 85%, at least 90%, at least 95%, or 100% sequence identity to SEQ ID NO: 33;
(ah) a polypeptide having at least 80%, e.g., at least 85%, at least 90%, at least 95%, or 100% sequence identity to SEQ ID NO: 34;
(ai) a polypeptide having at least 80%, e.g., at least 85%, at least 90%, at least 95%, or 100% sequence identity to SEQ ID NO: 35;
(aj) a polypeptide having at least 80%, e.g., at least 85%, at least 90%, at least 95%, or 100% sequence identity to SEQ ID NO: 36;
(ak) a polypeptide having at least 80%, e.g., at least 85%, at least 90%, at least 95%, or 100% sequence identity to SEQ ID NO: 37;
(al) a polypeptide having at least 80%, e.g., at least 85%, at least 90%, at least 95%, or 100% sequence identity to SEQ ID NO: 38;
(am) a polypeptide having at least 80%, e.g., at least 85%, at least 90%, at least 95%, or 100% sequence identity to SEQ ID NO: 39;
(an) a polypeptide having at least 80%, e.g., at least 85%, at least 90%, at least 95%, or 100% sequence identity to SEQ ID NO: 40;
(ao) a polypeptide having at least 80%, e.g., at least 85%, at least 90%, at least 95%, or 100% sequence identity to SEQ ID NO: 41;
(ap) a polypeptide having at least 80%, e.g., at least 85%, at least 90%, at least 95%, or 100% sequence identity to SEQ ID NO: 42;
(aq) a polypeptide having at least 80%, e.g., at least 85%, at least 90%, at least 95%, or 100% sequence identity to SEQ ID NO: 43;
(ar) a polypeptide having at least 80%, e.g., at least 85%, at least 90%, at least 95%, or 100% sequence identity to SEQ ID NO: 44;

(as) a polypeptide having at least 80%, e.g., at least 85%, at least 90%, at least 95%, or 100% sequence identity to SEQ ID NO: 45;
(at) a polypeptide having at least 80%, e.g., at least 85%, at least 90%, at least 95%, or 100% sequence identity to SEQ ID NO: 46;
(au) a polypeptide having at least 80%, e.g., at least 85%, at least 90%, at least 95%, or 100% sequence identity to SEQ ID NO: 47;
(av) a polypeptide having at least 80%, e.g., at least 85%, at least 90%, at least 95%, or 100% sequence identity to SEQ ID NO: 48;
(aw) a polypeptide having at least 80%, e.g., at least 85%, at least 90%, at least 95%, or 100% sequence identity to SEQ ID NO: 49;
(ax) a polypeptide having at least 80%, e.g., at least 85%, at least 90%, at least 95%, or 100% sequence identity to SEQ ID NO: 50;
(ay) a polypeptide having at least 80%, e.g., at least 85%, at least 90%, at least 95%, or 100% sequence identity to SEQ ID NO: 51;
(az) a polypeptide having at least 80%, e.g., at least 85%, at least 90%, at least 95%, or 100% sequence identity to SEQ ID NO: 52;
(ba) a polypeptide having at least 80%, e.g., at least 85%, at least 90%, at least 95%, or 100% sequence identity to SEQ ID NO: 53;
(bb) a polypeptide having at least 80%, e.g., at least 85%, at least 90%, at least 95%, or 100% sequence identity to SEQ ID NO: 54;
(bc) a polypeptide having at least 80%, e.g., at least 85%, at least 90%, at least 95%, or 100% sequence identity to SEQ ID NO: 55;
(bd) a polypeptide having at least 80%, e.g., at least 85%, at least 90%, at least 95%, or 100% sequence identity to SEQ ID NO: 56;
(be) a polypeptide having at least 80%, e.g., at least 85%, at least 90%, at least 95%, or 100% sequence identity to SEQ ID NO: 57;
(bf) a polypeptide having at least 80%, e.g., at least 85%, at least 90%, at least 95%, or 100% sequence identity to SEQ ID NO: 58;
(bg) a polypeptide having at least 80%, e.g., at least 85%, at least 90%, at least 95%, or 100% sequence identity to SEQ ID NO: 59;
(bh) a polypeptide having at least 80%, e.g., at least 85%, at least 90%, at least 95%, or 100% sequence identity to SEQ ID NO: 60;
(bi) a polypeptide having at least 80%, e.g., at least 85%, at least 90%, at least 95%, or 100% sequence identity to SEQ ID NO: 61;
(bj) a polypeptide having at least 80%, e.g., at least 85%, at least 90%, at least 95%, or 100% sequence identity to SEQ ID NO: 62;
(bk) a polypeptide having at least 80%, e.g., at least 85%, at least 90%, at least 95%, or 100% sequence identity to SEQ ID NO: 63;
(bl) a polypeptide having at least 80%, e.g., at least 85%, at least 90%, at least 95%, or 100% sequence identity to SEQ ID NO: 64;
(bm) a polypeptide having at least 80%, e.g., at least 85%, at least 90%, at least 95%, or 100% sequence identity to SEQ ID NO: 65;
(bn) a polypeptide having at least 80%, e.g., at least 85%, at least 90%, at least 95%, or 100% sequence identity to SEQ ID NO: 66;
(bo) a polypeptide having at least 80%, e.g., at least 85%, at least 90%, at least 95%, or 100% sequence identity to SEQ ID NO: 67;
(bp) a polypeptide having at least 80%, e.g., at least 85%, at least 90%, at least 95%, or 100% sequence identity to SEQ ID NO: 68;
(bq) a polypeptide having at least 80%, e.g., at least 85%, at least 90%, at least 95%, or 100% sequence identity to SEQ ID NO: 69;
(br) a polypeptide having at least 80%, e.g., at least 85%, at least 90%, at least 95%, or 100% sequence identity to SEQ ID NO: 70;
(bs) a polypeptide having at least 80%, e.g., at least 85%, at least 90%, at least 95%, or 100% sequence identity to SEQ ID NO: 71;
(bt) a variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, SEQ ID NO:12, SEQ ID NO:13, SEQ ID NO:14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70 or SEQ ID NO: 71 comprising one or more amino acid substitutions (preferably conservative substitutions), and/or one or more amino acid deletions, and/or one or more amino acid insertions or any combination thereof in 1, 2, 3, 4, 5, 6, 7, 8, 9 or 10 positions;
(bu) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) and a N-terminal and/or C-terminal extension of between 1 and 10 amino acids; and
(bv) a fragment of a polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) having muramidase activity and having at least 90% of the length of the mature polypeptide.

In one embodiment, the muramidase comprises or consists of amino acids 1 to 208 of SEQ ID NO: 1, amino acids 1 to 213 of SEQ ID NO: 2, amino acids 1 to 218 of SEQ ID NO: 3, amino acids 1 to 208 of SEQ ID NO: 4, amino acids 1 to 215 of SEQ ID NO: 5, amino acids 1 to 207 of SEQ ID NO: 6, amino acids 1 to 201 of SEQ ID NO: 7, amino acids 1 to 201 of SEQ ID NO: 8, amino acids 1 to 203 of SEQ ID NO: 9, amino acids 1 to 208 of SEQ ID NO: 10, amino acids 1 to 207 of SEQ ID NO: 11, amino acids 1 to 208 of SEQ ID NO: 12, amino acids 1 to 207 of SEQ ID NO: 13, amino acids 1 to 207 of SEQ ID NO: 14, amino acids 1 to 207 of SEQ ID NO: 15, amino acids 1 to 208 of SEQ ID NO: 16, amino acids 1 to 208 of SEQ ID NO: 17, amino acids 1 to 206 of SEQ ID NO: 18, amino acids 1 to 207 of SEQ ID NO: 19, amino acids 1 to 216 of SEQ ID NO: 20, amino acids 1 to 218 of SEQ ID NO: 21, amino acids 1 to 204 of SEQ ID NO: 22, amino acids 1 to 203 of SEQ ID NO: 23, amino acids 1 to 208 of SEQ ID NO: 24, amino acids 1 to 210 of SEQ ID NO: 25, amino acids 1 to 207 of SEQ ID NO: 26, amino acids 1 to 207 of SEQ ID NO: 27, amino acids 1 to 208 of SEQ ID NO: 28, amino acids 1 to 217 of SEQ ID NO: 29, amino acids 1 to 208 of SEQ ID NO: 30, amino acids 1 to 201 of SEQ ID NO: 31, amino acids 1 to 202 of SEQ ID NO: 32, amino acids 1 to 207 of SEQ ID NO: 33, amino acids 1 to 202 of SEQ ID NO: 34, amino acids 1 to 201 of SEQ ID NO: 35, amino acids 1 to 202 of SEQ ID NO: 36, amino acids 1 to 206 of SEQ ID NO: 37, amino acids 1 to 202 of SEQ ID NO: 38, amino acids 1 to 202 of SEQ ID NO: 39, amino acids 1 to 202 of SEQ ID NO: 40, amino acids 1 to 202 of SEQ ID NO: 41, amino acids 1 to 206 of SEQ ID NO: 42, amino acids 1 to 207 of SEQ ID NO: 43, amino acids 1 to 208 of SEQ ID NO: 44, amino acids 1 to 215 of SEQ ID NO: 45, amino acids 1 to 217 of SEQ ID NO: 46, amino acids 1 to 214 of SEQ ID NO: 47, amino acids 1 to 208 of SEQ ID NO: 48, amino acids 1 to 203 of SEQ ID NO: 49, amino acids 1 to 216 of SEQ ID NO: 50, amino acids 1 to 207 of SEQ ID NO: 51, amino acids 1 to 208 of SEQ ID NO: 52, amino acids 1 to 207 of SEQ ID NO: 53, amino acids 1 to 208 of SEQ ID NO: 54, amino acids 1 to 207 of SEQ ID NO: 55, amino acids 1 to 207 of SEQ ID NO: 56, amino acids 1 to 208 of SEQ ID NO: 57, amino acids 1 to 207 of SEQ ID NO: 58, amino acids 1 to 207 of SEQ ID NO: 59, amino acids 1 to 207 of SEQ ID NO: 60, amino acids 1 to 204 of SEQ ID NO: 61, amino acids 1 to 216 of SEQ ID NO: 62, amino acids 1 to 245 of SEQ ID NO: 63, amino acids 1 to 249 of SEQ ID NO: 64, amino acids 1 to 248 of SEQ ID NO: 65, amino acids 1 to 245 of SEQ ID NO: 66, amino acids 1 to 249 of SEQ ID NO: 67, amino acids 1 to 245 of SEQ ID NO: 68, amino acids 1 to 247 of SEQ ID NO: 69, amino acids 1 to 250 of SEQ ID NO: 70 or amino acids 1 to 240 of SEQ ID NO: 71.

In an embodiment of the invention, the muramidase has at least 90% sequence identity with the enzyme of the commercial product Balancius™. Typically, the muramidase has at least 95% sequence identity with the enzyme of the commercial product Balancius™, such as at least 98% sequence identity or at least 99% sequence identity. Balancius™ is defined herein by SEQ ID NO:1 or SEQ ID NO. 2.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/le, Leu/Val, Ala/Glu, and Asp/Gly. Other examples of conservative substitutions are G to A; A to G, S; V to 1, L, A, T, S; I to V, L, M; L to 1, M, V; M to L, 1, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for muramidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

WO 2013/076253 disclosed that amino acid residues D95 and E97 of SEQ ID NO: 8 of WO 2013/076253 are catalytic residues. PCT/CN2017/075960 discloses the catalytic amino acids of 12 GH25 muramidases. This alignment can be used to determine the position of the catalytic amino acids for the claimed muramidases. In one embodiment, no alteration is made to an amino acid corresponding to E97 and D95 when using SEQ ID NO: 39 for numbering. The catalytic amino acids for the GH24 muramidases can be determined by aligning the sequences with known sequences where the catalytic amino acid(s) have already been determined (see www.uniprot.org).

The invention relates to an animal feed or animal feed additive comprising an animal feed additive, one or more protein sources and one or more energy sources characterised in that the animal feed or feed additive further comprises one or more probiotic one or more fungal polypeptides having muramidase activity, wherein the probiotic is selected from any micro-organisms that is associated with a health benefit on the host.

In a typical embodiment, the one or more probiotic can be selected from the group consisting of a *Lactobacillus*, a *Bifidobacterium*, a *Saccharomyces*, an *Enterococcus*, a *Streptococcus*, a *Pediococcus*, a *Leuconostoc*, a *Lactococcus*, an *Oenococcus*, a *Bacillus, Carnobacterium, Propionibacterium, Clostridium, Megasphaera* and an *Escherichia* or combinations thereof.

In a suitable embodiment, the animal feed composition comprises one or more probiotics selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediococsus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii*, and *Propionibacteria* sp.

In a further suitable embodiment, the *Lactobacillus* strain can be selected from the group consisting of *Lactobacillus*

*acidophilus; Lactobacillus casei; Lactobacillus gasseri; Lactobacillus rhamnosus; Lactobacillus salivarius; Lactobacillus reuteri, Lactobacillus bulgaricus, Lactobacillus helveticus, Lactobacillus crispatus, Lactobacillus amylovorus, Lactobacillus gallinarum, Lactobacillus sakei, Lactobacillus curvatus, Lactobacillus plantarum, Lactobacillus paracasei, Lactobacillus pentosus* and *Lactobacillus johnsonii* and combinations thereof.

Preferred embodiments of *Lactobacillus* can be selected from the group consisting of *Lactobacillus acidophilus; Lactobacillus casei; Lactobacillus reuteri, Lactobacillus bulgaricus, Lactobacillus helveticus*, and *Lactobacillus johnsonii* and combinations thereof.

The *Bifidobacterium* may include various Gram positive non-motile anaerobic bacteria. Strains of the genus *Bifidobacterium* are also often used as probiotic bacteria as they are known for their variety of resistance mechanisms to bile salts, which is important since the beneficial effects of probiotic bacteria is often generated in the presence of this biological fluid. The Bifidobacteria may be selected from the group consisting of *Bifidobacterium bifidum; Bifidobacterium animalis; Bifidobacterium infantis; Bifidobacterium adolescentis, Bifidobacterium longum*, and *Bifidobacterium breve*.

The *Saccharomyces* may be selected from the group consisting of *Saccharomyces cerevisiae, Saccharomyces bayanus, Saccharomyces thermophilus* and *Saccharomyces boulardii*, particularly *Saccharomyces thermophilus* and *Saccharomyces boulardii*.

A suitable *Lactococcus* is *Lactococcus lactis*.

In a suitable embodiment, the *Enterococcus* is selected from the group consisting of *Enterococcus durans* and *Enterococcus faecium*.

In a suitable embodiment, the *Streptococcus* is *Streptococcus thermophilus*.

In a suitable embodiment, the *Bacillus* is selected from the group consisting *Bacillus subtilis, Bacillus coagulans, Bacillus amyloliquefaciens, Bacillus lichenformis, Bacillus subtilis, Bacillus cereus. Bacillus cereus*, namely *Bacillus cereus* NVH 75/95 is an efficient probiotic for animals.

In a typical embodiment, the composition, animal feed additive or animal feed comprises a probiotic from one or more of the following strains of *Bacillus subtilis*: 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, DSM 32315, NRRL B-50136, NRRL B-50605, NRRL B-50606, NRRL B-50622 and PTA-7547. Suitably, the composition, animal feed additive or animal feed further comprises a probiotic from one or more of the following strains of *Bacillus pumilus*: NRRL B-50016, ATCC 700385, NRRL B-50885 or NRRL B-50886.

In a further typical embodiment, the composition, animal feed additive or animal feed comprises a probiotic from one or more of the following strains of *Bacillus* lichenformis: NRRL B 50015, NRRL B-50621 or NRRL B-50623.

In a further suitable embodiment, composition, animal feed additive or animal feed comprises a probiotic from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888.

In a suitable embodiment, the *Escherichia* is selected from the group consisting of *Escherichia coli* Nissle, such as *Escherichia coli* Nissle 1917.

In an interesting embodiment, the animal feed or animal feed additive of the invention is characterised in that the one or more probiotic is a combination comprising a *Bacillus subtilis* strain 2084 Accession No. NRRI B-50013, *Bacillus subtilis* strain LSSAO1 Accession No. NRRL B-50104 and *Bacillus subtilis* strain 15A-P4 ATCC Accession No. PTA-65.

In a further interesting embodiment, the animal feed or animal feed additive of the invention is characterised in that the one or more probiotic is *Bacillus subtilis* Strain C3102.

As stated, in a typical embodiment, the composition, animal feed additive or animal feed comprises a combination of probiotics selected from the group consisting of *Lactobacillus*, a *Bifidobacterium*, a *Saccharomyces*, an *Enterococcus*, a *Streptococcus*, a *Pediococcus*, a *Leuconostoc*, a *Lactococcus*, an *Oenococcus*, a *Bacillus, Carnobacterium, Propionibacterium, Clostridium, Megasphaera* and an *Escherichia*. Preferred combinations include a combination of one or more *Lactobacillus* and one or more *Saccharomyces*, one or more *Lactobacillus* and one or more *Streptococcus*, one or more *Lactobacillus* and one or more *Bacillus*, one or more *Lactobacillus* and one or more *Bifidobacterium*, one or more *Saccharomyces* and one or more *Streptococcus*, one or more *Saccharomyces* and one or more *Bacillus*, one or more *Saccharomyces* and one or more *Bifidobacterium*, one or more *Saccharomyces* and one or more *Bacillus*, one or more *Streptococcus* and one or more *Bifidobacterium*, one or more *Streptococcus* and one or more *Bacillus*, one or more *Bacillus* and one or more *Bifidobacterium*.

In another typical embodiment, the composition, animal feed additive or animal feed comprises a combination of *Lactobacillus* strains such as a combination of *Lactobacillus acidophilus* and *L. johnsonii; Lactobacillus acidophilus* and *L. casei; Lactobacillus acidophilus* and *Lactobacillus rhamnosus; L. johnsonii* and *Lactobacillus acidophilus; L. johnsonii* and *L. casei*; and *L. johnsonii* and *Lactobacillus rhamnosus*.

In a further embodiment, the composition, animal feed additive or animal feed comprises a combination of *S. thermophilus* and *L. bulgaricus*. Another suitable combination can be selected from the group consisting of *Lactobacillus acidophilus, Lactobacillus rhamnosus, Saccharomyces boulardii, Bifidobacterium bifidum* and *Bacillus coagulans*.

In another embodiment, the one or more bacterial strains acting as probiotics are present in the form of a stable spore.

The bacterial count of each of the bacterial strains acting as probiotics in the animal feed composition is typically between $1 \times 10^4$ and $1 \times 10^{14}$ CFU/kg of dry matter, preferably between $1 \times 10^6$ and $1 \times 10^{12}$ CFU/kg of dry matter, and more preferably between $1 \times 10^7$ and $1 \times 10^{11}$ CFU/kg of dry matter. In a more preferred embodiment the bacterial count of each of the bacterial strains in the animal feed composition is between $1 \times 10^8$ and $1 \times 10^{10}$ CFU/kg of dry matter.

The bacterial count of each of the bacterial strains acting as probiotics in the animal feed composition is between $1 \times 10^5$ and $1 \times 10^{15}$ CFU/animal/day, preferably between $1 \times 10^7$ and $1 \times 10^{13}$ CFU/animal/day, and more preferably between $1 \times 10^8$ and $1 \times 10^{12}$ CFU/animal/day. In a more preferred embodiment the bacterial count of each of the bacterial strains in the animal feed composition is between $1 \times 10^9$ and $1 \times 10^{11}$ CFU/animal/day. In one embodiment, the amount of probiotics is 0.001% to 10% by weight of the composition.

Examples of commercial products acting as probiotics are Cylactin® (DSM Nutritional Products), Alterion (Adisseo), Enviva PRO (DuPont Animal Nutrition), Syncra® (mix enzyme+probiotic, DuPont Animal Nutrition), Calsporin®, Gallipro®, GalliproMax®, Proflora®, Ecobiol® and Fecinor® (Norel/Evonik), CSI®, Sorbiflora®, Animavit®, and GutCare® PY1 (Evonik). In a suitable embodiment, the probiotic is selected from the group consisting of any one of Cylactin® (DSM Nutritional Products), Alterion (Adisseo), Enviva PRO (DuPont Animal Nutrition), Syncra® (mix enzyme+probiotic, DuPont Animal Nutrition), Calsporin®, Gallipro®, GalliproMax®, Proflora®, Ecobiol® and Fecinor® (Norel/Evonik), CSI®, Sorbiflora®, Animavit®, and GutCare® PY1 (Evonik) and the muramidase is a muramidase having at least 90% sequence identity with As stated, in a preferred embodiment, the muramidase is a GH25 muramidase. It has surprisingly been found that GH25 muramidases may improve the intestinal health in an animal by reducing the amount of dead *Lactobacillus johnsonii* cells in the digestive tract of said animal. In a combination of interesting embodiments of the invention, the muramidase is a GH25 muramidase and the one or more probiotic comprises *Lactobacillus johnsonii*. Without being bound to particularly theory, the composition, animal feed additive or animal feed comprising a GH25 muramidase and the one or more probiotic, such as *Lactobacillus johnsonii* improves gut health in an animal.

Prebiotics are substances that induce the growth or activity of microorganisms (e.g., bacteria and fungi) that contribute to the well-being of their host. Prebiotics are typically non-digestible fiber compounds that pass undigested through the upper part of the gastrointestinal tract and stimulate the growth or activity of advantageous bacteria that colonize the large bowel by acting as substrate for them. Normally, prebiotics increase the number or activity of bifidobacteria and lactic acid bacteria in the GI tract.

Yeast derivatives (inactivated whole yeasts or yeast cell walls) can also be considered as prebiotics. They often comprise mannan-oligosaccharids, yeast beta-glucans or protein contents and are normally derived from the cell wall of the yeast, *Saccharomyces cerevisiae*.

In one embodiment, the amount of prebiotic is 0.001% to 10% by weight of the composition. Examples of yeast products are Yang® and Agrimos (Lallemand Animal Nutrition).

In a further typical embodiment, the composition, animal feed additive or animal feed, or methods of the invention comprise the commercial product Balancius™, or a muramidase having at least 90% sequence identity with the enzyme of the commercial product Balancius™, in combination with a probiotic from one or more of the following strains of *Bacillus* lichenformis: NRRL B 50015, NRRL B-50621 or NRRL B-50623. Typically, the combination comprises a muramidase having at least 95% sequence identity with the enzyme of the commercial product Balancius™, such as at least 98% sequence identity or at least 99% sequence identity.

In a further suitable embodiment, the composition, animal feed additive or animal feed, or methods of the invention comprise the commercial product Balancius™, or a muramidase having at least 90% sequence identity with the enzyme of the commercial product Balancius™, in combination with a probiotic from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888. Typically, the combination comprises a muramidase having at least 95% sequence identity with the enzyme of the commercial product Balancius™, such as at least 98% sequence identity or at least 99% sequence identity.

In a suitable embodiment, the composition, animal feed additive or animal feed, or methods of the invention comprises the commercial product Balancius™, or a muramidase having at least 90% sequence identity with the enzyme of the commercial product Balancius™ in combination with an *Escherichia* selected from the group consisting of *Escherichia coli* Nissle, such as *Escherichia coli* Nissle 1917. Typically, the combination comprises a muramidase having at least 95% sequence identity with the enzyme of the commercial product Balancius™ such as at least 98% sequence identity or at least 99% sequence identity.

In an interesting embodiment, the composition, animal feed additive or animal feed, or methods of the invention comprise the commercial product Balancius™, or a muramidase having at least 90% sequence identity with the enzyme of the commercial product Balancius™ in combination with a combination of probiotics, said combination comprising a *Bacillus subtilis* strain 2084 Accession No. NRRI B-50013, *Bacillus subtilis* strain LSSAO1 Accession No. NRRL B-50104 and *Bacillus subtilis* strain 15A-P4 ATCC Accession No. PTA-65. Typically, the combination comprises a muramidase having at least 95% sequence identity with the enzyme of the commercial product Balancius™, such as at least 98% sequence identity or at least 99% sequence identity.

In a further interesting embodiment, the composition, animal feed additive or animal feed, or methods of the invention comprise the commercial product Balancius™, or a muramidase having at least 90% sequence identity with the enzyme of the commercial product Balancius™, in combination with the probiotic *Bacillus subtilis* Strain C3102. Typically, the combination comprises a muramidase having at least 95% sequence identity with the enzyme of the commercial product Balancius™, such as at least 98% sequence identity or at least 99% sequence identity.

In a suitable embodiment, the probiotic is selected from the group consisting of any one of Cylactin® (DSM Nutritional Products), Alterion (Adisseo), Enviva PRO (DuPont Animal Nutrition), Syncra® (mix enzyme+probiotic, DuPont Animal Nutrition), Calsporin®, Gallipro®, GalliproMax®, Proflora®, Ecobiol® and Fecinor® (Norel/Evonik), CSI®, Sorbiflora®, Animavit®, and GutCare® PY1 (Evonik) and the muramidase is selected from the group consisting of the commercial product Balancius™, or a muramidase having at least 90% sequence identity with the enzyme of the commercial product Balancius™, such as at least 95% sequence identity with the enzyme of the commercial product Balancius™, such as at least 98% sequence identity or at least 99% sequence identity.

Balancius™ is defined herein by SEQ ID NO:1 or SEQ ID NO. 2.

In one embodiment, the BWG is improved by at least 1%, such as by at least 1.5%, at least 2.0%, at least 2.5%, at least 3%, at least 3.5%, at least 4% or at least 5%. In another embodiment, the BWG is improved by between 1% and 15%, such as between 1% and 12%, between 1% and 10%, 1.5% and 8%, 2.0% and 7%, or any combination of these intervals.

In one embodiment, the FCR is improved by at least 1%, such as by at least 1.25%, at least 1.5% or at least 1.75%. In another embodiment, the FCR is improved by between 1% and 5%, such as between 1% and 4%, between 1% and 3%, 1.25% and 2.5%, 1.5% and 2%, or any combination of these intervals. muramidase In one embodiment, the polypeptide having muramidase activity is dosed at a level of 0.1 to 150 ppm enzyme protein per kg animal feed, such as 0.5 to 100 ppm, 1 to 75 ppm, 2 to 50 ppm, 3 to 25 ppm, 2 to 80 ppm, 5 to 60 ppm, 8 to 40 ppm, 10 to 30 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the animal is a mono-gastric animal, e.g. pigs or swine (including, but not limited to, piglets, growing pigs, and sows); poultry (including but not limited to poultry, turkey, duck, quail, guinea fowl, goose, pigeon, squab, chicken, broiler, layer, pullet and chick); fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns). In a more preferred embodiment, the animal is selected from the group consisting of swine, poultry, crustaceans and fish. In an even more preferred embodiment, the animal is selected from the group consisting of swine, piglet, growing pig, sow, chicken, broiler, layer, pullet and chick.

In one embodiment, the polypeptide having muramidase activity is dosed between 0.001% to 25% w/w of liquid formulation, preferably 0.01% to 25% w/w, more preferably 0.05% to 20% w/w, more preferably 0.2% to 15% w/w, even more preferably 0.5% to 15% w/w or most preferably 1.0% to 10% w/w polypeptide.

In one embodiment, the liquid formulation further comprises 20%-80% polyol (i.e. total amount of polyol), preferably 25%-75% polyol, more preferably 30%-70% polyol, more preferably 35%-65% polyol or most preferably 40%-60% polyol. In one embodiment, the liquid formulation comprises 20%-80% polyol, preferably 25%-75% polyol, more preferably 30%-70% polyol, more preferably 35%-65% polyol or most preferably 40%-60% polyol wherein the polyol is selected from the group consisting of glycerol, sorbitol, propylene glycol (MPG), ethylene glycol, diethylene glycol, triethylene glycol, 1,2-propylene glycol or 1,3-propylene glycol, dipropylene glycol, polyethylene glycol (PEG) having an average molecular weight below about 600 and polypropylene glycol (PPG) having an average molecular weight below about 600. In one embodiment, the liquid formulation comprises 20%-80% polyol (i.e. total amount of polyol), preferably 25%-75% polyol, more preferably 30%-70% polyol, more preferably 35%-65% polyol or most preferably 40%-60% polyol wherein the polyol is selected from the group consisting of glycerol, sorbitol and propylene glycol (MPG).

In one embodiment, the liquid formulation further comprises preservative, preferably selected from the group consisting of sodium sorbate, potassium sorbate, sodium benzoate and potassion benzoate or any combination thereof. In one embodiment, the liquid formulation comprises 0.02% to 1.5% w/w preservative, more preferably 0.05% to 1.0% w/w preservative or most preferably 0.1% to 0.5% w/w preservative. In one embodiment, the liquid formulation comprises 0.001% to 2.0% w/w preservative (i.e. total amount of preservative), preferably 0.02% to 1.5% w/w preservative, more preferably 0.05% to 1.0% w/w preservative or most preferably 0.1% to 0.5% w/w preservative wherein the preservative is selected from the group consisting of sodium sorbate, potassium sorbate, sodium benzoate and potassium benzoate or any combination thereof.

In one embodiment, the liquid formulation comprises one or more formulating agents (such as those described herein), preferably a formulating agent selected from the list consisting of glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the list consisting of 1,2-propylene glycol, 1,3-propylene glycol, sodium sulfate, dextrin, cellulose, sodium thiosulfate, kaolin and calcium carbonate.

In one embodiment, the protein source is selected from the group consisting of soybean, wild soybean, beans, lupin, tepary bean, scarlet runner bean, slimjim bean, lima bean, French bean, Broad bean (fava bean), chickpea, lentil, peanut, Spanish peanut, canola, sunflower seed, cotton seed, rapeseed (oilseed rape) or pea or in a processed form such as soybean meal, full fat soy bean meal, soy protein concentrate (SPC), fermented soybean meal (FSBM), sunflower meal, cotton seed meal, rapeseed meal, fish meal, bone meal, feather meal, whey or any combination thereof.

In one embodiment, the energy source is selected from the group consisting of maize, corn, sorghum, barley, wheat, oats, rice, triticale, rye, beet, sugar beet, spinach, potato, cassava, quinoa, cabbage, switchgrass, millet, pearl millet, foxtail millet or in a processed form such as milled corn, milled maize, potato starch, cassava starch, milled sorghum, milled switchgrass, milled millet, milled foxtail millet, milled pearl millet, or any combination thereof.

In one embodiment, the animal feed additive further comprises one or more components selected from the list consisting of one or more additional enzymes; one or more microbes; one or more vitamins; one or more minerals; one or more amino acids; and one or more other feed ingredients, as described herein.

In one embodiment, the animal feed additive further comprises one or more additional enzymes, preferably wherein the enzyme is selected from the group consisting of phytase, galactanase, alpha-galactosidase, beta-galactosidase, protease, xylanase, phospholipase A1, phospholipase A2, lysophospholipase, phospholipase C, phospholipase D, amylase, arabinofuranosidase, beta-xylosidase, acetyl xylan esterase, feruloyl esterase, cellulase, cellobiohydrolases, beta-glucosidase, pullulanase, mannosidase, mannanase and beta-glucanase or any combination thereof.

In one embodiment, the animal feed additive further comprises one or more microbes, preferably wherein the microbe is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococsus acidilactici, Pediococcus* sp., *Propionibacterium thoenii, Propionibacterium* sp. and *Streptococcus* sp. or any combination thereof.

In one embodiment, the animal feed additive further comprises one or more vitamins as described herein. In one embodiment, the animal feed additive further comprises one or more minerals as described herein. In one embodiment, the animal feed additive further comprises one or more eubiotics as described herein. In one embodiment, the animal feed additive further comprises one or more prebiotics as described herein. In one embodiment, the animal feed additive further comprises one or more organic acids as described herein. In one embodiment, the animal feed additive further comprises one or more eubiotics as described herein.

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g. as disclosed in WO2000/70034). The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In one embodiment, the composition is a solid composition, such as a spray dried composition, comprising the muramidase of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the muramidase of the invention optionally combined with one or more additional enzymes. The granule is composed of a core, and optionally one or more coatings (outer layers) surrounding the core.

Typically the granule/particle size, measured as equivalent spherical diameter (volume based average particle size), of the granule is 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In some embodiments, the thickness of the coating is below 100 µm, such as below 60 µm, or below 40 µm.

The coating should encapsulate the core unit by forming a substantially continuous layer. A substantially continuous layer is to be understood as a coating having few or no holes, so that the core unit is encapsulated or enclosed with few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 µm, such as less than 10 µm or less than 5 µm.

The salt coating may comprise a single salt or a mixture of two or more salts. The salt may be water soluble, in particular having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO1997/05245, WO1998/54980, WO1998/55599, WO2000/70034, WO2006/034710, WO2008/017661, WO2008/017659, WO2000/020569, WO2001/004279, WO1997/05245, WO2000/01793, WO2003/059086, WO2003/059087, WO2007/031483, WO2007/031485, WO2007/044968, WO2013/192043, WO2014/014647 and WO2015/197719 or polymer coating such as described in WO 2001/00042.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4C (CH20° C.=79.5%), (NH4)2HPO4 (CH20° C.=93.0%), NH4H2PO4 (CH20° C.=93.1%), (NH4)2SO4 (CH20° C.=81.1%), KCl (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e. a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4·7H2O), zinc sulfate heptahydrate (ZnSO4·7H2O), sodium phosphate dibasic heptahydrate (Na2HPO4·7H2O), magnesium nitrate hexahydrate (Mg(NO3)2(6H2)), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; micro-crystalline wax; paraffin's; and fatty acids, such as hydrogenated linear long chained fatty acids and derivatives thereof. A preferred wax is palm oil or hydrogenated palm oil.

The granule may comprise a core comprising the muramidase of the invention, one or more salt coatings and one or more wax coatings. Examples of enzyme granules with multiple coatings are shown in WO1993/07263, WO1997/23606 and WO2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises one or more probiotic and one or more polypeptides having muramidase activity as described herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington DC).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or quinoa. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) muramidase enzyme preparation may also be added before or during the feed ingredient step.

In another embodiment, the composition comprises one or more of the polypeptides of the invention, one or more formulating agents and one or more additional enzymes. In an embodiment, the composition comprises one or more of the polypeptides of the invention, one or more formulating agents and one or more microbes. In an embodiment, the composition comprises one or more of the polypeptides of the invention, one or more formulating agents and one or more vitamins. In an embodiment, the composition comprises one or more of the polypeptides of the invention and one or more minerals. In an embodiment, the composition comprises the polypeptide of the invention, one or more formulating agents and one or more amino acids. In an embodiment, the composition comprises one or more of the polypeptides of the invention, one or more formulating agents and one or more other feed ingredients.

In a further embodiment, the composition comprises one or more of the polypeptides of the invention, one or more formulating agents and one or more components selected from the list consisting of: one or more additional enzymes; one or more microbes; one or more vitamins; one or more minerals; one or more amino acids; and one or more other feed ingredients.

The final muramidase concentration in the diet is within the range of 0.01-200 ppm enzyme protein per kg animal feed, such as 0.1 to 150 ppm, 0.5 to 100 ppm, 1 to 75 ppm, 2 to 50 ppm, 3 to 25 ppm, 2 to 80 ppm, 5 to 60 ppm, 8 to 40 ppm or 10 to 30 ppm enzyme protein per kg animal feed, or any combination of these intervals.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

In another embodiment, the compositions described herein optionally include one or more enzymes. Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, galactanase, mannanase, dextranase, muramidase and galactosidase is described in Henrissat et al, "The carbohydrate-active enzymes database (CAZy) in 2013", Nucl. Acids Res. (1 Jan. 2014) 42 (D1): D490-D495; see also www.cazy.org.

Thus the composition of the invention may also comprise at least one other enzyme selected from the group comprising of acetylxylan esterase (EC 3.1.1.23), acylglycerol lipase (EC 3.1.1.72), alpha-amylase (EC 3.2.1.1), beta-amylase (EC 3.2.1.2), arabinofuranosidase (EC 3.2.1.55), cellobiohydrolases (EC 3.2.1.91), cellulase (EC 3.2.1.4), feruloyl esterase (EC 3.1.1.73), galactanase (EC 3.2.1.89), alpha-galactosidase (EC 3.2.1.22), beta-galactosidase (EC 3.2.1.23), beta-glucanase (EC 3.2.1.6), beta-glucosidase (EC 3.2.1.21), triacylglycerol lipase (EC 3.1.1.3), lysophospholipase (EC 3.1.1.5), muramidase (EC 3.2.1.17), alpha-mannosidase (EC 3.2.1.24), beta-mannosidase (mannanase) (EC 3.2.1.25), phytase (EC 3.1.3.8, EC 3.1.3.26, EC 3.1.3.72), phospholipase A1 (EC 3.1.1.32), phospholipase A2 (EC 3.1.1.4), phospholipase D (EC 3.1.4.4), pullulanase (EC 3.2.1.41), pectinesterase (EC 3.1.1.11), beta-xylosidase (EC 3.2.1.37), or any combination thereof.

In a particular embodiment the composition of the invention comprises a galactanase (EC 3.2.1.89) and a beta-galactosidase (EC 3.2.1.23).

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), AveMix® Phytase (Aveve Biochem), Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio® Excel or Rovabio® Advance (Adisseo).

Eubiotics

Eubiotics are compounds which are designed to give a healthy balance of the micro-flora in the gastrointestinal tract. Eubiotics cover a number of different feed additives, such as probiotics, prebiotics, phytogenics (essential oils) and organic acids which are described in more detail below.

Phytogenics

Phytogenics are a group of natural growth promoters or non-antibiotic growth promoters used as feed additives, derived from herbs, spices or other plants. Phytogenics can be single substances prepared from essential oils/extracts, essential oils/extracts, single plants and mixture of plants (herbal products) or mixture of essential oils/extracts/plants (specialized products).

Examples of phytogenics are rosemary, sage, oregano, thyme, clove, and lemongrass. Examples of essential oils are thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and curcuma extract.

In one embodiment, the amount of phytogeneics is 0.001% to 10% by weight of the composition. Examples of commercial products are Crina® (DSM Nutritional Products); Cinergy™, Biacid™, ProHacid™ Classic and Pro-Hacid™ Advance™ (all Promivi/Cargill) and Envivo EO (DuPont Animal Nutrition).

Organic Acids

Organic acids (C1-C7) are widely distributed in nature as normal constituents of plants or animal tissues. They are also formed through microbial fermentation of carbohydrates mainly in the large intestine. They are often used in swine and poultry production as a replacement of antibiotic growth promoters since they have a preventive effect on the intestinal problems like necrotic enteritis in chickens and *Escherichia coli* infection in young pigs. Organic acids can be sold as mono component or mixtures of typically 2 or 3 different organic acids. Examples of organic acids are short chain fatty acids (e.g. formic acid, acetic acid, propionic acid, butyric acid), medium chain fatty acids (e.g. caproic acid, caprylic acid, capric acid, lauric acid), di/tri-carboxylic acids (e.g. fumaric acid), hydroxy acids (e.g. lactic acid), aromatic acids (e.g. benzoic acid), citric acid, sorbic acid, malic acid, and tartaric acid or their salt (typically sodium or potassium salt such as potassium diformate or sodium butyrate).

In one embodiment, the amount of organic acid is 0.001% to 10% by weight of the composition. Examples of commercial products are VevoVitall® (DSM Nutritional Products), Amasil®, Luprisil®, Lupro-Grain®, Lupro-Cid®, Lupro-Mix® (BASF), n-Butyric Acid AF (OXEA) and Adimix Precision (Nutriad).

Premix

The incorporation of the composition of feed additives as exemplified herein above to animal feeds, for example poultry feeds, is in practice carried out using a concentrate or a premix. A premix designates a preferably uniform mixture of one or more micro ingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

Amino Acids

The composition of the invention may further comprise one or more amino acids. Examples of amino acids which are used in animal feed are lysine, alanine, beta-alanine, threonine, methionine and tryptophan. In one embodiment, the amount of amino acid is 0.001% to 10% by weight of the composition.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin C, vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, iodine, selenium and zinc.

Non-limiting examples of macro minerals include calcium, magnesium, phosphorus, potassium and sodium.

In one embodiment, the amount of vitamins is 0.001% to 10% by weight of the composition. In one embodiment, the amount of minerals is 0.001% to 10% by weight of the composition.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
|---|---|---|
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise additional colouring agents, stabilisers, growth improving additives and aroma compounds/flavourings, polyunsaturated fatty acids (PUFAs); reactive oxygen generating species, antioxidants, anti-microbial peptides, antifungal polypeptides and mycotoxin management compounds.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a synthetase.

Antioxidants can be used to limit the number of reactive oxygen species which can be generated such that the level of reactive oxygen species is in balance with antioxidants.

Mycotoxins, such as deoxynivalenol, aflatoxin, zearalenone and fumonisin can be found in animal feed and can result in negative animal performance or illness. Compounds which can manage the levels of mycotoxin, such as via deactivation of the mycotoxin or via binding of the mycotoxin, can be added to the feed to ameliorate these negative effects. Examples of mycotoxin management compounds are Vitafix®, Vitafix Ultra (Nuscience), Mycofix®, Mycofix® Secure, FUMzyme, Biomin® BBSH, Biomin® MTV (Biomin), Mold-Nil®, Toxy-Nil® and Unike® Plus (Nutriad).

Methods of Preparing an Animal Feed

In a fifth aspect, the invention relates to a method of preparing the animal feed of the first aspect, comprising the steps of:

(a) mixing an animal feed additive with one or more protein sources and one or more energy sources;

(b) optionally steam treating the animal feed of (a) followed by pressing the steam treated mixture to form pellets; and (c) optionally spraying a liquid formulation onto the animal feed of (a) or (b).

In one embodiment, the polypeptide having muramidase activity and the at least one probiotic is added in step (a). In one embodiment, the polypeptide having muramidase activity is added in step (c) and the at least one probiotic is added in step (a).

In one embodiment, the animal feed is pelleted by steam treating the mixture of (a) to obtain a moisture content below 20% by weight of the mixture, and pressing the steam treated mixture to form pellets. In one embodiment, the animal feed is pelleted by steam treating the mixture of (a) to obtain a moisture content below 20% by weight of the mixture wherein the steam treatment is between 60° C. and 100° C. when measured at the outlet of the conditioner, and pressing the steam treated mixture to form pellets. In one embodiment, the total residence time in step b) is between 1 second and 10 minutes. In one embodiment, the temperature of the pellets after pelleting of the steam treated mixture is between 70° C. and 105° C.

Preferred Embodiments of the Invention

1. An animal feed additive comprising one or more probiotic and one or more fungal polypeptides having muramidase activity.
2. The animal feed of embodiment 1, wherein the polypeptide having muramidase activity is a fungal GH24 muramidase or GH25 muramidase.
3. The animal feed additive of any of embodiments 1 to 2, wherein the probiotic is selected from the group consisting of a *Lactobacillus*, a *Bifidobacterium*, a *Saccharomyces*, an *Enterococcus*, a *Streptococcus*, a *Pediococcus*, a *Leuconostoc*, a *Lactococcus*, an *Oenococcus*, a *Bacillus*, *Carnobacterium, Propionibacterium, Clostridium, Megasphaera* and an *Escherichia* or combinations thereof.
4. The animal feed additive of any of embodiments 1 to 3, wherein the polypeptide having muramidase activity degrades cell wall debris from *Lactobacillus johnsonii*.
5. The animal feed additive of any of embodiments 1 to 4, wherein the polypeptide having muramidase activity is selected from the group consisting of:
   (a) a polypeptide having at least 80%, e.g., at least 85%, at least 90%, at least 95%, or 100% sequence identity to SEQ ID NO: 1;
   (b) a polypeptide having at least 80%, e.g., at least 85%, at least 90%, at least 95%, or 100% sequence identity to SEQ ID NO: 2;
   (c) a polypeptide having at least 80%, e.g., at least 85%, at least 90%, at least 95%, or 100% sequence identity to SEQ ID NO: 3;
   (d) a polypeptide having at least 80%, e.g., at least 85%, at least 90%, at least 95%, or 100% sequence identity to SEQ ID NO: 4;
   (e) a polypeptide having at least 80%, e.g., at least 85%, at least 90%, at least 95%, or 100% sequence identity to SEQ ID NO: 5;
   (f) a polypeptide having at least 80%, e.g., at least 85%, at least 90%, at least 95%, or 100% sequence identity to SEQ ID NO: 6;
   (g) a polypeptide having at least 80%, e.g., at least 85%, at least 90%, at least 95%, or 100% sequence identity to SEQ ID NO: 7;
   (h) a polypeptide having at least 80%, e.g., at least 85%, at least 90%, at least 95%, or 100% sequence identity to SEQ ID NO: 8;
   (i) a polypeptide having at least 80%, e.g., at least 85%, at least 90%, at least 95%, or 100% sequence identity to SEQ ID NO: 9;
   (j) a polypeptide having at least 80%, e.g., at least 85%, at least 90%, at least 95%, or 100% sequence identity to SEQ ID NO: 10;
   (k) a polypeptide having at least 80%, e.g., at least 85%, at least 90%, at least 95%, or 100% sequence identity to SEQ ID NO: 11;
   (l) a polypeptide having at least 80%, e.g., at least 85%, at least 90%, at least 95%, or 100% sequence identity to SEQ ID NO: 12;
   (m) a polypeptide having at least 80%, e.g., at least 85%, at least 90%, at least 95%, or 100% sequence identity to SEQ ID NO: 13;
   (n) a polypeptide having at least 80%, e.g., at least 85%, at least 90%, at least 95%, or 100% sequence identity to SEQ ID NO: 14;

(o) a polypeptide having at least 80%, e.g., at least 85%, at least 90%, at least 95%, or 100% sequence identity to SEQ ID NO: 15;
(p) a polypeptide having at least 80%, e.g., at least 85%, at least 90%, at least 95%, or 100% sequence identity to SEQ ID NO: 16;
(q) a polypeptide having at least 80%, e.g., at least 85%, at least 90%, at least 95%, or 100% sequence identity to SEQ ID NO: 17;
(r) a polypeptide having at least 80%, e.g., at least 85%, at least 90%, at least 95%, or 100% sequence identity to SEQ ID NO: 18;
(s) a polypeptide having at least 80%, e.g., at least 85%, at least 90%, at least 95%, or 100% sequence identity to SEQ ID NO: 19;
(t) a polypeptide having at least 80%, e.g., at least 85%, at least 90%, at least 95%, or 100% sequence identity to SEQ ID NO: 20;
(u) a polypeptide having at least 80%, e.g., at least 85%, at least 90%, at least 95%, or 100% sequence identity to SEQ ID NO: 21;
(v) a polypeptide having at least 80%, e.g., at least 85%, at least 90%, at least 95%, or 100% sequence identity to SEQ ID NO: 22;
(w) a polypeptide having at least 80%, e.g., at least 85%, at least 90%, at least 95%, or 100% sequence identity to SEQ ID NO: 23;
(x) a polypeptide having at least 80%, e.g., at least 85%, at least 90%, at least 95%, or 100% sequence identity to SEQ ID NO: 24;
(y) a polypeptide having at least 80%, e.g., at least 85%, at least 90%, at least 95%, or 100% sequence identity to SEQ ID NO: 25;
(z) a polypeptide having at least 80%, e.g., at least 85%, at least 90%, at least 95%, or 100% sequence identity to SEQ ID NO: 26;
(aa) a polypeptide having at least 80%, e.g., at least 85%, at least 90%, at least 95%, or 100% sequence identity to SEQ ID NO: 27;
(ab) a polypeptide having at least 80%, e.g., at least 85%, at least 90%, at least 95%, or 100% sequence identity to SEQ ID NO: 28;
(ac) a polypeptide having at least 80%, e.g., at least 85%, at least 90%, at least 95%, or 100% sequence identity to SEQ ID NO: 29;
(ad) a polypeptide having at least 80%, e.g., at least 85%, at least 90%, at least 95%, or 100% sequence identity to SEQ ID NO: 30;
(ae) a polypeptide having at least 80%, e.g., at least 85%, at least 90%, at least 95%, or 100% sequence identity to SEQ ID NO: 31;
(af) a polypeptide having at least 80%, e.g., at least 85%, at least 90%, at least 95%, or 100% sequence identity to SEQ ID NO: 32;
(ag) a polypeptide having at least 80%, e.g., at least 85%, at least 90%, at least 95%, or 100% sequence identity to SEQ ID NO: 33;
(ah) a polypeptide having at least 80%, e.g., at least 85%, at least 90%, at least 95%, or 100% sequence identity to SEQ ID NO: 34;
(ai) a polypeptide having at least 80%, e.g., at least 85%, at least 90%, at least 95%, or 100% sequence identity to SEQ ID NO: 35;
(aj) a polypeptide having at least 80%, e.g., at least 85%, at least 90%, at least 95%, or 100% sequence identity to SEQ ID NO: 36;
(ak) a polypeptide having at least 80%, e.g., at least 85%, at least 90%, at least 95%, or 100% sequence identity to SEQ ID NO: 37;
(al) a polypeptide having at least 80%, e.g., at least 85%, at least 90%, at least 95%, or 100% sequence identity to SEQ ID NO: 38;
(am) a polypeptide having at least 80%, e.g., at least 85%, at least 90%, at least 95%, or 100% sequence identity to SEQ ID NO: 39;
(an) a polypeptide having at least 80%, e.g., at least 85%, at least 90%, at least 95%, or 100% sequence identity to SEQ ID NO: 40;
(ao) a polypeptide having at least 80%, e.g., at least 85%, at least 90%, at least 95%, or 100% sequence identity to SEQ ID NO: 41;
(ap) a polypeptide having at least 80%, e.g., at least 85%, at least 90%, at least 95%, or 100% sequence identity to SEQ ID NO: 42;
(aq) a polypeptide having at least 80%, e.g., at least 85%, at least 90%, at least 95%, or 100% sequence identity to SEQ ID NO: 43;
(ar) a polypeptide having at least 80%, e.g., at least 85%, at least 90%, at least 95%, or 100% sequence identity to SEQ ID NO: 44;
(as) a polypeptide having at least 80%, e.g., at least 85%, at least 90%, at least 95%, or 100% sequence identity to SEQ ID NO: 45;
(at) a polypeptide having at least 80%, e.g., at least 85%, at least 90%, at least 95%, or 100% sequence identity to SEQ ID NO: 46;
(au) a polypeptide having at least 80%, e.g., at least 85%, at least 90%, at least 95%, or 100% sequence identity to SEQ ID NO: 47;
(av) a polypeptide having at least 80%, e.g., at least 85%, at least 90%, at least 95%, or 100% sequence identity to SEQ ID NO: 48;
(aw) a polypeptide having at least 80%, e.g., at least 85%, at least 90%, at least 95%, or 100% sequence identity to SEQ ID NO: 49;
(ax) a polypeptide having at least 80%, e.g., at least 85%, at least 90%, at least 95%, or 100% sequence identity to SEQ ID NO: 50;
(ay) a polypeptide having at least 80%, e.g., at least 85%, at least 90%, at least 95%, or 100% sequence identity to SEQ ID NO: 51;
(az) a polypeptide having at least 80%, e.g., at least 85%, at least 90%, at least 95%, or 100% sequence identity to SEQ ID NO: 52;
(ba) a polypeptide having at least 80%, e.g., at least 85%, at least 90%, at least 95%, or 100% sequence identity to SEQ ID NO: 53;
(bb) a polypeptide having at least 80%, e.g., at least 85%, at least 90%, at least 95%, or 100% sequence identity to SEQ ID NO: 54;
(bc) a polypeptide having at least 80%, e.g., at least 85%, at least 90%, at least 95%, or 100% sequence identity to SEQ ID NO: 55;
(bd) a polypeptide having at least 80%, e.g., at least 85%, at least 90%, at least 95%, or 100% sequence identity to SEQ ID NO: 56;
(be) a polypeptide having at least 80%, e.g., at least 85%, at least 90%, at least 95%, or 100% sequence identity to SEQ ID NO: 57;
(bf) a polypeptide having at least 80%, e.g., at least 85%, at least 90%, at least 95%, or 100% sequence identity to SEQ ID NO: 58;

(bg) a polypeptide having at least 80%, e.g., at least 85%, at least 90%, at least 95%, or 100% sequence identity to SEQ ID NO: 59;
(bh) a polypeptide having at least 80%, e.g., at least 85%, at least 90%, at least 95%, or 100% sequence identity to SEQ ID NO: 60;
(bi) a polypeptide having at least 80%, e.g., at least 85%, at least 90%, at least 95%, or 100% sequence identity to SEQ ID NO: 61;
(bj) a polypeptide having at least 80%, e.g., at least 85%, at least 90%, at least 95%, or 100% sequence identity to SEQ ID NO: 62;
(bk) a polypeptide having at least 80%, e.g., at least 85%, at least 90%, at least 95%, or 100% sequence identity to SEQ ID NO: 63;
(bl) a polypeptide having at least 80%, e.g., at least 85%, at least 90%, at least 95%, or 100% sequence identity to SEQ ID NO: 64;
(bm) a polypeptide having at least 80%, e.g., at least 85%, at least 90%, at least 95%, or 100% sequence identity to SEQ ID NO: 65;
(bn) a polypeptide having at least 80%, e.g., at least 85%, at least 90%, at least 95%, or 100% sequence identity to SEQ ID NO: 66;
(bo) a polypeptide having at least 80%, e.g., at least 85%, at least 90%, at least 95%, or 100% sequence identity to SEQ ID NO: 67;
(bp) a polypeptide having at least 80%, e.g., at least 85%, at least 90%, at least 95%, or 100% sequence identity to SEQ ID NO: 68;
(bq) a polypeptide having at least 80%, e.g., at least 85%, at least 90%, at least 95%, or 100% sequence identity to SEQ ID NO: 69;
(br) a polypeptide having at least 80%, e.g., at least 85%, at least 90%, at least 95%, or 100% sequence identity to SEQ ID NO: 70;
(bs) a polypeptide having at least 80%, e.g., at least 85%, at least 90%, at least 95%, or 100% sequence identity to SEQ ID NO: 71;
(bt) a variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, SEQ ID NO:12, SEQ ID NO:13, SEQ ID NO:14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70 or SEQ ID NO: 71 comprising one or more amino acid substitutions (preferably conservative substitutions), and/or one or more amino acid deletions, and/or one or more amino acid insertions or any combination thereof in 1, 2, 3, 4, 5, 6, 7, 8, 9 or 10 positions;

(bu) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) and a N-terminal and/or C-terminal extension of between 1 and 10 amino acids; and (bv) a fragment of a polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) having muramidase activity and having at least 90% of the length of the mature polypeptide.

6. The animal feed additive of any of embodiments 1 to 5, wherein the probiotic is selected from the group consisting of *Bacillus subtilis*, *Bacillus licheniformis*, *Bacillus amyloliquefaciens*, *Bacillus cereus*, *Bacillus pumilus*, *Bacillus polymyxa*, *Bacillus megaterium*, *Bacillus coagulans*, *Bacillus circulans*, *Enterococcus faecium*, *Enterococcus* spp, and *Pediococcus* spp, *Lactobacillus* spp, *Bifidobacterium* spp, *Lactobacillus acidophilus*, *Pediococsus acidilactici*, *Lactococcus lactis*, *Bifidobacterium bifidum*, *Propionibacterium thoenii*, *Lactobacillus farciminus*, *Lactobacillus rhamnosus*, *Clostridium butyricum*, *Bifidobacterium animalis* ssp. *animalis*, *Lactobacillus reuteri*, *Lactobacillus salivarius* ssp. *salivarius*, *Megasphaera elsdenii*, and *Propionibacteria* sp.

7. The animal feed additive of any of embodiments 1 to 5, wherein the probiotic is selected from the group consisting a combination of one or more *Lactobacillus* and one or more *Saccharomyces*, one or more *Lactobacillus* and one or more *Streptococcus*, one or more *Lactobacillus* and one or more *Bacillus*, one or more *Lactobacillus* and one or more *Bifidobacterium*, one or more *Saccharomyces* and one or more *Streptococcus*, one or more *Saccharomyces* and one or more *Bacillus*, one or more *Saccharomyces* and one or more *Bifidobacterium*, one or more *Saccharomyces* and one or more *Bacillus*, one or more *Streptococcus* and one or more *Bifidobacterium*, one or more *Streptococcus* and one or more *Bacillus*, one or more *Bacillus* and one or more *Bifidobacterium*.

8. The animal feed additive of any of embodiments 1 to 7, for adding to a protein source wherein the protein source is selected from the group consisting of soybean, wild soybean, beans, lupin, tepary bean, scarlet runner bean, slimjim bean, lima bean, French bean, Broad bean (fava bean), chickpea, lentil, peanut, Spanish peanut, canola, sunflower seed, cotton seed, rapeseed (oilseed rape) or pea or in a processed form such as soybean meal, full fat soy bean meal, soy protein concentrate (SPC), fermented soybean meal (FSBM), sunflower meal, cotton seed meal, rapeseed meal, fish meal, bone meal, feather meal, whey or any combination thereof.

9. The animal feed additive of any of embodiments 1 to 8, for adding to an energy source wherein the energy source is selected from the group consisting of maize, corn, sorghum, barley, wheat, oats, rice, triticale, rye, beet, sugar beet, spinach, potato, cassava, quinoa, cabbage, switchgrass, millet, pearl millet, foxtail millet or in a processed form such as milled corn, milled maize, potato starch, cassava starch, milled sorghum, milled switchgrass, milled millet, milled foxtail millet, milled pearl millet, or any combination thereof.

10. The animal feed additive of any of embodiments 1 to 9, wherein the animal feed additive further comprises one or more components selected from the list consisting of:
one or more additional enzymes;
one or more microbes;
one or more vitamins;
one or more minerals;
one or more amino acids; and
one or more other feed ingredients.

11. The animal feed additive of any of embodiments 1 to 10, wherein the polypeptide having muramidase activity is formulated as a granule.

12. A method of improving European production efficiency factor (EPEF), body weight gain (BWG) and/or feed conversion ratio (FCR) of a mono-gastric animal comprising:
(a) preparing the animal feed additive of any of embodiments 1 to 11; and
(b) providing the animal feed additive to the mono-gastric animal.

13. Use of at least one probiotic in combination with a polypeptide having muramidase activity in a feed composition for improving feed conversion ratio and/or daily weight gain and/or for the modulation of the gut flora and/or for improving bioavailability of the probiotic, wherein the polypeptide having muramidase activity is a fungal GH24 muramidase or GH25 muramidase and wherein the probiotic is selected from the group consisting of a *Lactobacillus*, a *Bifidobacterium*, a *Saccharomyces*, an *Enterococcus*, a *Streptococcus*, a *Pediococcus*, a *Leuconostoc*, a *Lactococcus*, an *Oenococcus*, a *Bacillus*, *Carnobacterium*, *Propionibacterium*, *Clostridium*, *Megasphaera* and an *Escherichia* or combinations thereof.

14. A feed composition or a premix composition, or a feed additive for animals comprising at least one polypeptide having muramidase activity and at least one probiotic, wherein the polypeptide having muramidase activity is a fungal GH24 muramidase or GH25 muramidase and wherein the probiotic is selected from the group consisting of a *Lactobacillus*, a *Bifidobacterium*, a *Saccharomyces*, an *Enterococcus*, a *Streptococcus*, a *Pediococcus*, a *Leuconostoc*, a *Lactococcus*, an *Oenococcus*, a *Bacillus*, *Carnobacterium*, *Propionibacterium*, *Clostridium*, *Megasphaera* and an *Escherichia* or combinations thereof.

15. An animal feed comprising an animal feed additive, one or more protein sources and one or more energy sources characterised in the animal feed further comprises one or more probiotic and one or more fungal polypeptides having muramidase activity.

16. The animal feed of embodiment 15, or animal feed additive of claim 2, wherein the polypeptide having muramidase activity is a fungal GH24 muramidase or GH25 muramidase.

17. The animal feed of any of embodiments 15 to 16, wherein the probiotic is selected from the group consisting of a *Lactobacillus*, a *Bifidobacterium*, a *Saccharomyces*, an *Enterococcus*, a *Streptococcus*, a *Pediococcus*, a *Leuconostoc*, a *Lactococcus*, an *Oenococcus*, a *Bacillus*, *Carnobacterium*, *Propionibacterium*, *Clostridium*, *Megasphaera* and an *Escherichia* or combinations thereof.

18. The animal feed of any of embodiments 15 to 17, wherein the polypeptide having muramidase activity degrades cell wall debris from *Lactobacillus johnsonii*.

19. The animal feed of any of claims 15 to 18, wherein the polypeptide having muramidase activity is selected from the group consisting of:
(a) a polypeptide having at least 80%, e.g., at least 85%, at least 90%, at least 95%, or 100% sequence identity to SEQ ID NO: 1;
(b) a polypeptide having at least 80%, e.g., at least 85%, at least 90%, at least 95%, or 100% sequence identity to SEQ ID NO: 2;
(c) a polypeptide having at least 80%, e.g., at least 85%, at least 90%, at least 95%, or 100% sequence identity to SEQ ID NO: 3;
(d) a polypeptide having at least 80%, e.g., at least 85%, at least 90%, at least 95%, or 100% sequence identity to SEQ ID NO: 4;
(e) a polypeptide having at least 80%, e.g., at least 85%, at least 90%, at least 95%, or 100% sequence identity to SEQ ID NO: 5;
(f) a polypeptide having at least 80%, e.g., at least 85%, at least 90%, at least 95%, or 100% sequence identity to SEQ ID NO: 6;
(g) a polypeptide having at least 80%, e.g., at least 85%, at least 90%, at least 95%, or 100% sequence identity to SEQ ID NO: 7;
(h) a polypeptide having at least 80%, e.g., at least 85%, at least 90%, at least 95%, or 100% sequence identity to SEQ ID NO: 8;
(i) a polypeptide having at least 80%, e.g., at least 85%, at least 90%, at least 95%, or 100% sequence identity to SEQ ID NO: 9;
(j) a polypeptide having at least 80%, e.g., at least 85%, at least 90%, at least 95%, or 100% sequence identity to SEQ ID NO: 10;
(k) a polypeptide having at least 80%, e.g., at least 85%, at least 90%, at least 95%, or 100% sequence identity to SEQ ID NO: 11;
(l) a polypeptide having at least 80%, e.g., at least 85%, at least 90%, at least 95%, or 100% sequence identity to SEQ ID NO: 12;
(m) a polypeptide having at least 80%, e.g., at least 85%, at least 90%, at least 95%, or 100% sequence identity to SEQ ID NO: 13;
(n) a polypeptide having at least 80%, e.g., at least 85%, at least 90%, at least 95%, or 100% sequence identity to SEQ ID NO: 14;
(o) a polypeptide having at least 80%, e.g., at least 85%, at least 90%, at least 95%, or 100% sequence identity to SEQ ID NO: 15;
(p) a polypeptide having at least 80%, e.g., at least 85%, at least 90%, at least 95%, or 100% sequence identity to SEQ ID NO: 16;
(q) a polypeptide having at least 80%, e.g., at least 85%, at least 90%, at least 95%, or 100% sequence identity to SEQ ID NO: 17;
(r) a polypeptide having at least 80%, e.g., at least 85%, at least 90%, at least 95%, or 100% sequence identity to SEQ ID NO: 18;
(s) a polypeptide having at least 80%, e.g., at least 85%, at least 90%, at least 95%, or 100% sequence identity to SEQ ID NO: 19;
(t) a polypeptide having at least 80%, e.g., at least 85%, at least 90%, at least 95%, or 100% sequence identity to SEQ ID NO: 20;
(u) a polypeptide having at least 80%, e.g., at least 85%, at least 90%, at least 95%, or 100% sequence identity to SEQ ID NO: 21;

(v) a polypeptide having at least 80%, e.g., at least 85%, at least 90%, at least 95%, or 100% sequence identity to SEQ ID NO: 22;
(w) a polypeptide having at least 80%, e.g., at least 85%, at least 90%, at least 95%, or 100% sequence identity to SEQ ID NO: 23;
(x) a polypeptide having at least 80%, e.g., at least 85%, at least 90%, at least 95%, or 100% sequence identity to SEQ ID NO: 24;
(y) a polypeptide having at least 80%, e.g., at least 85%, at least 90%, at least 95%, or 100% sequence identity to SEQ ID NO: 25;
(z) a polypeptide having at least 80%, e.g., at least 85%, at least 90%, at least 95%, or 100% sequence identity to SEQ ID NO: 26;
(aa) a polypeptide having at least 80%, e.g., at least 85%, at least 90%, at least 95%, or 100% sequence identity to SEQ ID NO: 27;
(ab) a polypeptide having at least 80%, e.g., at least 85%, at least 90%, at least 95%, or 100% sequence identity to SEQ ID NO: 28;
(ac) a polypeptide having at least 80%, e.g., at least 85%, at least 90%, at least 95%, or 100% sequence identity to SEQ ID NO: 29;
(ad) a polypeptide having at least 80%, e.g., at least 85%, at least 90%, at least 95%, or 100% sequence identity to SEQ ID NO: 30;
(ae) a polypeptide having at least 80%, e.g., at least 85%, at least 90%, at least 95%, or 100% sequence identity to SEQ ID NO: 31;
(af) a polypeptide having at least 80%, e.g., at least 85%, at least 90%, at least 95%, or 100% sequence identity to SEQ ID NO: 32;
(ag) a polypeptide having at least 80%, e.g., at least 85%, at least 90%, at least 95%, or 100% sequence identity to SEQ ID NO: 33;
(ah) a polypeptide having at least 80%, e.g., at least 85%, at least 90%, at least 95%, or 100% sequence identity to SEQ ID NO: 34;
(ai) a polypeptide having at least 80%, e.g., at least 85%, at least 90%, at least 95%, or 100% sequence identity to SEQ ID NO: 35;
(aj) a polypeptide having at least 80%, e.g., at least 85%, at least 90%, at least 95%, or 100% sequence identity to SEQ ID NO: 36;
(ak) a polypeptide having at least 80%, e.g., at least 85%, at least 90%, at least 95%, or 100% sequence identity to SEQ ID NO: 37;
(al) a polypeptide having at least 80%, e.g., at least 85%, at least 90%, at least 95%, or 100% sequence identity to SEQ ID NO: 38;
(am) a polypeptide having at least 80%, e.g., at least 85%, at least 90%, at least 95%, or 100% sequence identity to SEQ ID NO: 39;
(an) a polypeptide having at least 80%, e.g., at least 85%, at least 90%, at least 95%, or 100% sequence identity to SEQ ID NO: 40;
(ao) a polypeptide having at least 80%, e.g., at least 85%, at least 90%, at least 95%, or 100% sequence identity to SEQ ID NO: 41;
(ap) a polypeptide having at least 80%, e.g., at least 85%, at least 90%, at least 95%, or 100% sequence identity to SEQ ID NO: 42;
(aq) a polypeptide having at least 80%, e.g., at least 85%, at least 90%, at least 95%, or 100% sequence identity to SEQ ID NO: 43;
(ar) a polypeptide having at least 80%, e.g., at least 85%, at least 90%, at least 95%, or 100% sequence identity to SEQ ID NO: 44;
(as) a polypeptide having at least 80%, e.g., at least 85%, at least 90%, at least 95%, or 100% sequence identity to SEQ ID NO: 45;
(at) a polypeptide having at least 80%, e.g., at least 85%, at least 90%, at least 95%, or 100% sequence identity to SEQ ID NO: 46;
(au) a polypeptide having at least 80%, e.g., at least 85%, at least 90%, at least 95%, or 100% sequence identity to SEQ ID NO: 47;
(av) a polypeptide having at least 80%, e.g., at least 85%, at least 90%, at least 95%, or 100% sequence identity to SEQ ID NO: 48;
(aw) a polypeptide having at least 80%, e.g., at least 85%, at least 90%, at least 95%, or 100% sequence identity to SEQ ID NO: 49;
(ax) a polypeptide having at least 80%, e.g., at least 85%, at least 90%, at least 95%, or 100% sequence identity to SEQ ID NO: 50;
(ay) a polypeptide having at least 80%, e.g., at least 85%, at least 90%, at least 95%, or 100% sequence identity to SEQ ID NO: 51;
(az) a polypeptide having at least 80%, e.g., at least 85%, at least 90%, at least 95%, or 100% sequence identity to SEQ ID NO: 52;
(ba) a polypeptide having at least 80%, e.g., at least 85%, at least 90%, at least 95%, or 100% sequence identity to SEQ ID NO: 53;
(bb) a polypeptide having at least 80%, e.g., at least 85%, at least 90%, at least 95%, or 100% sequence identity to SEQ ID NO: 54;
(bc) a polypeptide having at least 80%, e.g., at least 85%, at least 90%, at least 95%, or 100% sequence identity to SEQ ID NO: 55;
(bd) a polypeptide having at least 80%, e.g., at least 85%, at least 90%, at least 95%, or 100% sequence identity to SEQ ID NO: 56;
(be) a polypeptide having at least 80%, e.g., at least 85%, at least 90%, at least 95%, or 100% sequence identity to SEQ ID NO: 57;
(bf) a polypeptide having at least 80%, e.g., at least 85%, at least 90%, at least 95%, or 100% sequence identity to SEQ ID NO: 58;
(bg) a polypeptide having at least 80%, e.g., at least 85%, at least 90%, at least 95%, or 100% sequence identity to SEQ ID NO: 59;
(bh) a polypeptide having at least 80%, e.g., at least 85%, at least 90%, at least 95%, or 100% sequence identity to SEQ ID NO: 60;
(bi) a polypeptide having at least 80%, e.g., at least 85%, at least 90%, at least 95%, or 100% sequence identity to SEQ ID NO: 61;
(bj) a polypeptide having at least 80%, e.g., at least 85%, at least 90%, at least 95%, or 100% sequence identity to SEQ ID NO: 62;
(bk) a polypeptide having at least 80%, e.g., at least 85%, at least 90%, at least 95%, or 100% sequence identity to SEQ ID NO: 63;
(bl) a polypeptide having at least 80%, e.g., at least 85%, at least 90%, at least 95%, or 100% sequence identity to SEQ ID NO: 64;
(bm) a polypeptide having at least 80%, e.g., at least 85%, at least 90%, at least 95%, or 100% sequence identity to SEQ ID NO: 65;

(bn) a polypeptide having at least 80%, e.g., at least 85%, at least 90%, at least 95%, or 100% sequence identity to SEQ ID NO: 66;
(bo) a polypeptide having at least 80%, e.g., at least 85%, at least 90%, at least 95%, or 100% sequence identity to SEQ ID NO: 67;
(bp) a polypeptide having at least 80%, e.g., at least 85%, at least 90%, at least 95%, or 100% sequence identity to SEQ ID NO: 68;
(bq) a polypeptide having at least 80%, e.g., at least 85%, at least 90%, at least 95%, or 100% sequence identity to SEQ ID NO: 69;
(br) a polypeptide having at least 80%, e.g., at least 85%, at least 90%, at least 95%, or 100% sequence identity to SEQ ID NO: 70;
(bs) a polypeptide having at least 80%, e.g., at least 85%, at least 90%, at least 95%, or 100% sequence identity to SEQ ID NO: 71;
(bt) a variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO:10, SEQ ID NO:11, SEQ ID NO:12, SEQ ID NO:13, SEQ ID NO:14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70 or SEQ ID NO: 71 comprising one or more amino acid substitutions (preferably conservative substitutions), and/or one or more amino acid deletions, and/or one or more amino acid insertions or any combination thereof in 1, 2, 3, 4, 5, 6, 7, 8, 9 or 10 positions;
(bu) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) and a N-terminal and/or C-terminal extension of between 1 and 10 amino acids; and
(bv) a fragment of a polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) having muramidase activity and having at least 90% of the length of the mature polypeptide.

1. The animal feed of any of embodiments 15 to 19, wherein the probiotic is selected from the group consisting of *Bacillus subtilis*, *Bacillus licheniformis*, *Bacillus amyloliquefaciens*, *Bacillus cereus*, *Bacillus pumilus*, *Bacillus polymyxa*, *Bacillus megaterium*, *Bacillus coagulans*, *Bacillus circulans*, *Enterococcus faecium*, *Enterococcus* spp, and *Pediococcus* spp, *Lactobacillus* spp, *Bifidobacterium* spp, *Lactobacillus acidophilus*, *Pediocosus acidilactici*, *Lactococcus lactis*, *Bifidobacterium bifidum*, *Propionibacterium thoenii*, *Lactobacillus farciminus*, *Lactobacillus rhamnosus*, *Clostridium butyricum*, *Bifidobacterium animalis* ssp. *animalis*, *Lactobacillus reuteri*, *Lactobacillus salivarius* ssp. *salivarius*, *Megasphaera elsdenii*, and *Propionibacteria* sp.

2. The animal feed of any of embodiments 15 to 20, wherein the probiotic is selected from the group consisting a combination of one or more *Lactobacillus* and one or more *Saccharomyces*, one or more *Lactobacillus* and one or more *Streptococcus*, one or more *Lactobacillus* and one or more *Bacillus*, one or more *Lactobacillus* and one or more *Bifidobacterium*, one or more *Saccharomyces* and one or more *Streptococcus*, one or more *Saccharomyces* and one or more *Bacillus*, one or more *Saccharomyces* and one or more *Bifidobacterium*, one or more *Saccharomyces* and one or more *Bacillus*, one or more *Streptococcus* and one or more *Bifidobacterium*, one or more *Streptococcus* and one or more *Bacillus*, one or more *Bacillus* and one or more *Bifidobacterium*.

3. The animal feed of any of embodiments 15 to 21, wherein the protein source is selected from the group consisting of soybean, wild soybean, beans, lupin, tepary bean, scarlet runner bean, slimjim bean, lima bean, French bean, Broad bean (fava bean), chickpea, lentil, peanut, Spanish peanut, canola, sunflower seed, cotton seed, rapeseed (oilseed rape) or pea or in a processed form such as soybean meal, full fat soy bean meal, soy protein concentrate (SPC), fermented soybean meal (FSBM), sunflower meal, cotton seed meal, rapeseed meal, fish meal, bone meal, feather meal, whey or any combination thereof.

4. The animal feed of any of embodiments 15 to 22, wherein the energy source is selected from the group consisting of maize, corn, sorghum, barley, wheat, oats, rice, triticale, rye, beet, sugar beet, spinach, potato, cassava, quinoa, cabbage, switchgrass, millet, pearl millet, foxtail millet or in a processed form such as milled corn, milled maize, potato starch, cassava starch, milled sorghum, milled switchgrass, milled millet, milled foxtail millet, milled pearl millet, or any combination thereof.

5. The animal feed of any of embodiments 15 to 23, wherein the animal feed additive further comprises one or more components selected from the list consisting of:
one or more additional enzymes;
one or more microbes;
one or more vitamins;
one or more minerals;
one or more amino acids; and
one or more other feed ingredients.

1. The animal feed of any of embodiments 15 to 24, wherein the polypeptide having muramidase activity is formulated as a granule.

2. A method of improving European production efficiency factor (EPEF), body weight gain (BWG) and/or feed conversion ratio (FCR) of a mono-gastric animal comprising:
(a) preparing the animal feed of any of embodiments 15 to 25; and
(b) providing the animal feed to the mono-gastric animal.

1. Use of at least one probiotic in combination with a polypeptide having muramidase activity in a feed composition for improving feed conversion ratio and/or daily weight gain and/or for the modulation of the gut flora and/or for improving bioavailability of the probiotic, wherein the polypeptide having muramidase activity is a fungal GH24 muramidase or GH25 muramidase and wherein the probiotic is selected from the group consisting of a *Lactobacillus*, a *Bifidobacterium*, a *Saccharomyces*, an *Enterococcus*, a *Streptococcus*, a *Pediococcus*, a *Leuconostoc*, a *Lactococcus*, an *Oenococcus*, a *Bacillus*, *Carnobacterium*, *Propionibacterium*, *Clostridium*, *Megasphaera* and an *Escherichia* or combinations thereof.
2. A feed composition or a premix composition, or a feed additive for animals comprising at least one polypeptide having muramidase activity and at least one probiotic, wherein the polypeptide having muramidase activity is a fungal GH24 muramidase or GH25 muramidase and wherein the probiotic is selected from the group consisting of a *Lactobacillus*, a *Bifidobacterium*, a *Saccharomyces*, an *Enterococcus*, a *Streptococcus*, a *Pediococcus*, a *Leuconostoc*, a *Lactococcus*, an *Oenococcus*, a *Bacillus*, *Carnobacterium*, *Propionibacterium*, *Clostridium*, *Megasphaera* and an *Escherichia* or combinations thereof.
3. The animal feed additive of any of embodiments 1 to 10, wherein the polypeptide having muramidase activity is selected from the group consisting of a polypeptide having at least 85% sequence identity to SEQ ID NO:1 and a polypeptide having at least 85% sequence identity to SEQ ID NO:2, such as selected from the group consisting of a polypeptide having at least 90% sequence identity to SEQ ID NO:1 and a polypeptide having at least 90% sequence identity to SEQ ID NO:2, such as selected from the group consisting of a polypeptide having at least 95% sequence identity to SEQ ID NO:1 and a polypeptide having at least 95% sequence identity to SEQ ID NO:2, such as selected from the group consisting of a polypeptide having at least 98% sequence identity to SEQ ID NO:1 and a polypeptide having at least 98% sequence identity to SEQ ID NO:2, such as selected from the group consisting of a polypeptide having at least 99% sequence identity to SEQ ID NO:1 and a polypeptide having at least 99% sequence identity to SEQ ID NO:2.
4. The animal feed of any of embodiments 15 to 24, wherein the polypeptide having muramidase activity is selected from the group consisting of a polypeptide having at least 85% sequence identity to SEQ ID NO:1 and a polypeptide having at least 85% sequence identity to SEQ ID NO:2, such as selected from the group consisting of a polypeptide having at least 90% sequence identity to SEQ ID NO:1 and a polypeptide having at least 90% sequence identity to SEQ ID NO:2, such as selected from the group consisting of a polypeptide having at least 95% sequence identity to SEQ ID NO:1 and a polypeptide having at least 95% sequence identity to SEQ ID NO:2, such as selected from the group consisting of a polypeptide having at least 98% sequence identity to SEQ ID NO:1 and a polypeptide having at least 98% sequence identity to SEQ ID NO:2, such as selected from the group consisting of a polypeptide having at least 99% sequence identity to SEQ ID NO:1 and a polypeptide having at least 99% sequence identity to SEQ ID NO:2.
5.

EXAMPLES

Example 1: Determination of Muramidase Activity

The activity of muramidase was determined by measuring the decrease (drop) in absorbance/optical density of a solution of suspended *Micrococcus lysodeikticus* ATTC No. 4698 (Sigma-Aldrich M3770) measured in a microplate reader (Tecan Infinite M200) at 450 nm.

Preparation of *Micrococcus lysodeikticus* Substrate

Before use the cells were suspended in deionized water to a concentration of 10 mg cells/mL and the absorbance/optical density (OD) at 450 nm was measured. The cell suspension was then adjusted so that the cell concentration in the turbidity assay (180 μL buffer+20 μL sample+20 μL substrate) equaled an OD450=1 0.0. The adjusted cell suspension was then stored at ambient temperature before use. Suspended cells were used within 3 hours.

Preparation of Citric Acid—Phosphate Buffer pH 4

61.45 mL 0.1 M citric acid was mixed with 38.55 mL 0.2 M disodium hydrogen phosphate, and the pH was adjusted with hydrochloric acid or sodium hydroxide to pH 4.

Measurement of Muramidase Antimicrobial Activity in the Turbidity Assay

The muramidase sample to be measured was diluted to a concentration of 50 mg enzyme protein/L in deionized water, and kept on ice until use. In a 96 well microtiter plate (Nunc) 180 μL citric acid—phosphate buffer pH 4 and 20 μL of the diluted muramidase sample was added and kept cold (5° C.). To start the activity measurement 20 μL of the substrate (*Micrococcus lysodeikticus*) was added to each well, and kinetic measurement of absorbance at 450 nm was initiated for 1 hour at 37° C. in a microplate reader. The measured absorbance at 450 nm was monitored for each well and over time a drop in absorbance was seen if the muramidase has muramidase activity.

Following incubation, the muramidase activity against *Micrococcus lysodeikticus* was determined as Δ absorbance at 450 nm (start value–end value) of each well after 1 hour. Significance was calculated using Dunnett's with control test p level 0.05 in JMP® version 12.1.0 statistical software package from SAS Institute Inc.

Example 2: Cloning, Expression and Purification of the Muramidases

The GH25 muramidases of SEQ ID NO: 1 to SEQ ID NO: 2 were cloned and expressed as described in example 2 of WO 2013/076253. The GH25 muramidase of SEQ ID NO: 3 may be cloned using basic molecular techniques (Ausubel et al., 2003, Curr. Prot. Mol. Biol., John Wiley & Sons, Cambridge, USA; Christgau et al. 1995, Curr. Genet. 27, 135-141). The GH25 muramidase of SEQ ID NO: 4 may be cloned and expressed as described in WO2009/102755. The GH25 muramidase of SEQ ID NO: 5 was cloned and expressed as described in WO2005/080559. The GH25 muramidases of SEQ ID NO: 6 to SEQ ID NO: 59 were cloned and expressed as described in PCT/CN2017/075978. The GH25 muramidases of SEQ ID NO: 60 to SEQ ID NO: 62 were cloned and expressed as described in PCT/CN2017/075960. The GH24 muramidases of SEQ ID NO: 63 to SEQ ID NO: 71 were cloned and expressed as described in WO2017/000922.

Example 3: Digestibility Study

Energy digestibility (AME) is significantly increased from the level of the negative control when Balancius™ supplements a probiotic-comprising animal feed diets in diets comprising any one of Cylactin® (DSM Nutritional Products), Alterion (Adisseo), Enviva PRO (DuPont Animal Nutrition), and GalliproMax®. When any of the DFMs are supplemented with Balancius™, there is a significant increase in AME greater than the sum of the increase from the muramidase or either of the DFMs alone.

---

What is claimed is:

1. An animal feed or animal feed additive comprising a probiotic and a polypeptide having GH24 muramidase activity and/or GH25 muramidase activity, said probiotic comprising one or more *Bacillus*, one or more *Lactobacillus*, and/or one or more *Clostridium*.

2. The animal feed or animal feed additive of claim 1, wherein the polypeptide is a fungal GH24 muramidase or GH25 muramidase.

3. The animal feed or animal feed additive of claim 1, wherein the probiotic comprises one or more *Lactobacillus*, and/or one or more *Bacillus*.

4. The animal feed or animal feed additive of claim 1, wherein the polypeptide having GH24 muramidase activity and/or GH25 muramidase activity degrades cell wall debris from *Lactobacillus johnsonii*.

5. The animal feed or animal feed additive of claim 1, wherein the polypeptide having GH24 muramidase activity and/or GH25 muramidase activity is selected from the group consisting of:
   (a) a polypeptide having at least 80% sequence identity to SEQ ID NO: 1;
   (b) a polypeptide having at least 80% sequence identity to SEQ ID NO: 2;
   (c) a polypeptide having at least 80% sequence identity to SEQ ID NO: 3;
   (d) a polypeptide having at least 80% sequence identity to SEQ ID NO: 4;
   (e) a polypeptide having at least 80% sequence identity to SEQ ID NO: 5;
   (f) a polypeptide having at least 80% sequence identity to SEQ ID NO: 6;
   (g) a polypeptide having at least 80% sequence identity to SEQ ID NO: 7;
   (h) a polypeptide having at least 80% sequence identity to SEQ ID NO: 8;
   (i) a polypeptide having at least 80% sequence identity to SEQ ID NO: 9;
   (j) a polypeptide having at least 80% sequence identity to SEQ ID NO: 10;
   (k) a polypeptide having at least 80% sequence identity to SEQ ID NO: 11;
   (l) a polypeptide having at least 80% sequence identity to SEQ ID NO: 12;
   (m) a polypeptide having at least 80% sequence identity to SEQ ID NO: 13;
   (n) a polypeptide having at least 80% sequence identity to SEQ ID NO: 14;
   (o) a polypeptide having at least 80% sequence identity to SEQ ID NO: 15;
   (p) a polypeptide having at least 80% sequence identity to SEQ ID NO: 16;
   (q) a polypeptide having at least 80% sequence identity to SEQ ID NO: 17;
   (r) a polypeptide having at least 80% sequence identity to SEQ ID NO: 18;
   (s) a polypeptide having at least 80% sequence identity to SEQ ID NO: 19;
   (t) a polypeptide having at least 80% sequence identity to SEQ ID NO: 20;
   (u) a polypeptide having at least 80% sequence identity to SEQ ID NO: 21;
   (v) a polypeptide having at least 80% sequence identity to SEQ ID NO: 22;
   (w) a polypeptide having at least 80% sequence identity to SEQ ID NO: 23;
   (x) a polypeptide having at least 80% sequence identity to SEQ ID NO: 24;
   (y) a polypeptide having at least 80% sequence identity to SEQ ID NO: 25;
   (z) a polypeptide having at least 80% sequence identity to SEQ ID NO: 26;
   (aa) a polypeptide having at least 80% sequence identity to SEQ ID NO: 27;
   (ab) a polypeptide having at least 80% sequence identity to SEQ ID NO: 28;
   (ac) a polypeptide having at least 80% sequence identity to SEQ ID NO: 29;
   (ad) a polypeptide having at least 80% sequence identity to SEQ ID NO: 30;
   (ae) a polypeptide having at least 80% sequence identity to SEQ ID NO: 31;
   (af) a polypeptide having at least 80% sequence identity to SEQ ID NO: 32;
   (ag) a polypeptide having at least 80% sequence identity to SEQ ID NO: 33;
   (ah) a polypeptide having at least 80% sequence identity to SEQ ID NO: 34;
   (ai) a polypeptide having at least 80% sequence identity to SEQ ID NO: 35;
   (aj) a polypeptide having at least 80% sequence identity to SEQ ID NO: 36;
   (ak) a polypeptide having at least 80% sequence identity to SEQ ID NO: 37;
   (al) a polypeptide having at least 80% sequence identity to SEQ ID NO: 38;
   (am) a polypeptide having at least 80% sequence identity to SEQ ID NO: 39;
   (an) a polypeptide having at least 80% sequence identity to SEQ ID NO: 40;

(ao) a polypeptide having at least 80% sequence identity to SEQ ID NO: 41;
(ap) a polypeptide having at least 80% sequence identity to SEQ ID NO: 42;
(aq) a polypeptide having at least 80% sequence identity to SEQ ID NO: 43;
(ar) a polypeptide having at least 80% sequence identity to SEQ ID NO: 44;
(as) a polypeptide having at least 80% sequence identity to SEQ ID NO: 45;
(at) a polypeptide having at least 80% sequence identity to SEQ ID NO: 46;
(au) a polypeptide having at least 80% sequence identity to SEQ ID NO: 47;
(av) a polypeptide having at least 80% sequence identity to SEQ ID NO: 48;
(aw) a polypeptide having at least 80% sequence identity to SEQ ID NO: 49;
(ax) a polypeptide having at least 80% sequence identity to SEQ ID NO: 50;
(ay) a polypeptide having at least 80% sequence identity to SEQ ID NO: 51;
(az) a polypeptide having at least 80% sequence identity to SEQ ID NO: 52;
(ba) a polypeptide having at least 80% sequence identity to SEQ ID NO: 53;
(bb) a polypeptide having at least 80% sequence identity to SEQ ID NO: 54;
(bc) a polypeptide having at least 80% sequence identity to SEQ ID NO: 55;
(bd) a polypeptide having at least 80% sequence identity to SEQ ID NO: 56;
(be) a polypeptide having at least 80% sequence identity to SEQ ID NO: 57;
(bf) a polypeptide having at least 80% sequence identity to SEQ ID NO: 58;
(bg) a polypeptide having at least 80% sequence identity to SEQ ID NO: 59;
(bh) a polypeptide having at least 80% sequence identity to SEQ ID NO: 60;
(bi) a polypeptide having at least 80% sequence identity to SEQ ID NO: 61;
(bj) a polypeptide having at least 80% sequence identity to SEQ ID NO: 62;
(bk) a polypeptide having at least 80% sequence identity to SEQ ID NO: 63;
(bl) a polypeptide having at least 80% sequence identity to SEQ ID NO: 64;
(bm) a polypeptide having at least 80% sequence identity to SEQ ID NO: 65;
(bn) a polypeptide having at least 80% sequence identity to SEQ ID NO: 66;
(bo) a polypeptide having at least 80% sequence identity to SEQ ID NO: 67;
(bp) a polypeptide having at least 80% sequence identity to SEQ ID NO: 68;
(bq) a polypeptide having at least 80% sequence identity to SEQ ID NO: 69;
(br) a polypeptide having at least 80% sequence identity to SEQ ID NO: 70;
(bs) a polypeptide having at least 80% sequence identity to SEQ ID NO: 71;
(bt) a variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70 or SEQ ID NO: 71 comprising one or more amino acid substitutions, and/or one or more amino acid deletions, and/or one or more amino acid insertions or any combination thereof in 1, 2, 3, 4, 5, 6, 7, 8, 9 or 10 positions;
(bu) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) and a N-terminal and/or C-terminal extension of between 1 and 10 amino acids; and
(bv) a fragment of a polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) having muramidase activity and having at least 90% of the length of the mature polypeptide.

6. The animal feed or animal feed additive of claim 1, wherein the probiotic comprises one or more *Bacillus subtilis*, *Bacillus licheniformis*, *Bacillus amyloliquefaciens*, *Bacillus cereus*, *Bacillus pumilus*, *Bacillus polymyxa*, *Bacillus megaterium*, *Bacillus coagulans*, *Bacillus circulans*, *Lactobacillus farciminus*, *Lactobacillus rhamnosus*, *Clostridium butyricum*, *Lactobacillus reuteri*, and/or *Lactobacillus salivarius* ssp. *salivarius*.

7. The animal feed or animal feed additive of claim 1, wherein the probiotic is selected from the group consisting of a combination of one or more *Lactobacillus* and one or more *Saccharomyces*, one or more *Lactobacillus* and one or more *Streptococcus*, one or more *Lactobacillus* and one or more *Bacillus*, one or more *Lactobacillus* and one or more *Bifidobacterium*, one or more *Saccharomyces* and one or more *Bacillus*, one or more *Saccharomyces* and one or more *Bacillus*, one or more *Streptococcus* and one or more *Bacillus*, one or more *Bacillus* and one or more *Bifidobacterium*.

8. The animal feed or animal feed additive of claim 1, further comprising a protein source selected from the group consisting of soybean, wild soybean, beans, lupin, tepary bean, scarlet runner bean, slimjim bean, lima bean, French bean, Broad bean (fava bean), chickpea, lentil, peanut, Spanish peanut, canola, sunflower seed, cotton seed, rapeseed (oilseed rape) or pea or in a processed form such as soybean meal, full fat soy bean meal, soy protein concentrate (SPC), fermented soybean meal (FSBM), sunflower meal, cotton seed meal, rapeseed meal, fish meal, bone meal, feather meal, whey or any combination thereof.

9. The animal feed or animal feed additive of claim 1, further comprising an energy source selected from the group consisting of maize, corn, sorghum, barley, wheat, oats, rice, triticale, rye, beet, sugar beet, spinach, potato, cassava, *quinoa*, cabbage, switchgrass, millet, pearl millet, foxtail millet or in a processed form such as milled corn, milled maize, potato starch, cassava starch, milled sorghum, milled switchgrass, milled millet, milled foxtail millet, milled pearl millet, or any combination thereof.

10. The animal feed or animal feed additive of claim 1, further comprising one or more components selected from the list consisting of:
   one or more additional enzymes;
   one or more microbes;
   one or more vitamins;
   one or more minerals;
   one or more amino acids; and
   one or more other feed ingredients.

11. The animal feed or animal feed additive of claim 1, wherein the polypeptide having GH24 muramidase activity and/or GH25 muramidase activity is formulated as a granule.

12. A method of improving European production efficiency factor (EPEF), body weight gain (BWG) and/or feed conversion ratio (FCR) of a mono-gastric animal comprising feeding the animal feed or animal feed additive of claim 1 to said mono-gastric animal.

13. An animal feed or animal feed additive comprising one or more fungal polypeptides having GH24 muramidase activity and/or GH25 muramidase activity and one or more probiotics selected from *Lactobacillus, Bacillus, Clostridium*, and combinations thereof.

14. The animal feed or animal feed additive of claim 13, wherein the probiotic comprises one or more *Bacillus*.

15. The animal feed or animal feed additive of claim 13, wherein the probiotic comprises one or more *Lactobacillus*.

16. The animal feed or animal feed additive of claim 13, wherein the polypeptide having GH24 muramidase activity and/or GH25 muramidase activity is selected from the group consisting of:
   (a) a polypeptide having at least 80% sequence identity to SEQ ID NO: 1;
   (b) a polypeptide having at least 80% sequence identity to SEQ ID NO: 2;
   (c) a polypeptide having at least 80% sequence identity to SEQ ID NO: 3;
   (d) a polypeptide having at least 80% sequence identity to SEQ ID NO: 4;
   (e) a polypeptide having at least 80% sequence identity to SEQ ID NO: 5;
   (f) a polypeptide having at least 80% sequence identity to SEQ ID NO: 6;
   (g) a polypeptide having at least 80% sequence identity to SEQ ID NO: 7;
   (h) a polypeptide having at least 80% sequence identity to SEQ ID NO: 8;
   (i) a polypeptide having at least 80% sequence identity to SEQ ID NO: 9;
   (j) a polypeptide having at least 80% sequence identity to SEQ ID NO: 10;
   (k) a polypeptide having at least 80% sequence identity to SEQ ID NO: 11;
   (l) a polypeptide having at least 80% sequence identity to SEQ ID NO: 12;
   (m) a polypeptide having at least 80% sequence identity to SEQ ID NO: 13;
   (n) a polypeptide having at least 80% sequence identity to SEQ ID NO: 14;
   (o) a polypeptide having at least 80% sequence identity to SEQ ID NO: 15;
   (p) a polypeptide having at least 80% sequence identity to SEQ ID NO: 16;
   (q) a polypeptide having at least 80% sequence identity to SEQ ID NO: 17;
   (r) a polypeptide having at least 80% sequence identity to SEQ ID NO: 18;
   (s) a polypeptide having at least 80% sequence identity to SEQ ID NO: 19;
   (t) a polypeptide having at least 80% sequence identity to SEQ ID NO: 20;
   (u) a polypeptide having at least 80% sequence identity to SEQ ID NO: 21;
   (v) a polypeptide having at least 80% sequence identity to SEQ ID NO: 22;
   (w) a polypeptide having at least 80% sequence identity to SEQ ID NO: 23;
   (x) a polypeptide having at least 80% sequence identity to SEQ ID NO: 24;
   (y) a polypeptide having at least 80% sequence identity to SEQ ID NO: 25;
   (z) a polypeptide having at least 80% sequence identity to SEQ ID NO: 26;
   (aa) a polypeptide having at least 80% sequence identity to SEQ ID NO: 27;
   (ab) a polypeptide having at least 80% sequence identity to SEQ ID NO: 28;
   (ac) a polypeptide having at least 80% sequence identity to SEQ ID NO: 29;
   (ad) a polypeptide having at least 80% sequence identity to SEQ ID NO: 30;
   (ae) a polypeptide having at least 80% sequence identity to SEQ ID NO: 31;
   (af) a polypeptide having at least 80% sequence identity to SEQ ID NO: 32;
   (ag) a polypeptide having at least 80% sequence identity to SEQ ID NO: 33;
   (ah) a polypeptide having at least 80% sequence identity to SEQ ID NO: 34;
   (ai) a polypeptide having at least 80% sequence identity to SEQ ID NO: 35;
   (aj) a polypeptide having at least 80% sequence identity to SEQ ID NO: 36;
   (ak) a polypeptide having at least 80% sequence identity to SEQ ID NO: 37;
   (al) a polypeptide having at least 80% sequence identity to SEQ ID NO: 38;
   (am) a polypeptide having at least 80% sequence identity to SEQ ID NO: 39;
   (an) a polypeptide having at least 80% sequence identity to SEQ ID NO: 40;
   (ao) a polypeptide having at least 80% sequence identity to SEQ ID NO: 41;
   (ap) a polypeptide having at least 80% sequence identity to SEQ ID NO: 42;
   (aq) a polypeptide having at least 80% sequence identity to SEQ ID NO: 43;
   (ar) a polypeptide having at least 80% sequence identity to SEQ ID NO: 44;
   (as) a polypeptide having at least 80% sequence identity to SEQ ID NO: 45;

(at) a polypeptide having at least 80% sequence identity to SEQ ID NO: 46;
(au) a polypeptide having at least 80% sequence identity to SEQ ID NO: 47;
(av) a polypeptide having at least 80% sequence identity to SEQ ID NO: 48;
(aw) a polypeptide having at least 80% sequence identity to SEQ ID NO: 49;
(ax) a polypeptide having at least 80% sequence identity to SEQ ID NO: 50;
(ay) a polypeptide having at least 80% sequence identity to SEQ ID NO: 51;
(az) a polypeptide having at least 80% sequence identity to SEQ ID NO: 52;
(ba) a polypeptide having at least 80% sequence identity to SEQ ID NO: 53;
(bb) a polypeptide having at least 80% sequence identity to SEQ ID NO: 54;
(bc) a polypeptide having at least 80% sequence identity to SEQ ID NO: 55;
(bd) a polypeptide having at least 80% sequence identity to SEQ ID NO: 56;
(be) a polypeptide having at least 80% sequence identity to SEQ ID NO: 57;
(bf) a polypeptide having at least 80% sequence identity to SEQ ID NO: 58;
(bg) a polypeptide having at least 80% sequence identity to SEQ ID NO: 59;
(bh) a polypeptide having at least 80% sequence identity to SEQ ID NO: 60;
(bi) a polypeptide having at least 80% sequence identity to SEQ ID NO: 61;
(bj) a polypeptide having at least 80% sequence identity to SEQ ID NO: 62;
(bk) a polypeptide having at least 80% sequence identity to SEQ ID NO: 63;
(bl) a polypeptide having at least 80% sequence identity to SEQ ID NO: 64;
(bm) a polypeptide having at least 80% sequence identity to SEQ ID NO: 65;
(bn) a polypeptide having at least 80% sequence identity to SEQ ID NO: 66;
(bo) a polypeptide having at least 80% sequence identity to SEQ ID NO: 67;
(bp) a polypeptide having at least 80% sequence identity to SEQ ID NO: 68;
(bq) a polypeptide having at least 80% sequence identity to SEQ ID NO: 69;
(br) a polypeptide having at least 80% sequence identity to SEQ ID NO: 70;
(bs) a polypeptide having at least 80% sequence identity to SEQ ID NO: 71;
(bt) a variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70 or SEQ ID NO: 71 comprising one or more amino acid substitutions, and/or one or more amino acid deletions, and/or one or more amino acid insertions or any combination thereof in 1, 2, 3, 4, 5, 6, 7, 8, 9 or 10 positions;
(bu) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) and a N-terminal and/or C-terminal extension of between 1 and 10 amino acids; and
(bv) a fragment of a polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) having muramidase activity and having at least 90% of the length of the mature polypeptide.

17. The animal feed or animal feed additive of claim 13, wherein the polypeptide having GH24 muramidase activity and/or GH25 muramidase activity is selected from the group consisting of:
(a) a polypeptide having at least 90% sequence identity to SEQ ID NO: 1;
(b) a polypeptide having at least 90% sequence identity to SEQ ID NO: 2;
(c) a polypeptide having at least 90% sequence identity to SEQ ID NO: 3;
(d) a polypeptide having at least 90% sequence identity to SEQ ID NO: 4;
(e) a polypeptide having at least 90% sequence identity to SEQ ID NO: 5;
(f) a polypeptide having at least 90% sequence identity to SEQ ID NO: 6;
(g) a polypeptide having at least 90% sequence identity to SEQ ID NO: 7;
(h) a polypeptide having at least 90% sequence identity to SEQ ID NO: 8;
(i) a polypeptide having at least 90% sequence identity to SEQ ID NO: 9;
(j) a polypeptide having at least 90% sequence identity to SEQ ID NO: 10;
(k) a polypeptide having at least 90% sequence identity to SEQ ID NO: 11;
(l) a polypeptide having at least 90% sequence identity to SEQ ID NO: 12;
(m) a polypeptide having at least 90% sequence identity to SEQ ID NO: 13;
(n) a polypeptide having at least 90% sequence identity to SEQ ID NO: 14;
(o) a polypeptide having at least 90% sequence identity to SEQ ID NO: 15;
(p) a polypeptide having at least 90% sequence identity to SEQ ID NO: 16;

(q) a polypeptide having at least 90% sequence identity to SEQ ID NO: 17;
(r) a polypeptide having at least 90% sequence identity to SEQ ID NO: 18;
(s) a polypeptide having at least 90% sequence identity to SEQ ID NO: 19;
(t) a polypeptide having at least 90% sequence identity to SEQ ID NO: 20;
(u) a polypeptide having at least 90% sequence identity to SEQ ID NO: 21;
(v) a polypeptide having at least 90% sequence identity to SEQ ID NO: 22;
(w) a polypeptide having at least 90% sequence identity to SEQ ID NO: 23;
(x) a polypeptide having at least 90% sequence identity to SEQ ID NO: 24;
(y) a polypeptide having at least 90% sequence identity to SEQ ID NO: 25;
(z) a polypeptide having at least 90% sequence identity to SEQ ID NO: 26;
(aa) a polypeptide having at least 90% sequence identity to SEQ ID NO: 27;
(ab) a polypeptide having at least 90% sequence identity to SEQ ID NO: 28;
(ac) a polypeptide having at least 90% sequence identity to SEQ ID NO: 29;
(ad) a polypeptide having at least 90% sequence identity to SEQ ID NO: 30;
(ae) a polypeptide having at least 90% sequence identity to SEQ ID NO: 31;
(af) a polypeptide having at least 90% sequence identity to SEQ ID NO: 32;
(ag) a polypeptide having at least 90% sequence identity to SEQ ID NO: 33;
(ah) a polypeptide having at least 90% sequence identity to SEQ ID NO: 34;
(ai) a polypeptide having at least 90% sequence identity to SEQ ID NO: 35;
(aj) a polypeptide having at least 90% sequence identity to SEQ ID NO: 36;
(ak) a polypeptide having at least 90% sequence identity to SEQ ID NO: 37;
(al) a polypeptide having at least 90% sequence identity to SEQ ID NO: 38;
(am) a polypeptide having at least 90% sequence identity to SEQ ID NO: 39;
(an) a polypeptide having at least 90% sequence identity to SEQ ID NO: 40;
(ao) a polypeptide having at least 90% sequence identity to SEQ ID NO: 41;
(ap) a polypeptide having at least 90% sequence identity to SEQ ID NO: 42;
(aq) a polypeptide having at least 90% sequence identity to SEQ ID NO: 43;
(ar) a polypeptide having at least 90% sequence identity to SEQ ID NO: 44;
(as) a polypeptide having at least 90% sequence identity to SEQ ID NO: 45;
(at) a polypeptide having at least 90% sequence identity to SEQ ID NO: 46;
(au) a polypeptide having at least 90% sequence identity to SEQ ID NO: 47;
(av) a polypeptide having at least 90% sequence identity to SEQ ID NO: 48;
(aw) a polypeptide having at least 90% sequence identity to SEQ ID NO: 49;
(ax) a polypeptide having at least 90% sequence identity to SEQ ID NO: 50;
(ay) a polypeptide having at least 90% sequence identity to SEQ ID NO: 51;
(az) a polypeptide having at least 90% sequence identity to SEQ ID NO: 52;
(ba) a polypeptide having at least 90% sequence identity to SEQ ID NO: 53;
(bb) a polypeptide having at least 90% sequence identity to SEQ ID NO: 54;
(bc) a polypeptide having at least 90% sequence identity to SEQ ID NO: 55;
(bd) a polypeptide having at least 90% sequence identity to SEQ ID NO: 56;
(be) a polypeptide having at least 90% sequence identity to SEQ ID NO: 57;
(bf) a polypeptide having at least 90% sequence identity to SEQ ID NO: 58;
(bg) a polypeptide having at least 90% sequence identity to SEQ ID NO: 59;
(bh) a polypeptide having at least 90% sequence identity to SEQ ID NO: 60;
(bi) a polypeptide having at least 90% sequence identity to SEQ ID NO: 61;
(bj) a polypeptide having at least 90% sequence identity to SEQ ID NO: 62;
(bk) a polypeptide having at least 90% sequence identity to SEQ ID NO: 63;
(bl) a polypeptide having at least 90% sequence identity to SEQ ID NO: 64;
(bm) a polypeptide having at least 90% sequence identity to SEQ ID NO: 65;
(bn) a polypeptide having at least 90% sequence identity to SEQ ID NO: 66;
(bo) a polypeptide having at least 90% sequence identity to SEQ ID NO: 67;
(bp) a polypeptide having at least 90% sequence identity to SEQ ID NO: 68;
(bq) a polypeptide having at least 90% sequence identity to SEQ ID NO: 69;
(br) a polypeptide having at least 90% sequence identity to SEQ ID NO: 70;
(bs) a polypeptide having at least 90% sequence identity to SEQ ID NO: 71;
(bt) a variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70 or SEQ ID NO: 71 comprising one or more amino acid substitutions, and/or one or more amino acid deletions, and/or one or more amino acid insertions or any combination thereof in 1, 2, 3, 4, 5, 6, 7, 8, 9 or 10 positions;
(bu) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) and a N-terminal and/or C-terminal extension of between 1 and 10 amino acids; and
(bv) a fragment of a polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) having muramidase activity and having at least 90% of the length of the mature polypeptide.

18. The animal feed or animal feed additive of claim 13, wherein the polypeptide having GH24 muramidase activity and/or GH25 muramidase activity is selected from the group consisting of:
(a) a polypeptide having at least 95% sequence identity to SEQ ID NO: 1;
(b) a polypeptide having at least 95% sequence identity to SEQ ID NO: 2;
(c) a polypeptide having at least 95% sequence identity to SEQ ID NO: 3;
(d) a polypeptide having at least 95% sequence identity to SEQ ID NO: 4;
(e) a polypeptide having at least 95% sequence identity to SEQ ID NO: 5;
(f) a polypeptide having at least 95% sequence identity to SEQ ID NO: 6;
(g) a polypeptide having at least 95% sequence identity to SEQ ID NO: 7;
(h) a polypeptide having at least 95% sequence identity to SEQ ID NO: 8;
(i) a polypeptide having at least 95% sequence identity to SEQ ID NO: 9;
(j) a polypeptide having at least 95% sequence identity to SEQ ID NO: 10;
(k) a polypeptide having at least 95% sequence identity to SEQ ID NO: 11;
(l) a polypeptide having at least 95% sequence identity to SEQ ID NO: 12;
(m) a polypeptide having at least 95% sequence identity to SEQ ID NO: 13;
(n) a polypeptide having at least 95% sequence identity to SEQ ID NO: 14;
(o) a polypeptide having at least 95% sequence identity to SEQ ID NO: 15;
(p) a polypeptide having at least 95% sequence identity to SEQ ID NO: 16;
(q) a polypeptide having at least 95% sequence identity to SEQ ID NO: 17;
(r) a polypeptide having at least 95% sequence identity to SEQ ID NO: 18;
(s) a polypeptide having at least 95% sequence identity to SEQ ID NO: 19;
(t) a polypeptide having at least 95% sequence identity to SEQ ID NO: 20;
(u) a polypeptide having at least 95% sequence identity to SEQ ID NO: 21;
(v) a polypeptide having at least 95% sequence identity to SEQ ID NO: 22;
(w) a polypeptide having at least 95% sequence identity to SEQ ID NO: 23;
(x) a polypeptide having at least 95% sequence identity to SEQ ID NO: 24;
(y) a polypeptide having at least 95% sequence identity to SEQ ID NO: 25;
(z) a polypeptide having at least 95% sequence identity to SEQ ID NO: 26;
(aa) a polypeptide having at least 95% sequence identity to SEQ ID NO: 27;
(ab) a polypeptide having at least 95% sequence identity to SEQ ID NO: 28;
(ac) a polypeptide having at least 95% sequence identity to SEQ ID NO: 29;
(ad) a polypeptide having at least 95% sequence identity to SEQ ID NO: 30;
(ae) a polypeptide having at least 95% sequence identity to SEQ ID NO: 31;
(af) a polypeptide having at least 95% sequence identity to SEQ ID NO: 32;
(ag) a polypeptide having at least 95% sequence identity to SEQ ID NO: 33;
(ah) a polypeptide having at least 95% sequence identity to SEQ ID NO: 34;
(ai) a polypeptide having at least 95% sequence identity to SEQ ID NO: 35;
(aj) a polypeptide having at least 95% sequence identity to SEQ ID NO: 36;
(ak) a polypeptide having at least 95% sequence identity to SEQ ID NO: 37;
(al) a polypeptide having at least 95% sequence identity to SEQ ID NO: 38;
(am) a polypeptide having at least 95% sequence identity to SEQ ID NO: 39;
(an) a polypeptide having at least 95% sequence identity to SEQ ID NO: 40;
(ao) a polypeptide having at least 95% sequence identity to SEQ ID NO: 41;
(ap) a polypeptide having at least 95% sequence identity to SEQ ID NO: 42;
(aq) a polypeptide having at least 95% sequence identity to SEQ ID NO: 43;
(ar) a polypeptide having at least 95% sequence identity to SEQ ID NO: 44;
(as) a polypeptide having at least 95% sequence identity to SEQ ID NO: 45;
(at) a polypeptide having at least 95% sequence identity to SEQ ID NO: 46;
(au) a polypeptide having at least 95% sequence identity to SEQ ID NO: 47;
(av) a polypeptide having at least 95% sequence identity to SEQ ID NO: 48;
(aw) a polypeptide having at least 95% sequence identity to SEQ ID NO: 49;
(ax) a polypeptide having at least 95% sequence identity to SEQ ID NO: 50;
(ay) a polypeptide having at least 95% sequence identity to SEQ ID NO: 51;
(az) a polypeptide having at least 95% sequence identity to SEQ ID NO: 52;
(ba) a polypeptide having at least 95% sequence identity to SEQ ID NO: 53;

(bb) a polypeptide having at least 95% sequence identity to SEQ ID NO: 54;
(bc) a polypeptide having at least 95% sequence identity to SEQ ID NO: 55;
(bd) a polypeptide having at least 95% sequence identity to SEQ ID NO: 56;
(be) a polypeptide having at least 95% sequence identity to SEQ ID NO: 57;
(bf) a polypeptide having at least 95% sequence identity to SEQ ID NO: 58;
(bg) a polypeptide having at least 95% sequence identity to SEQ ID NO: 59;
(bh) a polypeptide having at least 95% sequence identity to SEQ ID NO: 60;
(bi) a polypeptide having at least 95% sequence identity to SEQ ID NO: 61;
(bj) a polypeptide having at least 95% sequence identity to SEQ ID NO: 62;
(bk) a polypeptide having at least 95% sequence identity to SEQ ID NO: 63;
(bl) a polypeptide having at least 95% sequence identity to SEQ ID NO: 64;
(bm) a polypeptide having at least 95% sequence identity to SEQ ID NO: 65;
(bn) a polypeptide having at least 95% sequence identity to SEQ ID NO: 66;
(bo) a polypeptide having at least 95% sequence identity to SEQ ID NO: 67;
(bp) a polypeptide having at least 95% sequence identity to SEQ ID NO: 68;
(bq) a polypeptide having at least 95% sequence identity to SEQ ID NO: 69;
(br) a polypeptide having at least 95% sequence identity to SEQ ID NO: 70;
(bs) a polypeptide having at least 95% sequence identity to SEQ ID NO: 71;
(bt) a variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70 or SEQ ID NO: 71 comprising one or more amino acid substitutions, and/or one or more amino acid deletions, and/or one or more amino acid insertions or any combination thereof in 1, 2, 3, 4, 5, 6, 7, 8, 9 or 10 positions;
(bu) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) and a N-terminal and/or C-terminal extension of between 1 and 10 amino acids; and
(bv) a fragment of a polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) having muramidase activity and having at least 90% of the length of the mature polypeptide.

19. The animal feed or animal feed additive of claim 13, wherein the polypeptide having GH24 muramidase activity and/or GH25 muramidase activity is selected from the group consisting of:
(a) a polypeptide having at least 99% sequence identity to SEQ ID NO: 1;
(b) a polypeptide having at least 99% sequence identity to SEQ ID NO: 2;
(c) a polypeptide having at least 99% sequence identity to SEQ ID NO: 3;
(d) a polypeptide having at least 99% sequence identity to SEQ ID NO: 4;
(e) a polypeptide having at least 99% sequence identity to SEQ ID NO: 5;
(f) a polypeptide having at least 99% sequence identity to SEQ ID NO: 6;
(g) a polypeptide having at least 99% sequence identity to SEQ ID NO: 7;
(h) a polypeptide having at least 99% sequence identity to SEQ ID NO: 8;
(i) a polypeptide having at least 99% sequence identity to SEQ ID NO: 9;
(j) a polypeptide having at least 99% sequence identity to SEQ ID NO: 10;
(k) a polypeptide having at least 99% sequence identity to SEQ ID NO: 11;
(l) a polypeptide having at least 99% sequence identity to SEQ ID NO: 12;
(m) a polypeptide having at least 99% sequence identity to SEQ ID NO: 13;
(n) a polypeptide having at least 99% sequence identity to SEQ ID NO: 14;
(o) a polypeptide having at least 99% sequence identity to SEQ ID NO: 15;
(p) a polypeptide having at least 99% sequence identity to SEQ ID NO: 16;
(q) a polypeptide having at least 99% sequence identity to SEQ ID NO: 17;
(r) a polypeptide having at least 99% sequence identity to SEQ ID NO: 18;
(s) a polypeptide having at least 99% sequence identity to SEQ ID NO: 19;
(t) a polypeptide having at least 99% sequence identity to SEQ ID NO: 20;
(u) a polypeptide having at least 99% sequence identity to SEQ ID NO: 21;
(v) a polypeptide having at least 99% sequence identity to SEQ ID NO: 22;
(w) a polypeptide having at least 99% sequence identity to SEQ ID NO: 23;
(x) a polypeptide having at least 99% sequence identity to SEQ ID NO: 24;

(y) a polypeptide having at least 99% sequence identity to SEQ ID NO: 25;
(z) a polypeptide having at least 99% sequence identity to SEQ ID NO: 26;
(aa) a polypeptide having at least 99% sequence identity to SEQ ID NO: 27;
(ab) a polypeptide having at least 99% sequence identity to SEQ ID NO: 28;
(ac) a polypeptide having at least 99% sequence identity to SEQ ID NO: 29;
(ad) a polypeptide having at least 99% sequence identity to SEQ ID NO: 30;
(ae) a polypeptide having at least 99% sequence identity to SEQ ID NO: 31;
(af) a polypeptide having at least 99% sequence identity to SEQ ID NO: 32;
(ag) a polypeptide having at least 99% sequence identity to SEQ ID NO: 33;
(ah) a polypeptide having at least 99% sequence identity to SEQ ID NO: 34;
(ai) a polypeptide having at least 99% sequence identity to SEQ ID NO: 35;
(aj) a polypeptide having at least 99% sequence identity to SEQ ID NO: 36;
(ak) a polypeptide having at least 99% sequence identity to SEQ ID NO: 37;
(al) a polypeptide having at least 99% sequence identity to SEQ ID NO: 38;
(am) a polypeptide having at least 99% sequence identity to SEQ ID NO: 39;
(an) a polypeptide having at least 99% sequence identity to SEQ ID NO: 40;
(ao) a polypeptide having at least 99% sequence identity to SEQ ID NO: 41;
(ap) a polypeptide having at least 99% sequence identity to SEQ ID NO: 42;
(aq) a polypeptide having at least 99% sequence identity to SEQ ID NO: 43;
(ar) a polypeptide having at least 99% sequence identity to SEQ ID NO: 44;
(as) a polypeptide having at least 99% sequence identity to SEQ ID NO: 45;
(at) a polypeptide having at least 99% sequence identity to SEQ ID NO: 46;
(au) a polypeptide having at least 99% sequence identity to SEQ ID NO: 47;
(av) a polypeptide having at least 99% sequence identity to SEQ ID NO: 48;
(aw) a polypeptide having at least 99% sequence identity to SEQ ID NO: 49;
(ax) a polypeptide having at least 99% sequence identity to SEQ ID NO: 50;
(ay) a polypeptide having at least 99% sequence identity to SEQ ID NO: 51;
(az) a polypeptide having at least 99% sequence identity to SEQ ID NO: 52;
(ba) a polypeptide having at least 99% sequence identity to SEQ ID NO: 53;
(bb) a polypeptide having at least 99% sequence identity to SEQ ID NO: 54;
(bc) a polypeptide having at least 99% sequence identity to SEQ ID NO: 55;
(bd) a polypeptide having at least 99% sequence identity to SEQ ID NO: 56;
(be) a polypeptide having at least 99% sequence identity to SEQ ID NO: 57;
(bf) a polypeptide having at least 99% sequence identity to SEQ ID NO: 58;
(bg) a polypeptide having at least 99% sequence identity to SEQ ID NO: 59;
(bh) a polypeptide having at least 99% sequence identity to SEQ ID NO: 60;
(bi) a polypeptide having at least 99% sequence identity to SEQ ID NO: 61;
(bj) a polypeptide having at least 99% sequence identity to SEQ ID NO: 62;
(bk) a polypeptide having at least 99% sequence identity to SEQ ID NO: 63;
(bl) a polypeptide having at least 99% sequence identity to SEQ ID NO: 64;
(bm) a polypeptide having at least 99% sequence identity to SEQ ID NO: 65;
(bn) a polypeptide having at least 99% sequence identity to SEQ ID NO: 66;
(bo) a polypeptide having at least 99% sequence identity to SEQ ID NO: 67;
(bp) a polypeptide having at least 99% sequence identity to SEQ ID NO: 68;
(bq) a polypeptide having at least 99% sequence identity to SEQ ID NO: 69;
(br) a polypeptide having at least 99% sequence identity to SEQ ID NO: 70;
(bs) a polypeptide having at least 99% sequence identity to SEQ ID NO: 71;
(bt) a variant of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70 or SEQ ID NO: 71 comprising one or more amino acid substitutions, and/or one or more amino acid deletions, and/or one or more amino acid insertions or any combination thereof in 1, 2, 3, 4, 5, 6, 7, 8, 9 or 10 positions;
(bu) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) and a N-terminal and/or C-terminal extension of between 1 and 10 amino acids; and
(bv) a fragment of a polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs) or (bt) having muramidase activity and having at least 90% of the length of the mature polypeptide.

* * * * *

```
                        SEQUENCE LISTING

<160> NUMBER OF SEQ ID NOS: 71

<210> SEQ ID NO 1
<211> LENGTH: 208
<212> TYPE: PRT
<213> ORGANISM: Acremonium alcalophilum

<400> SEQUENCE: 1

Arg Ile Pro Gly Phe Asp Ile Ser Gly Trp Gln Pro Thr Thr Asp Phe
1               5                   10                  15

Ala Arg Ala Tyr Ala Asn Gly Asp Arg Phe Val Tyr Ile Lys Ala Thr
            20                  25                  30

Glu Gly Thr Thr Phe Lys Ser Ser Ala Phe Ser Arg Gln Tyr Thr Gly
        35                  40                  45

Ala Thr Gln Asn Gly Phe Ile Arg Gly Ala Tyr His Phe Ala Gln Pro
    50                  55                  60

Ala Ala Ser Ser Gly Ala Ala Gln Ala Arg Tyr Phe Ala Ser Asn Gly
65                  70                  75                  80

Gly Gly Trp Ser Lys Asp Gly Ile Thr Leu Pro Gly Ala Leu Asp Ile
                85                  90                  95

Glu Tyr Asn Pro Asn Gly Ala Thr Cys Tyr Gly Leu Ser Gln Ser Ala
            100                 105                 110

Met Val Asn Trp Ile Glu Asp Phe Val Thr Thr Tyr His Gly Ile Thr
        115                 120                 125

Ser Arg Trp Pro Val Ile Tyr Thr Thr Thr Asp Trp Trp Thr Gln Cys
    130                 135                 140

Thr Gly Asn Ser Asn Arg Phe Ala Asn Arg Cys Pro Leu Trp Ile Ala
145                 150                 155                 160

Arg Tyr Ala Ser Ser Val Gly Thr Leu Pro Asn Gly Trp Gly Phe Tyr
                165                 170                 175

Thr Phe Trp Gln Tyr Asn Asp Lys Tyr Pro Gln Gly Gly Asp Ser Asn
            180                 185                 190

Trp Phe Asn Gly Asp Ala Ser Arg Leu Arg Ala Leu Asn Gly Asp
        195                 200                 205

<210> SEQ ID NO 2
<211> LENGTH: 213
<212> TYPE: PRT
<213> ORGANISM: Acremonium alcalophilum

<400> SEQUENCE: 2

Ser Pro Ile Arg Arg Ile Pro Gly Phe Asp Ile Ser Gly Trp Gln
1               5                   10                  15

Pro Thr Thr Asp Phe Ala Arg Ala Tyr Ala Asn Gly Asp Arg Phe Val
            20                  25                  30

Tyr Ile Lys Ala Thr Glu Gly Thr Thr Phe Lys Ser Ser Ala Phe Ser
        35                  40                  45

Arg Gln Tyr Thr Gly Ala Thr Gln Asn Gly Phe Ile Arg Gly Ala Tyr
    50                  55                  60

His Phe Ala Gln Pro Ala Ala Ser Ser Gly Ala Ala Gln Ala Arg Tyr
65                  70                  75                  80

Phe Ala Ser Asn Gly Gly Gly Trp Ser Lys Asp Gly Ile Thr Leu Pro
                85                  90                  95
```

```
Gly Ala Leu Asp Ile Glu Tyr Asn Pro Asn Gly Ala Thr Cys Tyr Gly
            100                 105                 110

Leu Ser Gln Ser Ala Met Val Asn Trp Ile Glu Asp Phe Val Thr Thr
            115                 120                 125

Tyr His Gly Ile Thr Ser Arg Trp Pro Val Ile Tyr Thr Thr Thr Asp
            130                 135                 140

Trp Trp Thr Gln Cys Thr Gly Asn Ser Asn Arg Phe Ala Asn Arg Cys
145                 150                 155                 160

Pro Leu Trp Ile Ala Arg Tyr Ala Ser Ser Val Gly Thr Leu Pro Asn
                165                 170                 175

Gly Trp Gly Phe Tyr Thr Phe Trp Gln Tyr Asn Asp Lys Tyr Pro Gln
                180                 185                 190

Gly Gly Asp Ser Asn Trp Phe Asn Gly Asp Ala Ser Arg Leu Arg Ala
                195                 200                 205

Leu Ala Asn Gly Asp
            210

<210> SEQ ID NO 3
<211> LENGTH: 218
<212> TYPE: PRT
<213> ORGANISM: Aspergillus fumigatus

<400> SEQUENCE: 3

Leu Pro Ser Gln Pro Glu Ala Arg Ala Thr Thr Val Gln Gly Phe Asp
1               5                   10                  15

Ile Ser Asn His Gln Lys Ser Val Asn Phe Glu Ala Ala Lys Lys Asp
            20                  25                  30

Gly Ala Gln Phe Val Met Ile Lys Ala Thr Glu Gly Thr Thr Tyr Lys
        35                  40                  45

Asp Thr Val Phe Asn Ser His Tyr Thr Gly Ala Thr Lys Ala Gly Leu
    50                  55                  60

Leu Arg Gly Gly Tyr His Phe Ala Arg Pro Asp Lys Ser Thr Gly Ser
65                  70                  75                  80

Thr Gln Ala Lys Phe Phe Leu Lys Asn Gly Gly Gly Trp Ser Asp Asp
                85                  90                  95

Asn Arg Thr Leu Pro Gly Met Leu Asp Ile Glu Tyr Asn Pro Tyr Gly
            100                 105                 110

Ala Thr Cys Tyr Gly Leu Ser His Ser Gln Met Val Ala Trp Ile His
            115                 120                 125

Asp Phe Val Asn Glu Tyr His His Ala Thr Ser Arg Trp Pro Met Ile
        130                 135                 140

Tyr Thr Thr Ala Asp Trp Trp Asn Arg Cys Thr Gly Asn Ala Lys Gly
145                 150                 155                 160

Phe Gly Asp Lys Cys Pro Leu Val Leu Ala Ala Tyr Ser Ser Ser Pro
                165                 170                 175

Pro Lys Thr Ile Pro Gly Asp Trp Lys Thr Trp Thr Ile Trp Gln Asn
            180                 185                 190

Ser Asp Lys Tyr Lys His Gly Gly Asp Ser Asp Lys Phe Asn Gly Pro
        195                 200                 205

Met Thr Gln Leu Arg Lys Leu Ala Ser Gly
    210                 215

<210> SEQ ID NO 4
<211> LENGTH: 208
<212> TYPE: PRT
```

<213> ORGANISM: Trichoderma reesei

<400> SEQUENCE: 4

```
Thr Val Pro Gly Phe Asp Ile Ser His Tyr Gln Ala Thr Val Asp Phe
1               5                   10                  15

Ala Lys Ala Tyr Ala Asp Gly Arg Phe Val Ile Ile Lys Ala Thr
            20                  25                  30

Glu Gly Thr Thr Tyr Thr Asp Pro Ser Phe Ser Asp His Tyr Thr Lys
        35                  40                  45

Ala Thr Asn Ala Gly Phe Ile Arg Gly Gly Tyr His Phe Ala Gln Pro
    50                  55                  60

Ala Ser Ser Ser Gly Ala Ala Gln Ala Asn Tyr Phe Leu Lys His Gly
65                  70                  75                  80

Gly Gly Trp Ser Ala Asp Gly Ile Thr Leu Pro Gly Met Leu Asp Leu
                85                  90                  95

Glu Tyr Ala Pro Ser Gly Asp Ser Cys Tyr Gly Leu Ser Ala Ser Ala
            100                 105                 110

Met Val Ser Trp Ile Asn Asp Phe Val Asn Thr Tyr His Ala Ala Thr
        115                 120                 125

Thr Gln Tyr Pro Leu Ile Tyr Thr Ser Thr Ser Trp Trp Gln Leu Cys
    130                 135                 140

Thr Gly Asn Asn Gly Ser Phe Gly Ser Lys Ser Pro Leu Val Ile Ala
145                 150                 155                 160

Arg Tyr Ala Ser Ser Val Gly Ala Leu Pro Asn Gly Trp Ser Val Tyr
                165                 170                 175

Thr Ile Trp Gln Asn Ser Asp Ala Ser Pro Trp Gly Gly Asp Asn Asp
            180                 185                 190

Ile Phe Asn Gly Asn Leu Ala Gln Leu Gln Lys Ile Ala Arg Gly Ser
        195                 200                 205
```

<210> SEQ ID NO 5
<211> LENGTH: 215
<212> TYPE: PRT
<213> ORGANISM: Trametes cinnabarina

<400> SEQUENCE: 5

```
Ser Pro Thr Pro Glu Lys Arg Ala Asn Pro Lys Gly Ile Asp Val Ser
1               5                   10                  15

Ala Tyr Gln Pro Asn Ile Asn Trp Ser Thr Val Lys Ala Asn Gly Ile
            20                  25                  30

Ser Phe Ala Tyr Ile Lys Ala Thr Glu Gly Thr Thr Tyr Thr Asn Pro
        35                  40                  45

Asp Phe Ser Ser Gln Tyr Thr Gly Ala Thr Asn Ala Gly Leu Ile Arg
    50                  55                  60

Gly Gly Tyr His Phe Ala His Pro Asp Ser Ser Gly Ala Thr Gln
65                  70                  75                  80

Ala Lys Tyr Phe Leu Ala His Gly Gly Gly Trp Thr Ser Asp Gly Ile
                85                  90                  95

Thr Leu Pro Gly Ala Leu Asp Ile Glu Tyr Asn Pro Ser Gly Ala Glu
            100                 105                 110

Cys Tyr Gly Leu Ser Ala Ser Ala Met Val Ser Trp Ile Lys Asp Phe
        115                 120                 125

Ser Asn Thr Tyr His Ser Ser Thr Gly Val Tyr Pro Val Ile Tyr Thr
    130                 135                 140
```

```
Thr Thr Asp Trp Trp Thr Cys Thr Gly Asn Ser Ala Ala Phe Ala
145                 150                 155                 160

Ser Thr Asn Pro Leu Trp Ile Ala Arg Tyr Ala Ser Ser Ile Gly Thr
            165                 170                 175

Leu Pro Ala Gly Trp Ser Tyr Thr Thr Phe Trp Gln Tyr Ala Asp Ser
        180                 185                 190

Gly Pro Asn Pro Gly Asp Gln Asp Glu Phe Asn Gly Ser Met Ala Gly
        195                 200                 205

Leu Lys Gln Leu Ala Leu Gly
    210                 215

<210> SEQ ID NO 6
<211> LENGTH: 207
<212> TYPE: PRT
<213> ORGANISM: Sporormia fimetaria

<400> SEQUENCE: 6

Ala Val Pro Gly Phe Asp Ile Ser His Tyr Gln Ser Ser Val Asn Tyr
1               5                   10                  15

Ala Gly Ala Tyr Ser Ser Gly Ala Arg Phe Val Ile Ile Lys Ala Thr
            20                  25                  30

Glu Gly Thr Thr Tyr Ile Asp Pro Lys Phe Ser Asp His Tyr Ile Gly
        35                  40                  45

Ala Thr Asn Ala Gly Leu Ile Arg Gly Ala Tyr His Phe Ala Arg Pro
    50                  55                  60

Ala Ala Ser Thr Gly Ala Ala Gln Ala Asn Tyr Phe Val Ser His Gly
65                  70                  75                  80

Gly Gly Trp Ser Ala Asp Gly Ile Thr Leu Pro Gly Met Leu Asp Met
            85                  90                  95

Glu Tyr Gly Ser Thr Ser Ala Cys His Gly Leu Ser Gln Ser Ala Met
        100                 105                 110

Val Thr Trp Ile Thr Ser Phe Val Asn Gln Tyr Asn Ser Leu Thr Gly
    115                 120                 125

Arg Tyr Pro Met Ile Tyr Thr Thr Ala Asp Trp Trp Gln Thr Cys Thr
130                 135                 140

Gly Asn Ser Ala Ala Phe Asn Thr Lys Ser Pro Leu Val Leu Ala Arg
145                 150                 155                 160

Tyr Ser Ser Ser Ala Gly Thr Val Pro Gly Gly Trp Pro Tyr Tyr Thr
            165                 170                 175

Ile Trp Gln Phe Asn Asp Ala Tyr Ala Tyr Gly Gly Asp Ser Asp Thr
        180                 185                 190

Phe Asn Gly Asp Leu Ala Gly Leu Lys Arg Leu Ala Lys Gly Ser
        195                 200                 205

<210> SEQ ID NO 7
<211> LENGTH: 201
<212> TYPE: PRT
<213> ORGANISM: Poronia punctata

<400> SEQUENCE: 7

Ala Val Gln Gly Phe Asp Ile Ser His Tyr Gln Ser Ser Val Asn Phe
1               5                   10                  15

Gly Ala Ala Lys Ser Ser Gly Ala Gln Phe Val Ile Ile Lys Ala Thr
            20                  25                  30

Glu Gly Thr Ser Tyr Thr Asp Pro Ser Phe Ser Ser His Tyr Thr Gly
        35                  40                  45
```

```
Ala Thr Asn Ala Gly Leu Ile Arg Gly Gly Tyr His Phe Ala His Leu
        50                  55                  60

Asp Ser Ser Gly Ala Gln Ala Lys Tyr Phe Leu Ala His Gly
65                  70                  75                  80

Gly Gly Trp Ser Gly Asp Gly Ile Thr Leu Pro Gly Met Leu Asp Leu
                85                  90                  95

Glu Gly Ser Cys Val Leu Ser Ala Ser Ala Thr Val Ser Trp Ile Lys
            100                 105                 110

Asp Phe Ser Asn Thr Tyr His Ser Ser Thr Gly Val Tyr Pro Leu Ile
            115                 120                 125

Tyr Thr Asn Pro Ser Trp Trp Ser Ser Cys Thr Gly Asn Ser Lys Ala
        130                 135                 140

Phe Ile Asp Thr Asn Pro Leu Val Leu Ala Arg Tyr Ala Ser Ser Ala
145                 150                 155                 160

Gly Thr Pro Pro Gly Gly Trp Pro Tyr Tyr Thr Ile Trp Gln Tyr Asn
                165                 170                 175

Asp Ala Tyr Lys Tyr Gly Gly Asp Ser Asp Val Phe Asn Gly Asp Leu
            180                 185                 190

Ala Gly Leu Lys Arg Leu Ala Lys Gly
        195                 200

<210> SEQ ID NO 8
<211> LENGTH: 201
<212> TYPE: PRT
<213> ORGANISM: Poronia punctata

<400> SEQUENCE: 8

Gln Val Gln Gly Phe Asp Ile Ser Ser Tyr Gln Pro Ser Val Asp Phe
1               5                   10                  15

Ala Gly Ala Tyr Ala Asp Gly Ala Arg Phe Val Ile Ile Lys Ala Thr
            20                  25                  30

Glu Gly Thr Gly Tyr Ile Asp Pro Thr Phe Ser Asp His Tyr Val Gly
        35                  40                  45

Ala Thr Asn Ala Gly Leu Leu Arg Gly Gly Tyr His Tyr Ala His Leu
        50                  55                  60

Asp Ser Thr Ser Gly Ala Thr Gln Ala Gln Tyr Phe Leu Ala Asn Gly
65                  70                  75                  80

Gly Gly Trp Ser Gly Asp Gly Ile Thr Leu Pro Gly Met Leu Asp Leu
                85                  90                  95

Glu Gly Asp Cys Val Leu Ser Ala Ala Asp Ala Val Ala Trp Ile Lys
            100                 105                 110

Asp Phe Ser Asp Thr Tyr His Ala Ser Thr Gly Val Tyr Pro Leu Leu
            115                 120                 125

Tyr Thr Asn Pro Ser Trp Trp Ala Ser Cys Thr Gly Asp Ser Ser Ala
        130                 135                 140

Phe Ile Asp Thr Asn Pro Leu Val Leu Ala His Tyr Ala Asp Ala Ala
145                 150                 155                 160

Gly Thr Pro Pro Gly Gly Trp Pro Phe Tyr Ser Phe Trp Gln Tyr Asn
                165                 170                 175

Asp Ala Tyr Pro Tyr Gly Gly Asp Ser Glu Val Trp Asn Gly Asp Met
            180                 185                 190

Asp Gly Leu Leu Arg Leu Ala Ser Gly
        195                 200
```

-continued

<210> SEQ ID NO 9
<211> LENGTH: 203
<212> TYPE: PRT
<213> ORGANISM: Lecanicillium sp. WMM742

<400> SEQUENCE: 9

Val Asp Ser Ser Glu Val Ser Val Ala Ile Tyr Lys Lys Ala Leu
1               5                   10                  15

Gly Gln Gly Phe Thr Arg Ala Ile Phe Arg Gly Tyr Gln Glu Ala Cys
                20                  25                  30

Ser Gln Gly Gly Arg Val Asp Pro Thr Phe Val Pro Ser Tyr Lys Asn
            35                  40                  45

Ala Val Ala Ala Gly Tyr Lys Asp Phe Asp Ala Tyr Phe Phe Pro Cys
        50                  55                  60

Thr Gly Lys Thr Asn Lys Cys Lys Pro Tyr Ala Ala Gln Leu Ala Glu
65                  70                  75                  80

Leu Leu Asp Thr Ile Lys Gly Gln Lys Leu Ala Ile Arg Arg Ile Trp
                85                  90                  95

Leu Asp Ile Glu Thr Asp Arg Val Cys Asn Pro Phe Asp Tyr Gly Ala
                100                 105                 110

Gln Gly Asn Leu Ala Glu Ala Lys Lys Leu Val Ala Ala Phe Arg Asp
            115                 120                 125

Ala Lys Leu Asp Trp Gly Ile Tyr Thr Ser Pro Thr Gln Trp Glu Thr
        130                 135                 140

Ile Phe Gly Ala Lys Thr Val Glu Leu Ala Lys Asp Val Pro Leu Trp
145                 150                 155                 160

Phe Ala Lys Phe Asp Asn Val Glu Thr Leu Glu Leu Lys Thr Pro Phe
                165                 170                 175

Gly Gly Trp Thr Lys Ala Asp Ala Lys Gln Tyr Thr Asp Gln Ser Ala
                180                 185                 190

Ser Asn Lys Phe Asp Leu Asn Val Phe Ser Ala
            195                 200

<210> SEQ ID NO 10
<211> LENGTH: 208
<212> TYPE: PRT
<213> ORGANISM: Lecanicillium sp. WMM742

<400> SEQUENCE: 10

Thr Val Gln Gly Phe Asp Val Ser Gly Tyr Gln Pro Thr Val Asn Trp
1               5                   10                  15

Gly Ala Ala Tyr Ser Ser Gly Ala Arg Phe Val Met Ile Lys Ala Thr
                20                  25                  30

Glu Gly Thr Gly Tyr Ile Ser Ser Phe Gly Ser Gln Tyr Pro Gly
            35                  40                  45

Ala Thr Asn Ala Gly Phe Ile Arg Gly Gly Tyr His Phe Ala Leu Pro
        50                  55                  60

Asp Arg Ser Ser Gly Ser Ala Gln Ala Asp Tyr Phe Leu Ala His Gly
65                  70                  75                  80

Gly Gly Trp Ser Gly Asp Gly Ile Thr Leu Pro Gly Met Leu Asp Ile
                85                  90                  95

Glu Tyr Asn Pro Tyr Gly Ala Thr Cys Tyr Gly Leu Ser Gln Gly Ala
                100                 105                 110

Met Val Asn Trp Ile Ser Asp Phe Val Glu His Tyr Lys Ala Arg Thr
            115                 120                 125

Thr Gln Tyr Pro Ile Ile Tyr Thr Thr Asp Trp Trp Lys Thr Cys
    130                 135                 140

Thr Gly Asn Ser Pro Ala Phe Gly Gln Lys Cys Pro Leu Ser Leu Ala
145                 150                 155                 160

Arg Tyr Ser Ser Val Gly Glu Ile Pro Asn Gly Trp Pro Phe Gln
                165                 170                 175

Thr Phe Trp Gln Asn Ser Asp Lys Tyr Ala Tyr Gly Gly Asp Ser Gln
        180                 185                 190

Ile Phe Asn Gly Ala Tyr Ser Gln Leu Gln Lys Ile Ala Arg Gly Gly
                195                 200                 205

<210> SEQ ID NO 11
<211> LENGTH: 207
<212> TYPE: PRT
<213> ORGANISM: Onygena equina

<400> SEQUENCE: 11

Ala Val Pro Gly Ile Asp Val Ser Gly Tyr Gln Gly Asn Val Asn Trp
1               5                   10                  15

Ala Asn Val Ala Asn Ala Gly Lys Lys Phe Ala Tyr Val Lys Ala Thr
                20                  25                  30

Glu His Thr Asn Tyr Ile Asn Pro Tyr Phe Ala Gln Gln Tyr Asn Gly
            35                  40                  45

Ala Tyr Asn Gln Gly Ile Ile Arg Gly Ala Tyr His Tyr Ala His Pro
    50                  55                  60

Asn Gly Ala Ser Gly Ala Ser Gln Ala Asn Tyr Phe Leu Ala His Gly
65                  70                  75                  80

Gly Gly Trp Ser Ala Asp Gly Lys Thr Leu Pro Gly Ala Val Asp Leu
                85                  90                  95

Glu Tyr Gly Pro Asn Gly Ser Thr Cys Trp Gly Ile Ser Gln Ser Ala
            100                 105                 110

Met Ile Ala Trp Ile Arg Asp Phe Ser Asn Thr Tyr Arg Ala Lys Thr
        115                 120                 125

Gly Arg Pro Pro Val Ile Tyr Thr Ser Thr Ser Trp Trp Lys Thr Cys
    130                 135                 140

Thr Gly Asn Tyr Gly Gly Phe Gly Asn Asp Asn Pro Leu Trp Ile Ala
145                 150                 155                 160

Arg Tyr Ser Ser Thr Val Gly Glu Leu Pro Ala Gly Trp Pro Phe His
                165                 170                 175

Ser Ile Trp Gln Asn Asn Asp Asn Ser Gly Val Gly Gly Asp Gly Asp
        180                 185                 190

Ile Trp Asn Gly Asp Leu Ala Gly Leu Gln Arg Phe Ala Lys Gly
            195                 200                 205

<210> SEQ ID NO 12
<211> LENGTH: 208
<212> TYPE: PRT
<213> ORGANISM: Purpureocillium lilacinum

<400> SEQUENCE: 12

Ala Val Lys Gly Phe Asp Ile Ser His Tyr Gln Pro Asn Val Asp Phe
1               5                   10                  15

Ala Lys Ala Tyr Ala Asp Gly Ala Arg Phe Val Met Ile Lys Ala Thr
                20                  25                  30

Glu Gly Thr Thr Tyr Thr Asp Pro Ser Phe Ser Ser His Tyr Thr Gly
            35                  40                  45

```
Ala Thr Lys Ala Gly Phe Ile Arg Gly Gly Tyr His Phe Ala Arg Pro
         50                  55                  60

Ala Ser Ser Ser Gly Ala Ala Gln Ala Lys Tyr Phe Ile Ala His Gly
 65              70                  75                  80

Gly Gly Trp Ser Lys Asp Gly Ile Thr Leu Pro Gly Met Leu Asp Met
                 85                  90                  95

Glu Tyr Gln Ser Ser Ser Ala Cys Gly Gly Leu Ser Gln Ser Ala
                100                 105                 110

Met Val Ser Trp Ile Asn Asp Phe Val Asn Thr Tyr His Ala Ala Thr
             115                 120                 125

Gly Val Tyr Pro Leu Ile Tyr Thr Ser Thr Ser Trp Trp Thr Gln Cys
         130                 135                 140

Thr Gly Asn Ser Ala Ala Phe Gly Ser Lys Cys Pro Leu Val Val Ala
145                 150                 155                 160

Arg Tyr Ala Ser Ser Val Gly Thr Leu Pro Ala Gly Trp Gly Phe Tyr
                 165                 170                 175

Thr Phe Trp Gln Tyr Ser Asp Ala Ala Pro Trp Gly Gly Asp Ala Asp
             180                 185                 190

Thr Phe Asn Gly Asp Ile Thr Ala Leu Lys Lys Ile Ala Asn Ala Gly
             195                 200                 205

<210> SEQ ID NO 13
<211> LENGTH: 207
<212> TYPE: PRT
<213> ORGANISM: Trichobolus zukalii

<400> SEQUENCE: 13

Ala Val Pro Gly Phe Asp Ile Ser His Tyr Gln Pro Ser Val Asn Tyr
 1               5                  10                  15

Ala Gly Ala Tyr Asn Ser Gly Ala Arg Phe Val Ile Ile Lys Ala Thr
             20                  25                  30

Glu Gly Thr Thr Tyr Thr Asp Pro Val Phe Ser Thr His Tyr Thr Gly
         35                  40                  45

Ala Thr Lys Ala Gly Leu Ile Arg Gly Gly Tyr His Phe Ala Arg Pro
         50                  55                  60

Ala Ser Ser Ser Gly Ser Ala Gln Ala Asp Phe Phe Phe Lys Asn Gly
 65              70                  75                  80

Gly Gly Trp Ser Ala Asp Gly Ile Thr Leu Pro Gly Met Leu Asp Met
                 85                  90                  95

Glu Tyr Gly Ser Thr Ser Ser Cys His Gly Leu Ser Gln Thr Ala Met
                100                 105                 110

Val Asn Trp Ile Ser Asp Phe Val Asn Arg Tyr Lys Thr Leu Ser Gly
             115                 120                 125

Arg Tyr Pro Met Ile Tyr Thr Gly Tyr Tyr Trp Trp Val Glu Cys Thr
         130                 135                 140

Gly Asn Ser Asn Lys Phe Ala Thr Thr Cys Pro Leu Val Leu Ala Arg
145                 150                 155                 160

Tyr Ser Ser Ser Val Gly Glu Ile Pro Gly Trp Gly Tyr Gln Thr
                 165                 170                 175

Ile Trp Gln Phe Asn Asp Lys Tyr Ala Tyr Gly Gly Asp Ser Asp Ser
             180                 185                 190

Phe Asn Gly Ser Leu Asp Arg Leu Lys Ala Leu Ala Lys Gly Thr
             195                 200                 205
```

<210> SEQ ID NO 14
<211> LENGTH: 207
<212> TYPE: PRT
<213> ORGANISM: Penicillium citrinum

<400> SEQUENCE: 14

```
Leu Ile His Ala Val Asp Ser Ser Glu Val Ser Val Asp Ile Tyr
1               5                   10                  15

Lys Lys Ala Leu Ser Glu Gly Phe Ser Arg Ala Ile Phe Arg Gly Tyr
            20                  25                  30

Gln Glu Ala Cys Ser Gln Gly Gly Arg Val Asp Pro Thr Phe Leu Pro
        35                  40                  45

Ser Tyr Lys Asn Ala Gln Thr Ala Gly Tyr Lys Asp Phe Asp Ala Tyr
    50                  55                  60

Phe Phe Pro Cys Thr Gly Ser Gly Asn Lys Cys Lys Pro Tyr Asp Val
65                  70                  75                  80

Gln Ile Gly Glu Leu Val Asp Ala Ile Lys Lys Asn Asn Met Ala Ile
                85                  90                  95

Arg Arg Ile Trp Val Asp Phe Glu Lys Asp Lys Thr Cys Asn Pro Phe
            100                 105                 110

Asn Trp Asp Pro Lys Arg Asn Ile Asp Glu Ala Lys Arg Ile Ile Gly
        115                 120                 125

Ala Val Arg Lys Thr Lys Phe Asp Phe Gly Val Tyr Thr Ser Ala Thr
    130                 135                 140

Gln Trp Thr Ser Ile Phe Gly Ser Lys Asp Val Val Leu Ala Asn Asp
145                 150                 155                 160

Val Pro Leu Trp Phe Ala Lys Phe Asp Asn Val Glu Asn Leu Asp Leu
                165                 170                 175

Ala Gln Pro Phe Gly Gly Trp Thr Lys Ala Asp Gly Lys Gln Tyr Thr
            180                 185                 190

Asp Lys Ser Ala Ser Lys Lys Phe Asp Leu Asn Val Phe Ser Ala
        195                 200                 205
```

<210> SEQ ID NO 15
<211> LENGTH: 207
<212> TYPE: PRT
<213> ORGANISM: Cladorrhinum bulbillosum

<400> SEQUENCE: 15

```
Ala Val Gln Gly Phe Asp Ile Ser His Tyr Gln Ser Ser Val Asn Phe
1               5                   10                  15

Gln Ala Ala Tyr Asn Ser Gly Ala Arg Phe Val Ile Ile Lys Ala Thr
            20                  25                  30

Glu Gly Thr Thr Tyr Ile Asp Pro Lys Phe Ser Ser His Tyr Thr Gly
        35                  40                  45

Ala Thr Asn Ala Gly Leu Ile Arg Gly Gly Tyr His Phe Ala His Pro
    50                  55                  60

Asp Ser Ser Thr Gly Ala Ala Gln Ala Asp Phe Phe Leu Ala His Gly
65                  70                  75                  80

Gly Gly Trp Ser Gly Asp Gly Ile Thr Leu Pro Gly Met Leu Asp Leu
                85                  90                  95

Glu Ser Val Ser Gly Lys Ala Thr Cys Phe Gly Leu Ser Ala Ser Ser
            100                 105                 110

Met Val Ala Trp Ile Lys Ser Phe Ser Asp Arg Tyr His Thr Arg Thr
        115                 120                 125
```

```
Gly Arg Tyr Pro Met Leu Tyr Thr Asn Pro Ser Trp Trp Thr Thr Cys
        130                 135                 140

Thr Gly Asn Ser Asn Ala Phe Val Asn Thr Asn Pro Leu Val Leu Ala
145                 150                 155                 160

Arg Tyr Ala Ser Ala Pro Gly Thr Ile Pro Gly Gly Trp Pro Tyr Gln
                165                 170                 175

Thr Ile Trp Gln Asn Ser Asp Ser Tyr Thr Tyr Gly Gly Asp Ser Asp
                180                 185                 190

Ile Phe Asn Gly Ala Leu Ser Gly Leu Gln Lys Leu Ala Ser Gly
            195                 200                 205
```

<210> SEQ ID NO 16
<211> LENGTH: 208
<212> TYPE: PRT
<213> ORGANISM: Umbelopsis westeae

<400> SEQUENCE: 16

```
Lys Leu Lys Gly Leu Asp Val Ser Gly Tyr Gln Pro Asn Val Ala Trp
1               5                   10                  15

Ser Thr Val Lys Ala Asn Gly Ala Ser Phe Ala Tyr Ile Lys Ala Thr
                20                  25                  30

Glu Gly Thr Asn Tyr Lys Asn Pro Ser Phe Ala Gln Gln Tyr Asn Gly
            35                  40                  45

Ala Tyr Asn Ala Gly Leu Ile Arg Gly Ser Tyr His Phe Ala Gln Pro
        50                  55                  60

Ser Ser Ser Thr Gly Ala Ala Gln Ala Asn Tyr Phe Leu Ala His Gly
65                  70                  75                  80

Gly Gly Trp Ser Pro Asp Gly Lys Thr Leu Pro Gly Ala Leu Asp Met
                85                  90                  95

Glu Tyr Asn Pro His Gly Ser Thr Cys Tyr Gly Leu Ser Lys Asp Ala
            100                 105                 110

Met Val Lys Trp Ile Lys Asp Phe Ser Asn Thr Tyr His Ser Ala Thr
        115                 120                 125

Gly Arg Tyr Pro Val Ile Tyr Thr Thr Thr Ser Trp Trp Thr Thr Cys
    130                 135                 140

Thr Gly Asn Ser Ala Ala Phe Gly Ala Thr Asn Pro Leu Trp Ile Ala
145                 150                 155                 160

Arg Tyr Ser Ser Thr Ala Gly Asn Leu Pro Asn Gly Trp Ala Phe Tyr
                165                 170                 175

Ser Phe Trp Gln Asn Ala Asp Ser Gly Ile Phe Pro Asp Gln Asp
                180                 185                 190

Ile Trp Asn Gly Asp Ala Ala Leu Ser Arg Met Ala Lys Gly Ala
            195                 200                 205
```

<210> SEQ ID NO 17
<211> LENGTH: 208
<212> TYPE: PRT
<213> ORGANISM: Zygomycetes sp. XZ2655

<400> SEQUENCE: 17

```
Thr Leu Pro Gly Leu Asp Val Ser Ser Tyr Gln Gly Asn Val Asn Trp
1               5                   10                  15

Gly Thr Val Ala Ser Gln Gly Ala Lys Phe Ala Tyr Val Lys Ala Thr
                20                  25                  30

Glu Gly Thr Thr Tyr Thr Asn Pro Tyr Phe Ala Ser Gln Tyr Asp Gly
            35                  40                  45
```

```
Ser Tyr Asn Ala Gly Leu Ile Arg Gly Ala Tyr His Phe Ala His Pro
    50                  55                  60

Asp Ser Ser Gly Ala Thr Gln Ala Asn Tyr Phe Leu Ala His Gly
65                  70                  75                  80

Gly Gly Trp Ser Ala Asp Gly Lys Thr Leu Pro Gly Ala Leu Asp Ile
                85                  90                  95

Glu Tyr Asn Pro Asn Gly Ala Glu Cys Tyr Gly Leu Ser Gln Leu Ala
                100                 105                 110

Met Ile Ser Trp Ile Gln Asp Phe Ser Asn Thr Tyr His Ser His Thr
            115                 120                 125

Gly Arg Tyr Pro Val Ile Tyr Thr Thr Thr Asp Trp Trp Thr Thr Cys
130                 135                 140

Thr Gly Asn Ser Ala Ala Phe Gly Thr Asn Asn Pro Leu Trp Ile Ala
145                 150                 155                 160

Arg Tyr Ser Ser Ser Val Gly Thr Leu Pro Ala Gly Trp Gly Tyr Glu
                165                 170                 175

Ser Phe Trp Gln Lys Ala Ser Ser Gly Thr Phe Pro Gly Asp Gln Asp
            180                 185                 190

Ile Trp Asn Gly Asp Ala Ala Gly Leu Ser Arg Phe Ala Thr Gly Lys
            195                 200                 205

<210> SEQ ID NO 18
<211> LENGTH: 206
<212> TYPE: PRT
<213> ORGANISM: Chaetomium cupreum

<400> SEQUENCE: 18

Thr Val Gln Gly Phe Asp Ile Ser Gly Tyr Gln Pro Asn Val Asn Phe
1               5                   10                  15

Ala Ala Ala Tyr Ala Gly Ala Arg Phe Val Ile Ile Lys Ala Thr
            20                  25                  30

Glu Gly Thr Ser Tyr Ile Ser Pro Ser Phe Ser Ser Gln Tyr Thr Gly
            35                  40                  45

Ala Thr Asn Ala Gly Phe Ile Arg Gly Gly Tyr His Phe Ala His Pro
50                  55                  60

Gly Ala Ser Ser Gly Thr Thr Gln Ala Asp Tyr Phe Ile Ala His Gly
65                  70                  75                  80

Gly Gly Trp Thr Pro Asp Gly Ile Thr Leu Pro Gly Met Leu Asp Leu
                85                  90                  95

Glu Ser Glu Ser Ser Gly Thr Cys Trp Gly Leu Ser Ala Ser Ala Met
                100                 105                 110

Val Ala Trp Ile Lys Asp Phe Asp His Tyr His Ser Arg Met Gly
            115                 120                 125

Val Tyr Pro Leu Leu Tyr Thr Asn Pro Ser Trp Trp Glu Glu Cys Thr
130                 135                 140

Gly Asn Ser Asn Ala Phe Val Asp Thr Asn Pro Leu Val Leu Ala His
145                 150                 155                 160

Tyr Ser Ser Ser Val Gly Thr Ile Pro Gly Gly Trp Pro Tyr Glu Thr
                165                 170                 175

Ile Trp Gln Asn Ser Asp Ser Tyr Ala Tyr Gly Gly Asp Ser Asp Val
            180                 185                 190

Phe Asn Gly Asp Leu Ala Gly Leu Gln Arg Leu Ala Arg Gly
            195                 200                 205
```

```
<210> SEQ ID NO 19
<211> LENGTH: 207
<212> TYPE: PRT
<213> ORGANISM: Cordyceps cardinalis

<400> SEQUENCE: 19

Leu Ile His Ala Val Asp Ser Ser Glu Val Ser Val Asp Val Tyr
1               5                   10                  15

Lys Lys Ala Leu Ala Glu Gly Phe Thr Arg Ala Ile Phe Arg Gly Tyr
            20                  25                  30

Gln Glu Ala Cys Ser Gln Gly Gly Arg Val Asp Pro Thr Phe Leu Pro
        35                  40                  45

Ser Tyr Lys Asn Ala Gln Lys Ala Gly Tyr Lys Asp Phe Asp Ala Tyr
    50                  55                  60

Phe Phe Pro Cys Thr Gly Ser Gly Asn Lys Cys Lys Pro Tyr Ala Lys
65                  70                  75                  80

Gln Ile Gly Glu Leu Val Asp Ala Ile Glu Gly Asn Gln Leu Ala Ile
                85                  90                  95

Arg Arg Ile Trp Ile Asp Ile Glu Thr Asp Lys Val Cys Asn Ala Phe
            100                 105                 110

Asn Trp Gly Ala Glu Gly Asn Ile Gln Glu Ala Lys Lys Leu Ile Ala
        115                 120                 125

Ala Val Arg Gly Thr Lys Arg Asp Phe Gly Ile Tyr Thr Ser Ala Thr
    130                 135                 140

Gln Trp Glu Asn Ile Phe Gly Ser Arg Thr Val Glu Leu Ala Lys Asp
145                 150                 155                 160

Val Pro Leu Trp Phe Ala Lys Phe Asp Asn Val Glu Thr Leu Glu Leu
                165                 170                 175

Lys Thr Pro Phe Gly Gly Trp Thr Lys Ala Asp Ala Lys Gln Tyr Thr
            180                 185                 190

Asp Lys Ser Ala Ser Lys Lys Phe Asp Leu Asn Val Phe Ser Ala
        195                 200                 205

<210> SEQ ID NO 20
<211> LENGTH: 216
<212> TYPE: PRT
<213> ORGANISM: Penicillium sp. 'qii'

<400> SEQUENCE: 20

Ser Thr Ile Gln Pro Arg Ala Ser Gly Val Gln Gly Phe Asp Ile Ser
1               5                   10                  15

Ser Tyr Gln Gly Thr Val Asn Phe Ala Gly Ala Tyr Gly Ala Gly Ala
            20                  25                  30

Arg Phe Val Met Ile Lys Ala Thr Glu Gly Thr Thr Tyr Ile Asp Ser
        35                  40                  45

Thr Phe Ser Ser His Tyr Asp Gly Ala Thr Ser Ala Gly Leu Ile Arg
    50                  55                  60

Gly Ala Tyr His Phe Ala His Pro Asp Ser Ser Ser Gly Ala Thr Gln
65                  70                  75                  80

Ala Glu Tyr Phe Leu Ala His Gly Gly Gly Trp Thr Asn Asp Gly Ile
                85                  90                  95

Thr Leu Pro Gly Met Leu Asp Ile Glu Tyr Asn Pro Ser Gly Ser Thr
            100                 105                 110

Cys Tyr Gly Leu Ser Ala Ser Ala Met Val Ser Trp Ile Lys Asp Phe
        115                 120                 125
```

```
Gly Glu Thr Tyr Asn Ser Lys Thr Gly Arg Tyr Pro Met Ile Tyr Ser
        130                 135                 140

Thr Ala Asp Trp Trp Ser Thr Cys Thr Gly Asp Ser Thr Ser Phe Ser
145                 150                 155                 160

Ser Asp Tyr Pro Leu Val Leu Ala Gln Tyr Ala Ser Ser Ile Ser Thr
                165                 170                 175

Val Pro Gly Gly Trp Pro Tyr Gln Ser Phe Trp Gln Asn Ala Asp Ser
            180                 185                 190

Tyr Ser Tyr Gly Gly Asp Ser Asp Leu Trp Asn Gly Ser Glu Asp Ser
        195                 200                 205

Leu Lys Thr Phe Ala Lys Gly Ser
        210                 215

<210> SEQ ID NO 21
<211> LENGTH: 218
<212> TYPE: PRT
<213> ORGANISM: Aspergillus sp. nov XZ2609

<400> SEQUENCE: 21

Leu Pro Thr Lys Leu Ala Ala Arg Tyr Ser Thr Val Gln Gly Phe Asp
1               5                   10                  15

Val Ser Asn Tyr Gln Pro Asn Val Asp Phe Ser Ala Ala Lys Ser Ala
                20                  25                  30

Gly Ala Glu Phe Val Ile Ile Lys Ala Thr Glu Gly Thr Asp Tyr Lys
            35                  40                  45

Asp Thr Tyr Phe Asn Ser His Tyr Thr Gly Ala Thr Asn Ala Gly Leu
50                  55                  60

Ile Arg Gly Gly Tyr His Phe Ala Arg Pro Asp Lys Ser Ser Gly Thr
65                  70                  75                  80

Ala Gln Ala Glu Tyr Phe Leu Ala His Gly Gly Trp Ser Lys Asp
                85                  90                  95

Gly Arg Thr Leu Pro Gly Met Leu Asp Ile Glu Tyr Asn Pro Tyr Gly
            100                 105                 110

Ala Thr Cys Tyr Gly Leu Ser His Ser Ala Met Val Ser Trp Val Asn
        115                 120                 125

Glu Phe Leu Asn Glu Tyr His Ser Lys Thr Gly Val Tyr Pro Leu Leu
        130                 135                 140

Tyr Thr Thr Ala Asp Trp Trp Asn Gln Cys Thr Gly Asn Ala His Gly
145                 150                 155                 160

Phe Gly Asn Lys Ser Pro Leu Val Leu Ala Ser Tyr Ser Ser Glu Ser
                165                 170                 175

Pro Arg Thr Val Pro Gly Asp Trp Gln Thr Trp Thr Ile Trp Gln Asn
            180                 185                 190

Ala Asp Lys Tyr Lys Tyr Gly Gly Asp Ser Asp Ile Phe Asn Gly Asp
        195                 200                 205

Leu Thr Gln Leu Lys Lys Ile Val Glu Gly
        210                 215

<210> SEQ ID NO 22
<211> LENGTH: 204
<212> TYPE: PRT
<213> ORGANISM: Paecilomyces sp. XZ2658

<400> SEQUENCE: 22

Thr Val Ala Gly Phe Asp Ile Ser Asn Tyr Gln Pro Ser Val Asn Phe
1               5                   10                  15
```

```
Ala Lys Ala Tyr Ala Asp Gly Ala Arg Phe Ala Glu Gly Thr Thr
             20                  25                  30

Tyr Ile Asp Pro Ser Phe Ser His Tyr Thr Gly Ala Thr Asn Ala
             35                  40                  45

Gly Leu Ile Arg Gly Tyr His Phe Ala His Pro Gly Ser Ser Thr
 50                  55                  60

Gly Ala Ala Gln Ala Thr Tyr Phe Leu Ala His Gly Gly Trp Ser
 65                  70                  75                  80

Lys Asp Gly Ile Thr Leu Pro Gly Met Ile Asp Leu Glu Tyr Asn Pro
                 85                  90                  95

Ser Gly Ala Thr Cys Tyr Gly Leu Ser Thr Ser Ala Met Val Ser Trp
                100                 105                 110

Ile Ser Asp Phe Val Glu Thr Tyr His Ser Lys Thr Gly Val Tyr Pro
                115                 120                 125

Leu Ile Tyr Thr Ser Thr Ser Trp Trp Asn Gln Cys Thr Gly Ser Ser
 130                 135                 140

Thr Ala Phe Ala Ser Lys Cys Pro Leu Val Val Ala Arg Tyr Ala Ser
145                 150                 155                 160

Ser Val Gly Thr Leu Pro Ala Gly Trp Gly Tyr Gln Thr Ile Trp Gln
                165                 170                 175

Asn Ser Asp Ser Ser Pro Trp Gly Gly Asp Asn Asp Ile Phe Asn Gly
                180                 185                 190

Ser Leu Asp Gln Leu Lys Arg Ile Ala Asn Ala Ser
                195                 200

<210> SEQ ID NO 23
<211> LENGTH: 203
<212> TYPE: PRT
<213> ORGANISM: Paecilomyces sp. XZ2658

<400> SEQUENCE: 23

Ala Val Gln Gly His Asp Val Ser His Trp Gln Gly Asn Ile Asn Trp
 1               5                  10                  15

Gly Ala Val Lys Ala Ala Gly Val Lys Phe Thr Tyr Ile Lys Ala Thr
                 20                  25                  30

Glu Ser Thr Asn Tyr Ile Asp Pro Ser Phe Asn Ala Asn Tyr Val Gly
                 35                  40                  45

Ala Thr Asn Thr Gly Leu Ile Arg Gly Ala Tyr His Phe Ala Arg Pro
 50                  55                  60

Gly Asp Ser Ser Gly Ala Ala Gln Ala Asn Tyr Phe Val Ser His Gly
 65                  70                  75                  80

Gly Gly Trp Ser Ala Asp Gly Arg Thr Leu Pro Gly Ala Leu Asp Leu
                 85                  90                  95

Glu Ala Gly Cys Ser Gly Leu Ser Gln Ser Ala Met Thr Ala Trp Ile
                100                 105                 110

Arg Asp Phe Ser Asn Thr Tyr His Ala Arg Thr Gly Arg Phe Pro Val
                115                 120                 125

Ile Tyr Thr Thr Thr Ser Trp Trp Lys Thr Cys Thr Gly Asn Ala Ser
 130                 135                 140

Gly Phe Gln Asn Asp His Pro Leu Trp Ile Ala Arg Trp Gly Pro Ser
145                 150                 155                 160

Pro Gly Glu Leu Pro Ala Gly Tyr Gly Phe His Thr Phe Trp Gln Tyr
                165                 170                 175
```

Ala Asp Lys Gly Pro Leu Pro Gly Asp Gln Asp Asn Phe Asn Gly Asp
            180                 185                 190

Glu Ala Gly Leu Ala Arg Leu Ala Arg Gly Ser
            195                 200

<210> SEQ ID NO 24
<211> LENGTH: 208
<212> TYPE: PRT
<213> ORGANISM: Pycnidiophora cf dispera

<400> SEQUENCE: 24

Ala Val Ser Gly Met Asp Ile Ser His Tyr Gln Gly Thr Asn Tyr Asn
1               5                   10                  15

Phe Ala Gly Ala Tyr Ser Ser Gly Ala Arg Phe Val Ile Ile Lys Ala
            20                  25                  30

Thr Glu Gly Thr Thr Tyr Thr Asp Pro Gln Phe Ser Ala Asn Tyr Ile
        35                  40                  45

Gly Ala Thr Asn Ala Gly Phe Ile Arg Gly Ala Tyr His Phe Ala Arg
    50                  55                  60

Pro Ala Ala Ser Thr Gly Ala Val Gln Ala Ser Tyr Phe Val Ser His
65                  70                  75                  80

Gly Gly Gly Trp Ser Ser Asp Gly Ile Thr Leu Pro Gly Met Leu Asp
                85                  90                  95

Met Glu Tyr Gly Ser Thr Ser Thr Cys His Gly Leu Ser Val Ser Ala
            100                 105                 110

Met Asn Thr Trp Ile Ala Ser Phe Val Asn Gln Tyr Lys Ser Leu Thr
        115                 120                 125

Gly Ala Tyr Pro Met Ile Tyr Thr Thr Ala Asp Trp Trp Lys Thr Cys
    130                 135                 140

Thr Gly Asp Ser Thr Ala Trp Asn Thr Lys Cys Pro Leu Val Leu Ala
145                 150                 155                 160

Arg Tyr Ser Ser Ser Val Gly Thr Ile Pro Gly Gly Trp Pro Tyr His
                165                 170                 175

Thr Ile Trp Gln Tyr Ser Asp Ser Tyr Ala Tyr Gly Gly Asp Ser Asp
            180                 185                 190

Thr Phe Asn Gly Asp Leu Ala Gly Leu Lys Arg Leu Ala Lys Gly Ser
        195                 200                 205

<210> SEQ ID NO 25
<211> LENGTH: 210
<212> TYPE: PRT
<213> ORGANISM: Thermomucor indicae-seudaticae

<400> SEQUENCE: 25

Tyr Gln Thr Gly Leu Asp Val Ser Ala Leu Thr Ser Thr Ser Ser Phe
1               5                   10                  15

Ser Cys Ala Lys Asn Leu Gly Tyr Asp His Val Ile Ala Arg Cys Tyr
            20                  25                  30

Met Glu Ala Tyr Gly Asn Asn Pro Gly Gly Lys Val Asp Pro Asn Cys
        35                  40                  45

Tyr Ser Asn Tyr Lys Asn Ala Lys Ala Ala Gly Phe Thr Ser Val Asp
    50                  55                  60

Ile Tyr Met Phe Pro Cys Thr Gly Arg Ser Thr Cys Lys Ser Pro Ala
65                  70                  75                  80

Thr Gln Val Gln Glu Ile Val Asp Tyr Val Gly Ala His Lys Met Ile
                85                  90                  95

```
Val Gly Thr Leu Trp Leu Asp Val Glu Val Asp Ser Ala Ala Asn Asn
            100                 105                 110

Trp Pro Ser Thr Ser Glu Ala Arg Ser Thr Leu Arg Ala Phe Lys Thr
            115                 120                 125

Ala Leu Asp Lys Ser Gly Trp Lys Trp Gly Val Tyr Ser Ser Lys Ser
        130                 135                 140

Gln Trp Thr Arg Ile Thr Gly Ser Ala Ser Trp Val Leu Asp Pro Ser
145                 150                 155                 160

Val Pro Leu Trp Tyr Ser His Tyr Asp Asp Thr Leu Ser Phe Ser Asp
                165                 170                 175

Tyr Pro Ser His Ala Phe Gly Gly Trp Ser Lys Pro Thr Ile Lys Gln
            180                 185                 190

Tyr Thr Gly Asp Ala Ser Phe Cys Ser Ala Ser Trp Asp Lys Asn Tyr
        195                 200                 205

Tyr Gly
    210

<210> SEQ ID NO 26
<211> LENGTH: 207
<212> TYPE: PRT
<213> ORGANISM: Isaria farinosa

<400> SEQUENCE: 26

Leu Thr His Ala Val Asp Ser Ser Glu Val Ser Val Asp Ile Tyr
1               5                   10                  15

Lys Lys Ala Leu Gly Gln Gly Phe Thr Arg Ala Ile Phe Arg Gly Tyr
            20                  25                  30

Gln Glu Ala Cys Ser Leu Gly Gly Arg Val Asp Pro Thr Phe Val Pro
        35                  40                  45

Ser Tyr Lys Asn Ala Val Ala Ala Gly Tyr Lys Asp Phe Asp Ala Tyr
    50                  55                  60

Phe Phe Pro Cys Thr Gly Thr Thr Asn Lys Cys Lys Pro Tyr Ala Thr
65                  70                  75                  80

Gln Leu Ala Glu Leu Leu Asp Thr Ile Ser Ser Gln Lys Leu Ala Ile
                85                  90                  95

Arg Arg Ile Trp Leu Asp Ile Glu Thr Asp Gln Val Cys Ser Pro Phe
            100                 105                 110

Asp Tyr Gly Ala Gln Gly Asn Ile Ala Glu Ala Lys Lys Leu Val Ala
        115                 120                 125

Ala Phe Arg Ala Ala Lys His Asp Trp Gly Ile Tyr Thr Ser Pro Thr
    130                 135                 140

Gln Trp Glu Thr Ile Phe Gly Ser Lys Thr Phe Val Leu Ala Asn Asp
145                 150                 155                 160

Val Pro Leu Trp Phe Ala Lys Phe Asp Asn Val Glu Thr Leu Asp Leu
                165                 170                 175

Lys Thr Pro Phe Gly Gly Trp Thr Lys Ala Asp Ala Lys Gln Tyr Thr
            180                 185                 190

Asp Gln Ser Ala Ser Lys Lys Phe Asp Leu Asn Val Phe Ser Ala
        195                 200                 205

<210> SEQ ID NO 27
<211> LENGTH: 207
<212> TYPE: PRT
<213> ORGANISM: Lecanicillium sp. WMM742
```

<400> SEQUENCE: 27

```
Ser Val Gln Gly Phe Asp Ile Ser His Tyr Gln Ser Val Asn Phe
1               5                   10                  15

Gly Ala Ala Tyr Ala Asp Gly Ala Arg Phe Val Ile Ile Lys Ala Thr
            20                  25                  30

Glu Gly Thr Thr Tyr Arg Asp Pro Lys Phe Ser Glu His Tyr Gly Gly
        35                  40                  45

Ala Thr Lys Ala Gly Phe Ile Arg Gly Gly Tyr His Phe Ala Gln Pro
    50                  55                  60

Ala Ser Ser Ser Gly Ala Ala Gln Ala Asn Phe Phe Leu Ala His Gly
65                  70                  75                  80

Gly Gly Trp Ser Gly Asp Gly Ile Thr Leu Pro Gly Met Leu Asp Leu
                85                  90                  95

Glu Tyr Gly Pro Asn Gly Asn Thr Cys Tyr Gly Leu Gly Pro Ala Ser
            100                 105                 110

Met Arg Ser Trp Ile Ser Asp Phe Val Glu Thr Tyr His Ala Lys Thr
        115                 120                 125

Gly Arg Tyr Pro Leu Ile Tyr Thr Ser Thr Ser Trp Trp Lys Thr Cys
    130                 135                 140

Thr Gly Asn Thr Ser Leu Phe Ala Asp Lys Cys Pro Leu Val Val Ala
145                 150                 155                 160

Arg Tyr Asn Ser Gln Val Gly Glu Leu Pro Ala Gly Trp Gly Phe Tyr
                165                 170                 175

Thr Phe Trp Gln Phe Asn Asp His Tyr Lys His Gly Gly Asp Ser Asp
            180                 185                 190

Val Phe Asn Gly Ala Tyr Ser Gln Leu Gln Lys Ile Ala Thr Gly
        195                 200                 205
```

<210> SEQ ID NO 28
<211> LENGTH: 208
<212> TYPE: PRT
<213> ORGANISM: Zopfiella sp. t180-6

<400> SEQUENCE: 28

```
Ala Val Gln Gly Phe Asp Val Ser His Trp Gln Ser Ser Val Asn Phe
1               5                   10                  15

Ala Ala Ala Tyr Asn Ser Gly Ala Arg Phe Val Ile Ile Lys Ala Thr
            20                  25                  30

Glu Ser Asn Asn Tyr Ile Asp Pro Lys Phe Asn Thr Tyr Tyr Pro Ala
        35                  40                  45

Ala Thr Ser Ala Gly Leu Ile Arg Gly Gly Tyr His Phe Ala His Pro
    50                  55                  60

Gly Glu Thr Thr Gly Ala Val Gln Ala Asp Tyr Phe Ile Ala His Gly
65                  70                  75                  80

Gly Gly Trp Ser Ser Asp Gly Ile Thr Leu Pro Gly Met Leu Asp Leu
                85                  90                  95

Glu Asn Ala Ser Gly Tyr Pro Ala Cys Trp Gly Leu Ser Gln Ser Ala
            100                 105                 110

Met Val Ser Trp Ile Lys Ala Phe Ser Asp Arg Tyr Lys Ala Arg Thr
        115                 120                 125

Gly Val Tyr Pro Met Leu Tyr Thr Asn Pro Ser Trp Trp Thr Ser Cys
    130                 135                 140

Thr Gly Asn Ser Asn Ala Phe Val Asn Thr Asn Pro Leu Val Leu Ala
145                 150                 155                 160
```

```
Arg Tyr Ala Ser Ser Pro Gly Thr Ile Pro Gly Gly Trp Pro Tyr Gln
                165                 170                 175

Thr Ile Trp Gln Asn Ser Asp Ser Tyr Thr Tyr Gly Gly Asp Ser Asp
            180                 185                 190

Ile Phe Asn Gly Asp Leu Ala Gly Leu Lys Arg Leu Ala Lys Gly Ser
        195                 200                 205

<210> SEQ ID NO 29
<211> LENGTH: 217
<212> TYPE: PRT
<213> ORGANISM: Malbranchea flava

<400> SEQUENCE: 29

Gly Pro Lys Glu Phe Glu Ser Arg Ala Ser Gly Val Gln Gly Phe Asp
1               5                   10                  15

Ile Ser Gly Trp Gln Ser Asn Val Asn Phe Ala Gly Ala Tyr Asn Ser
            20                  25                  30

Gly Ala Arg Phe Val Met Ile Lys Ala Ser Glu Gly Thr Thr Phe Lys
        35                  40                  45

Asp Arg Gln Phe Ser Asn His Tyr Ile Gly Ala Thr Lys Ala Gly Phe
50                  55                  60

Ile Arg Gly Gly Tyr His Phe Ala Leu Pro Asp Val Ser Ser Ala Thr
65                  70                  75                  80

Ala Gln Val Asn His Phe Leu Ala Ser Gly Gly Trp Ser Arg Asp
                85                  90                  95

Gly Ile Thr Leu Pro Gly Met Leu Asp Ile Glu Ser Asn Pro Tyr Gly
            100                 105                 110

Ala Gln Cys Tyr Gly Leu Asp Ala Gly Arg Met Val Ala Trp Ile Arg
        115                 120                 125

Glu Phe Val Asp Ala Tyr Lys Arg Ala Thr Gly Arg Tyr Pro Leu Ile
130                 135                 140

Tyr Thr Ser Pro Ser Trp Trp Gln Thr Cys Thr Gly Asn Ser Asn Ala
145                 150                 155                 160

Phe Ile Asp Lys Cys Pro Leu Val Leu Ala Arg Trp Ala Ser Ser Pro
                165                 170                 175

Gly Thr Pro Pro Gly Gly Trp Pro Phe His Ser Phe Trp Gln Tyr Ala
            180                 185                 190

Asp Ser Tyr Gln Phe Gly Gly Asp Ala Gln Val Phe Asn Gly Asp Glu
        195                 200                 205

Ala Gly Leu Lys Arg Met Ala Leu Gly
    210                 215

<210> SEQ ID NO 30
<211> LENGTH: 208
<212> TYPE: PRT
<213> ORGANISM: Hypholoma polytrichi

<400> SEQUENCE: 30

Leu Val Tyr Gly Val Asp Ser Ser Leu Val Pro Val Ala Thr Tyr
1               5                   10                  15

Gln Lys Ala Leu Gly Glu Gly Phe Thr Lys Ala Val Ile Arg Gly Tyr
            20                  25                  30

Glu Glu Ala Cys Gly Val Gly Gly Glu Val Asp Pro Asn Phe Val Pro
        35                  40                  45

Ser Tyr Lys Asn Ala Arg Ala Ala Gly Tyr Thr Asp Ile Asp Met Tyr
50                  55                  60
```

-continued

Trp Phe Pro Cys Asn Gly Ser Thr His Ser Cys Lys Ser Tyr Ala Ala
65                  70                  75                  80

Gln Leu Ala Ala Ile Ala Ala Phe Ser Ala Asn Ala Met Lys Ile
            85                  90                  95

Gly Thr Ile Trp Ile Asp Ile Glu Lys Asp Ala Ala Ile Cys Asn Asn
            100                 105                 110

Trp Asp Tyr Gly Thr Ala Gly Asn Leu Ala Gln Ala Lys Ala Leu Ile
            115                 120                 125

Ala Ala Ala Lys Ala Ser Gly Phe Asn Phe Gly Ile Tyr Ser Ser Pro
130                 135                 140

Gly Glu Trp Ser Thr Ile Phe Gly Ser Thr Ser Val Val Asp Asn
145                 150                 155                 160

Ser Ala Pro Leu Trp Phe Ala Thr Tyr Asn Asn Val Gln Thr Leu Thr
                165                 170                 175

Leu Gly Thr Pro Phe Gly Gly Trp Ser Thr Ala Val Gly His Gln Tyr
            180                 185                 190

Thr Asp Val Ser Ala Ser Gly Leu Phe Asp Leu Asn Val Phe Ala His
            195                 200                 205

<210> SEQ ID NO 31
<211> LENGTH: 201
<212> TYPE: PRT
<213> ORGANISM: Aspergillus deflectus

<400> SEQUENCE: 31

Ala Val Gln Gly Phe Asp Ile Ser His Tyr Gln Ser Ser Val Asp Tyr
1               5                   10                  15

Ala Gly Ala Tyr Ser Ser Gly Ala Arg Phe Val Met Ile Lys Ala Thr
            20                  25                  30

Glu Gly Thr Thr Tyr Thr Asp Pro Ala Phe Ser Thr His Tyr Thr Gly
            35                  40                  45

Ala Thr Asn Ala Gly Leu Ile Arg Gly Gly Tyr His Phe Ala Arg Pro
50                  55                  60

Gly Ser Ser Ser Gly Ala Ala Gln Ala Glu Tyr Phe Leu Ala His Gly
65                  70                  75                  80

Gly Gly Trp Thr Gly Asp Gly Ile Thr Leu Pro Gly Met Leu Asp Leu
            85                  90                  95

Glu Ala Gly Cys Ser Gly Leu Ser Ala Ser Ala Met Val Ser Trp Ile
            100                 105                 110

Gln Asp Phe Gly Glu Thr Tyr Lys Ala Ser Thr Gly Arg Tyr Pro Met
            115                 120                 125

Ile Tyr Thr Thr Thr Ser Trp Trp Ser Ser Cys Thr Gly Asn Asn Gly
            130                 135                 140

Gly Phe Gly Asp Tyr Pro Leu Val Leu Ala Arg Trp Ala Ser Ser Pro
145                 150                 155                 160

Gly Glu Leu Pro Asn Gly Trp Ser Val His Ser Phe Trp Gln Asn Ala
                165                 170                 175

Asp Thr Tyr Glu Tyr Gly Gly Asp Ser Glu Ile Trp Asn Gly Ser Gln
            180                 185                 190

Glu Asn Leu Val Lys Phe Ala Ser Gln
            195                 200

<210> SEQ ID NO 32
<211> LENGTH: 202
<212> TYPE: PRT

<213> ORGANISM: Ascobolus stictoideus

<400> SEQUENCE: 32

Ala Val Pro Gly Phe Asp Ile Ser His Tyr Gln Ser Thr Val Asn Phe
1               5                   10                  15

Ala Asp Ala Tyr Ser Ser Gly Ala Arg Phe Val Ile Ile Lys Ala Thr
            20                  25                  30

Glu Gly Thr Thr Tyr Lys Asp Pro Lys Phe Ser Ser His Tyr Thr Gly
        35                  40                  45

Ala Thr Asn Ala Gly Leu Ile Arg Gly Gly Tyr His Phe Ala Arg Pro
    50                  55                  60

Ala Ser Ser Thr Gly Ala Val Gln Ala Gln Tyr Phe Val Ser Asn Gly
65                  70                  75                  80

Gly Gly Trp Ser Gly Asp Gly Leu Thr Leu Pro Gly Met Leu Asp Leu
                85                  90                  95

Glu Gly Asp Cys Ala Gly Leu Ser Gln Ala Gly Met Val Ser Trp Ile
            100                 105                 110

Thr Ser Phe Val Asn Lys Tyr Lys Ala Leu Thr Thr Arg Tyr Pro Met
        115                 120                 125

Ile Tyr Thr Thr Asn Ser Trp Trp Asn Thr Cys Thr Gly Asn Ser Gln
130                 135                 140

Ala Phe Ser Ala Asn Cys Pro Leu Val Ile Ala Arg Tyr Asn Ser Val
145                 150                 155                 160

Val Gly Thr Ile Pro Gly Gly Trp Pro Tyr Tyr Thr Ile Trp Gln Phe
                165                 170                 175

Asn Asp Ala Tyr Ser Tyr Gly Gly Asp Ser Asp Thr Phe Asn Gly Ala
            180                 185                 190

Tyr Ser Gln Leu Val Lys Leu Ala Thr Gly
        195                 200

<210> SEQ ID NO 33
<211> LENGTH: 207
<212> TYPE: PRT
<213> ORGANISM: Coniochaeta sp

<400> SEQUENCE: 33

Thr Val Gln Gly Phe Asp Ile Ser His Tyr Gln Pro Thr Val Asn Tyr
1               5                   10                  15

Ala Gly Ala Tyr Asn Ala Gly Ala Arg Phe Val Ile Ile Lys Ala Thr
            20                  25                  30

Glu Gly Thr Thr Tyr Thr Asp Pro Ser Phe Ser Thr His Tyr Asn Gly
        35                  40                  45

Ala Thr Lys Ala Gly Leu Ile Arg Gly Gly Tyr His Phe Ala His Pro
    50                  55                  60

Gly Val Thr Thr Gly Ala Ala Glu Ala Asn Phe Phe Leu Ala His Gly
65                  70                  75                  80

Gly Gly Trp Ser Gly Asp Gly Ile Thr Leu Pro Gly Met Leu Asp Leu
                85                  90                  95

Glu Ser Glu Gly Ser Asn Pro Gln Cys Trp Gly Leu Ser Thr Ser Gly
            100                 105                 110

Met Val Ala Trp Ile Lys Ser Phe Ser Asp Arg Tyr His Thr Val Thr
        115                 120                 125

Gly Arg Tyr Pro Met Leu Tyr Thr Asn Pro Ser Trp Trp Ser Thr Cys
130                 135                 140

-continued

```
Thr Gly Asn Ser Asn Ala Phe Val Asn Thr Asn Pro Leu Val Leu Ala
145                 150                 155                 160

Arg Tyr Ala Ser Ala Pro Gly Thr Ile Pro Gly Gly Trp Pro Tyr Gln
            165                 170                 175

Thr Ile Trp Gln Asn Ser Asp Ser Tyr Ser Tyr Gly Gly Asp Ser Asp
        180                 185                 190

Ile Phe Asn Gly Asn Leu Ala Ser Leu Gln Lys Leu Ala Thr Gly
            195                 200                 205

<210> SEQ ID NO 34
<211> LENGTH: 202
<212> TYPE: PRT
<213> ORGANISM: Daldinia fissa

<400> SEQUENCE: 34

Ala Val Pro Gly Phe Asp Ile Ser His Tyr Gln Ser Ser Val Asp Phe
1               5                   10                  15

Gly Ala Ala Tyr Ser Ser Gly Ala Arg Phe Val Ile Ile Lys Ala Thr
            20                  25                  30

Glu Gly Thr Thr Tyr Gln Asp Pro Lys Phe Ser Ser His Tyr Ala Gly
        35                  40                  45

Ala Thr Asn Ala Gly Leu Ile Arg Gly Gly Tyr His Phe Ala Arg Pro
    50                  55                  60

Ala Ser Ser Ser Gly Ala Ala Gln Ala Thr Phe Phe Leu Ala His Gly
65                  70                  75                  80

Gly Gly Trp Ser Gly Asp Gly Ile Thr Leu Pro Gly Met Leu Asp Leu
                85                  90                  95

Glu Gly Asp Cys Ala Gly Leu Ser Thr Ser Ala Met Val Ser Trp Ile
            100                 105                 110

Arg Asp Phe Ser Asp Thr Tyr His Gly Lys Thr Gly Arg Tyr Pro Leu
        115                 120                 125

Leu Tyr Thr Asn Pro Ser Trp Trp Ser Ser Cys Thr Gly Gly Ser Ser
    130                 135                 140

Ala Phe Val Asn Thr Asn Pro Leu Val Leu Ala Arg Tyr Ala Ser Ser
145                 150                 155                 160

Pro Gly Ala Leu Pro Gly Gly Trp Pro Tyr Tyr Thr Ile Trp Gln Phe
            165                 170                 175

Asn Asp Ala Tyr Lys Tyr Gly Asp Ser Asp Thr Phe Asn Gly Asp
        180                 185                 190

Leu Thr Gln Leu Lys Lys Leu Ala Ser Gly
    195                 200

<210> SEQ ID NO 35
<211> LENGTH: 201
<212> TYPE: PRT
<213> ORGANISM: Rosellinia sp

<400> SEQUENCE: 35

Ala Val Gln Gly Phe Asp Ile Ser His Tyr Gln Ser Ser Val Asn Phe
1               5                   10                  15

Ala Gly Ala Tyr Ser Ala Gly Ala Arg Phe Val Ile Ile Lys Ala Thr
            20                  25                  30

Glu Gly Thr Ser Tyr Ile Asp Pro Lys Phe Ser Ser His Tyr Ile Gly
        35                  40                  45

Ala Thr Asn Ala Gly Leu Ile Arg Gly Gly Tyr His Phe Ala His Leu
    50                  55                  60
```

```
Gly Ser Ser Gly Ala Ala Gln Ala Asn Tyr Phe Leu Ala His Gly
 65                  70                  75                  80

Gly Gly Trp Ser Gly Asp Gly Ile Thr Leu Pro Gly Met Leu Asp Leu
                 85                  90                  95

Glu Gly Asp Cys Val Leu Ser Ala Ser Gly Ala Val Ala Trp Ile Lys
            100                 105                 110

Asp Phe Ser Asp Thr Tyr His Ser Lys Thr Gly Val Tyr Pro Leu Leu
            115                 120                 125

Tyr Thr Asn Pro Ser Trp Trp Ser Ser Cys Thr Gly Asn Ser Asn Ala
            130                 135                 140

Phe Val Asn Thr Asn Pro Leu Val Leu Ala Arg Tyr Ser Ser Ser Ala
145                 150                 155                 160

Gly Thr Pro Pro Gly Gly Trp Pro Tyr Tyr Thr Ile Trp Gln Tyr Asn
                165                 170                 175

Asp Ala Tyr Ala Tyr Gly Gly Asp Ser Asp Val Phe Asn Gly Asp Met
            180                 185                 190

Ala Gly Leu Leu Arg Leu Ala Lys Gly
            195                 200

<210> SEQ ID NO 36
<211> LENGTH: 202
<212> TYPE: PRT
<213> ORGANISM: Ascobolus sp. ZY179

<400> SEQUENCE: 36

Ala Val Pro Gly Phe Asp Ile Ser His Trp Gln Ser Ser Val Asn Phe
1               5                   10                  15

Ala Ser Ala Tyr Ser Ser Gly Ala Arg Phe Val Ile Ile Lys Ala Thr
            20                  25                  30

Glu Gly Thr Thr Tyr Lys Asp Pro Lys Phe Ser Ser His Tyr Thr Gly
            35                  40                  45

Ala Thr Lys Ala Gly Phe Ile Arg Gly Gly Tyr His Phe Ala Arg Pro
        50                  55                  60

Ala Ser Ser Thr Gly Ala Ala Gln Ala Gln Phe Phe Ala Ser Asn Gly
 65                 70                  75                  80

Gly Gly Trp Ser Gly Asp Gly Ile Thr Leu Pro Gly Met Leu Asp Leu
                85                  90                  95

Glu Gly Asp Cys Ala Gly Leu Ser Gln Ser Gly Met Val Ser Trp Ile
            100                 105                 110

Ser Ser Phe Val Asn Lys Tyr Arg Ser Leu Thr Gly Arg Tyr Pro Met
            115                 120                 125

Ile Tyr Thr Thr Asn Ser Trp Trp Val Thr Cys Thr Gly Asn Ser Lys
            130                 135                 140

Ala Phe Ser Ser Asn Cys Pro Leu Val Ile Ala Arg Tyr Asn Ser Val
145                 150                 155                 160

Val Gly Thr Ile Pro Gly Gly Trp Pro Tyr Tyr Thr Ile Trp Gln Tyr
                165                 170                 175

Asn Asp Ala Tyr Lys Tyr Gly Gly Asp Ser Asp Thr Phe Asn Gly Ala
            180                 185                 190

Tyr Ser Gln Leu Val Lys Leu Ala Thr Gly
            195                 200

<210> SEQ ID NO 37
<211> LENGTH: 206
<212> TYPE: PRT
```

<213> ORGANISM: Curreya sp. XZ2623

<400> SEQUENCE: 37

Thr Val Pro Gly Phe Asp Ile Ser His Tyr Gln Gly Thr Val Asn Phe
1               5                   10                  15

Ala Gly Ala Tyr Ser Ser Gly Ala Arg Phe Val Ile Ile Lys Ala Thr
            20                  25                  30

Glu Gly Thr Thr Tyr Thr Asp Pro Asn Phe Ser Asn Asn Tyr Val Gly
        35                  40                  45

Ala Thr Asn Ala Lys Phe Ile Arg Gly Ala Tyr His Phe Ala Arg Pro
    50                  55                  60

Asp Gly Gly Ser Gly Ser Thr Gln Ala Gln Phe Phe His Ser His Gly
65                  70                  75                  80

Gly Gly Trp Ser Gly Asp Gly Ile Thr Leu Pro Gly Met Leu Asp Ile
                85                  90                  95

Glu Tyr Gly Pro Thr Ser Thr Cys Tyr Gly Leu Ser Thr Ser Ala Met
            100                 105                 110

Val Thr Trp Ile Thr Asp Phe Val Asn Glu Tyr His Ala Leu Thr Gly
        115                 120                 125

Arg Tyr Pro Leu Ile Tyr Thr Thr Asn Asp Trp Trp Asn Thr Cys Thr
130                 135                 140

Gly Asn Thr Asn Lys Phe Ser Thr Thr Cys Pro Leu Val Leu Ala Arg
145                 150                 155                 160

Tyr Ser Ser Ser Val Gly Thr Ile Pro Gly Gly Trp Pro Phe Gln Thr
                165                 170                 175

Ile Trp Gln Phe Asn Asp Asn Tyr Ala Tyr Gly Gly Asp Ser Asp Thr
            180                 185                 190

Phe Asn Gly Asp Leu Ala Gly Leu Lys Lys Leu Ala Thr Gly
        195                 200                 205

<210> SEQ ID NO 38
<211> LENGTH: 202
<212> TYPE: PRT
<213> ORGANISM: Coniothyrium sp

<400> SEQUENCE: 38

Ala Val Gln Gly Phe Asp Ile Ser His Tyr Gln Ala Ser Val Asn Phe
1               5                   10                  15

Ala Ala Ala Tyr Ser Gly Gly Leu Arg Phe Val Tyr Ile Lys Ala Thr
            20                  25                  30

Glu Gly Thr Thr Tyr Gln Asp Pro Ala Phe Ser Ser His Tyr Ser Gly
        35                  40                  45

Ala Thr Ser Ala Gly Phe Ile Arg Gly Gly Tyr His Phe Ala Arg Pro
    50                  55                  60

Ala Ser Ser Thr Gly Ala Ala Gln Ala Ser Tyr Phe Val Ala His Gly
65                  70                  75                  80

Gly Gly Trp Ser Asn Asp Gly Ile Thr Leu Pro Gly Met Leu Asp Leu
                85                  90                  95

Glu Gly Asp Cys Ala Gly Leu Ser Thr Ala Ser Met Val Ser Trp Ile
            100                 105                 110

Ser Ser Phe Ser Asn Gln Tyr His Ser Leu Thr Gly Arg Trp Pro Val
        115                 120                 125

Ile Tyr Thr Thr Asn Ser Trp Trp Thr Thr Cys Thr Gly Asn Ser Ala
130                 135                 140

```
Ala Phe Asn Ala Asn Ser Pro Leu Met Leu Ala Arg Trp Gly Ser Thr
145                 150                 155                 160

Ala Gly Thr Ile Pro Gly Gly Trp Pro Tyr Tyr Thr Ile Trp Gln Tyr
                165                 170                 175

Lys Asp Ser Asn Thr Tyr Gly Gly Asp Ser Asp Val Phe Asn Gly Asp
            180                 185                 190

Ala Thr Gln Leu Lys Lys Leu Ala Thr Gly
        195                 200
```

<210> SEQ ID NO 39
<211> LENGTH: 202
<212> TYPE: PRT
<213> ORGANISM: Hypoxylon sp

<400> SEQUENCE: 39

```
Ala Val Pro Gly Phe Asp Ile Ser His Tyr Gln Ser Asn Val Asp Phe
1               5                   10                  15

Gly Ala Ala Tyr Ser Ser Gly Ala Arg Phe Val Ile Ile Lys Ala Thr
                20                  25                  30

Glu Gly Thr Thr Tyr Gln Asp Pro Ser Phe Ser Thr His Tyr Thr Gly
            35                  40                  45

Ala Thr Lys Ala Gly Leu Ile Arg Gly Ser Tyr His Phe Ala Arg Pro
50                  55                  60

Gly Ser Ser Ser Gly Ala Ala Gln Ala Thr Tyr Phe Leu Ala His Gly
65                  70                  75                  80

Gly Gly Trp Ser Gly Asp Gly Ile Thr Leu Pro Gly Met Leu Asp Leu
                85                  90                  95

Glu Gly Asp Cys Ala Gly Leu Ser Thr Asn Ala Met Val Ala Trp Ile
            100                 105                 110

Arg Asp Phe Ser Asp Thr Tyr His Gly Arg Thr Gly Arg Tyr Pro Leu
            115                 120                 125

Leu Tyr Thr Asn Pro Ser Trp Trp Ser Gly Cys Ala Gly Gly Ser Ala
        130                 135                 140

Ala Phe Val Gly Thr Asn Pro Leu Val Leu Ala Arg Tyr Ala Gly Ser
145                 150                 155                 160

Pro Gly Ala Leu Pro Gly Gly Trp Pro Tyr Tyr Thr Ile Trp Gln Phe
                165                 170                 175

Asp Asp Ala Tyr Lys Tyr Gly Gly Asp Ser Asp Thr Phe Asn Gly Asp
            180                 185                 190

Leu Thr Gln Leu Lys Lys Leu Ala Ser Gly
        195                 200
```

<210> SEQ ID NO 40
<211> LENGTH: 202
<212> TYPE: PRT
<213> ORGANISM: Xylariaceae sp. 1653h

<400> SEQUENCE: 40

```
Ala Val Pro Gly Phe Asp Ile Ser His Tyr Gln Ser Ser Val Asp Phe
1               5                   10                  15

Ala Ala Ala Tyr Ser Ala Gly Ala Arg Phe Val Ile Ile Lys Ala Thr
                20                  25                  30

Glu Gly Thr Thr Tyr Ile Asp Pro Ser Phe Ser His Tyr Thr Gly
            35                  40                  45

Ala Thr Asn Ala Gly Leu Ile Arg Gly Gly Tyr His Phe Ala His Pro
50                  55                  60
```

Gly Ser Ser Ser Gly Ala Thr Gln Ala Asn Tyr Phe Leu Ala His Gly
65                  70                  75                  80

Gly Gly Trp Ser Gly Asp Gly Ile Thr Leu Pro Gly Met Leu Asp Leu
            85                  90                  95

Glu Gly Asp Cys Ala Gly Leu Ser Thr Ser Ala Met Val Ser Trp Ile
                100                 105                 110

Lys Asp Phe Ser Asn Ala Tyr His Ser Lys Thr Gly Arg Tyr Pro Leu
            115                 120                 125

Leu Tyr Thr Asn Pro Ser Trp Trp Ser Ser Cys Thr Gly Ser Ser Ser
        130                 135                 140

Ala Phe Val Asn Thr Asn Pro Leu Val Leu Ala Arg Tyr Ser Ser Ser
145                 150                 155                 160

Ala Gly Thr Pro Pro Gly Gly Trp Pro Tyr Tyr Thr Ile Trp Gln Phe
                165                 170                 175

Asn Asp Ala Tyr Lys Tyr Gly Gly Asp Ser Asp Thr Phe Asn Gly Glu
            180                 185                 190

Tyr Ala Ser Leu Gln Lys Leu Ala Thr Gly
        195                 200

<210> SEQ ID NO 41
<211> LENGTH: 202
<212> TYPE: PRT
<213> ORGANISM: Hypoxylon sp

<400> SEQUENCE: 41

Ala Val Pro Gly Phe Asp Ile Ser His Tyr Gln Ser Ser Val Asp Phe
1               5                   10                  15

Ala Ala Ala Tyr Asn Ser Gly Ala Arg Phe Val Ile Ile Lys Ala Thr
            20                  25                  30

Glu Gly Thr Thr Tyr Ile Asp Pro Ser Phe Ser Ser His Tyr Thr Gly
        35                  40                  45

Ala Thr Lys Ala Gly Phe Ile Arg Gly Gly Tyr His Phe Ala His Pro
    50                  55                  60

Gly Ser Ser Ser Gly Ala Ala Gln Ala Asn Tyr Phe Leu Ala His Gly
65                  70                  75                  80

Gly Gly Trp Ser Gly Asp Gly Ile Thr Phe Pro Gly Met Leu Asp Leu
            85                  90                  95

Glu Gly Asp Cys Ala Gly Leu Ser Thr Ser Ala Met Val Ser Trp Ile
                100                 105                 110

Lys Asp Phe Ser Asp Thr Tyr His Ser Lys Thr Gly Arg Tyr Pro Leu
            115                 120                 125

Leu Tyr Thr Asn Pro Ser Trp Trp Ser Ser Cys Thr Gly Asp Ser Ser
        130                 135                 140

Ala Phe Val Asn Thr Asn Pro Leu Val Leu Ala Arg Tyr Ser Ser Ser
145                 150                 155                 160

Ala Gly Thr Pro Pro Gly Gly Trp Pro Tyr Tyr Thr Ile Trp Gln Phe
                165                 170                 175

Asn Asp Ala Tyr Lys Tyr Gly Gly Asp Ser Asp Thr Phe Asn Gly Asn
            180                 185                 190

Tyr Ala Ser Leu Gln Lys Leu Ala Thr Gly
        195                 200

<210> SEQ ID NO 42
<211> LENGTH: 206
<212> TYPE: PRT

<213> ORGANISM: Yunnania penicillata

<400> SEQUENCE: 42

Asp Val Asp Gly Phe Asp Ile Ser His Tyr Gln Glu Thr Val Asp Tyr
1               5                   10                  15

Ala Gly Ala Tyr Gly Ala Gly Arg Phe Val Ile Ile Lys Ala Thr
            20                  25                  30

Glu Gly Thr Asn Tyr Ile Asp Ser Ser Phe Asn Thr His Tyr Ala Gly
            35                  40                  45

Ala Thr Asp Ala Gly Leu Ile Arg Gly Gly Tyr His Phe Ala His Pro
        50                  55                  60

Gly Glu Thr Thr Gly Ala Glu Gln Ala Asp Tyr Phe Ala His Gly
65                  70                  75                  80

Gly Asn Trp Ser Asn Asp Gly Ile Thr Leu Pro Gly Met Leu Asp Leu
                85                  90                  95

Glu Gly Glu Gly Ser Thr Thr Cys Trp Asp Leu Ser Ala Ala Asp Met
            100                 105                 110

Val Ala Trp Ile Lys Ala Phe Ser Asp Arg Tyr Gln Glu Val Thr Ser
            115                 120                 125

Arg Tyr Pro Leu Leu Tyr Thr Asn Pro Ser Trp Ser Glu Cys Thr
130                 135                 140

Gly Asn Ser Asp Ala Phe Val Asp Thr Asn Pro Leu Val Leu Ala Arg
145                 150                 155                 160

Tyr Ala Ser Ser Pro Gly Glu Ile Pro Gly Gly Trp Pro Ala Gln Thr
                165                 170                 175

Ile Trp Gln Asn Ser Asp Ser Tyr Ser Phe Gly Gly Asp Ser Asp Ile
            180                 185                 190

Phe Asn Gly Asp Glu Ala Gly Leu Lys Lys Leu Ala Ser Gly
            195                 200                 205

<210> SEQ ID NO 43
<211> LENGTH: 207
<212> TYPE: PRT
<213> ORGANISM: Engyodontium album

<400> SEQUENCE: 43

Arg Val Gln Gly Phe Asp Ile Ser His Tyr Gln Pro Ser Val Asp Phe
1               5                   10                  15

Asn Ala Ala Tyr Ala Asp Gly Ala Arg Phe Val Ile Ile Lys Ala Thr
            20                  25                  30

Glu Gly Thr Thr Tyr Lys Asp Pro Lys Phe Ser Gln His Tyr Ile Gly
            35                  40                  45

Ala Thr Asn Ala Gly Phe Ile Arg Gly Gly Tyr His Phe Ala Gln Pro
        50                  55                  60

Ala Ser Ser Ser Gly Ala Ala Gln Ala Asp Tyr Phe Leu Lys Asn Gly
65                  70                  75                  80

Gly Gly Trp Ser Ser Asp Gly Ile Thr Leu Pro Gly Met Leu Asp Met
                85                  90                  95

Glu Tyr Asn Pro Asn Gly Ser Ala Cys Tyr Gly Leu Ser Gln Ala Ser
            100                 105                 110

Met Arg Asn Trp Ile Asn Asp Phe Val Asn Thr Tyr His Ser Arg Thr
            115                 120                 125

Gly Val Tyr Pro Leu Leu Tyr Thr Thr Thr Ser Trp Trp Lys Thr Cys
130                 135                 140

```
Thr Gly Asn Thr Ala Met Phe Ala Asp Lys Cys Pro Leu Val Ile Ala
145                 150                 155                 160

Arg Tyr Asn Ser Val Val Gly Glu Leu Pro Ala Gly Trp Ser Phe Trp
                165                 170                 175

Thr Ile Trp Gln Tyr Asn Asp His Tyr Lys His Gly Gly Asp Ser Asp
            180                 185                 190

Ala Phe Asn Gly Asp Tyr Ser Gln Leu Gln Arg Ile Ala Arg Gly
        195                 200                 205

<210> SEQ ID NO 44
<211> LENGTH: 208
<212> TYPE: PRT
<213> ORGANISM: Metapochonia bulbillosa

<400> SEQUENCE: 44

Thr Val Ala Gly Phe Asp Ile Ser Asn Tyr Gln Pro Thr Val Asp Phe
1               5                   10                  15

Lys Lys Ala Tyr Ala Asp Gly Ala Arg Phe Val Ile Ile Lys Ala Thr
                20                  25                  30

Glu Gly Thr Thr Tyr Thr Asp Pro Ser Phe Ser Ser His Tyr Thr Gly
            35                  40                  45

Ala Thr Gln Ala Gly Leu Ile Arg Gly Gly Tyr His Phe Ala His Pro
        50                  55                  60

Gly Ser Gly Thr Gly Ala Ala Gln Ala Asn Tyr Phe Leu Ala His Gly
65                  70                  75                  80

Gly Gly Trp Ser Lys Asp Gly Ile Thr Leu Pro Gly Met Ile Asp Leu
                85                  90                  95

Glu Tyr Asn Pro Ser Gly Ala Thr Cys Tyr Gly Leu Ser Ala Ser Gly
            100                 105                 110

Met Val Ser Trp Ile Ser Asp Phe Val Glu Thr Tyr His Ser Lys Thr
        115                 120                 125

Gly Val Tyr Pro Leu Ile Tyr Thr Ser Thr Ser Trp Trp Asn Gln Cys
    130                 135                 140

Thr Gly Ser Ser Thr Ala Phe Gly Asn Lys Cys Pro Leu Val Val Ala
145                 150                 155                 160

Arg Tyr Ala Ser Ser Val Gly Ala Leu Pro Ala Gly Trp Gly Phe Gln
                165                 170                 175

Thr Ile Trp Gln Asn Ser Asp Lys Ser Pro Trp Gly Gly Asp Asn Asp
            180                 185                 190

Ile Phe Asn Gly Ser Leu Asp Gln Leu Lys Arg Ile Ala Asn Ala Ser
        195                 200                 205

<210> SEQ ID NO 45
<211> LENGTH: 215
<212> TYPE: PRT
<213> ORGANISM: Hamigera paravellanea

<400> SEQUENCE: 45

Ala Pro Leu Glu Ala Arg Ala Gly Ser Val Gln Gly Phe Asp Ile Ser
1               5                   10                  15

His Tyr Gln Ala Lys Val Asp Phe Ala Ala Ala Tyr Arg Ser Gly Ala
                20                  25                  30

Arg Phe Val Ile Ile Lys Ala Thr Glu Gly Thr Thr Tyr Thr Asp Pro
            35                  40                  45

Ala Phe Ser Ser His Tyr Thr Ser Ala Thr Asn Ala Gly Phe Ile Arg
        50                  55                  60
```

```
Gly Gly Tyr His Phe Ala His Pro Asp Ser Ser Gly Ala Ala Gln
 65                  70                  75                  80

Ala Thr Tyr Phe Leu Ala His Gly Gly Trp Ser Gly Asp Gly Ile
                 85                  90                  95

Thr Leu Pro Gly Met Leu Asp Leu Glu Tyr Asn Pro Ser Gly Ala Thr
            100                 105                 110

Cys Tyr Gly Leu Ser Asp Ala Ala Met Val Ala Trp Ile Gln Asp Phe
            115                 120                 125

Val Asp Thr Tyr His Ala Arg Thr Gly Arg Tyr Pro Met Ile Tyr Thr
130                 135                 140

Thr Ala Asp Trp Trp Asn Thr Cys Thr Gly Asn Ser Ser Lys Phe Ser
145                 150                 155                 160

Gln Thr Cys Pro Leu Val Leu Ala Arg Tyr Ala Ser Ser Val Gly Thr
                165                 170                 175

Val Pro Gly Gly Trp Gly Tyr Gln Thr Ile Trp Gln Asn Ser Asp Ser
            180                 185                 190

Tyr Ala Tyr Gly Gly Asp Ser Asp Ile Phe Asn Gly Asp Glu Thr Gln
            195                 200                 205

Leu Lys Lys Leu Ala Ser Gly
210                 215

<210> SEQ ID NO 46
<211> LENGTH: 217
<212> TYPE: PRT
<213> ORGANISM: Metarhizium iadini

<400> SEQUENCE: 46

Ser Pro Val Glu Leu Glu Gln Arg Ala Ala Ser Val Lys Gly Phe Asp
  1               5                  10                  15

Ile Ser Gly Tyr Gln Pro Asn Val Asp Phe Asn Lys Ala Tyr Ala Asp
                 20                  25                  30

Gly Ala Arg Phe Val Ile Ile Lys Ala Thr Glu Gly Thr Thr Tyr Ile
             35                  40                  45

Asp Lys Thr Phe Ser Lys His Tyr Thr Gly Ala Thr Lys Ala Lys Leu
 50                  55                  60

Ile Arg Gly Ala Tyr His Phe Ala His Pro Gly Gln Asn Lys Ala Ser
 65                  70                  75                  80

Ala Glu Ala Asp Phe Phe Val Gln His Gly Gly Asn Trp Ser Lys Asp
                 85                  90                  95

Ala Ile Thr Leu Pro Gly Met Val Asp Leu Glu Ser Glu Lys Gly His
            100                 105                 110

Pro Pro Cys Trp Gly Leu Ser His Ser Ala Met Val Ala Trp Ile Ser
            115                 120                 125

Glu Phe Val Ala Ala Tyr His Lys Lys Thr Thr Arg Tyr Pro Met Leu
130                 135                 140

Tyr Thr Asn Pro Ser Trp Trp Ser Ala Cys Thr Gly Asn Ser Lys Ala
145                 150                 155                 160

Phe Lys Asp Thr Cys Pro Leu Val Leu Ala Arg Tyr Ala Ser Ser Pro
                165                 170                 175

Gly Ala Ile Pro Gly Gly Trp Pro Ala Gln Thr Ile Trp Gln Asn Ser
            180                 185                 190

Asp Lys Ser Pro Trp Gly Gly Asp Ser Asp Met Phe Asn Gly Asp Leu
            195                 200                 205
```

```
Ala Gln Leu Lys Lys Leu Ala Thr Gly
    210                 215

<210> SEQ ID NO 47
<211> LENGTH: 214
<212> TYPE: PRT
<213> ORGANISM: Thermoascus aurantiacus

<400> SEQUENCE: 47

Glu Leu Asp Lys Arg Ala Arg Gly Val Gln Gly Phe Asp Ile Ser His
1               5                   10                  15

Tyr Gln Pro Asn Val Asp Phe Lys Gly Ala Tyr Asn Ser Gly Ala Arg
            20                  25                  30

Phe Val Ile Ile Lys Ala Thr Glu Gly Thr Thr Tyr Lys Asp Pro Ala
        35                  40                  45

Phe Ser Lys His Tyr Ile Gly Ala Thr Glu Ala Gly Leu Ile Arg Gly
    50                  55                  60

Gly Tyr His Phe Ala His Pro Asp Lys Ser Ser Gly Ala Ala Gln Ala
65                  70                  75                  80

Asn Phe Phe Leu Ala His Gly Gly Trp Ser Gly Asp Gly Ile Thr
                85                  90                  95

Leu Pro Gly Met Val Asp Leu Glu Tyr Asn Pro Ser Gly Asp Ala Cys
            100                 105                 110

Tyr Gly Leu Ser Asp Ser Gln Met Val Ser Trp Ile Arg Asp Phe Val
        115                 120                 125

Asn Thr Tyr His Ala His Thr Gly Arg Tyr Pro Met Ile Tyr Thr Thr
    130                 135                 140

Ala Asp Trp Trp Lys Arg Cys Thr Gly Asp Ser His Ala Phe Ser Thr
145                 150                 155                 160

Thr Cys Pro Leu Val Leu Ala Arg Tyr Asn Ser Ser Pro Gly Thr Val
                165                 170                 175

Pro Gly Gly Trp Pro Tyr His Thr Ile Trp Gln Asn Ser Asp Lys Tyr
            180                 185                 190

Arg Phe Gly Gly Asp Ser Asp Ile Phe Asn Gly Asp Leu Ala Gly Leu
        195                 200                 205

Lys Arg Leu Ala Lys Gly
    210

<210> SEQ ID NO 48
<211> LENGTH: 208
<212> TYPE: PRT
<213> ORGANISM: Clonostachys rossmaniae

<400> SEQUENCE: 48

Ala Val Pro Gly Phe Asp Ile Ser Gly Trp Gln Lys Ser Thr Asp Phe
1               5                   10                  15

Ala Lys Ser Tyr Ala Asn Gly Asp Arg Phe Val Tyr Ile Lys Ala Thr
            20                  25                  30

Glu Gly Thr Thr Phe Lys Asn Pro Leu Phe Ser Lys Gln Tyr Thr Gly
        35                  40                  45

Ala Thr Asn Ala Arg Leu Ile Arg Gly Ala Tyr His Phe Ala Gln Pro
    50                  55                  60

Ala Ser Ser Ser Gly Ala Ser Gln Ala Arg Phe Phe Val Ala Asn Gly
65                  70                  75                  80

Gly Gly Trp Ser Asn Asp Gly Ile Thr Leu Pro Gly Ala Val Asp Met
                85                  90                  95
```

```
Glu Tyr Asn Pro Ser Gly Ala Thr Cys Tyr Gly Leu Ser Lys Thr Ala
                100                 105                 110

Met Val Asn Trp Ile Glu Asp Phe Val Ser Thr Tyr Gln Ala Leu Thr
            115                 120                 125

Gly Arg Trp Pro Val Val Tyr Thr Thr Leu Asp Trp Trp Thr Gln Cys
        130                 135                 140

Thr Gly Asn Ser Ala Lys Phe Gly Asp Arg Cys Pro Leu Trp Val Ala
145                 150                 155                 160

Arg Tyr Ala Ser Ala Val Gly Gln Ile Pro Ala Gly Trp Ser Phe His
                165                 170                 175

Thr Ile Trp Gln Tyr Asn Ala Lys Tyr Pro Glu Gly Gly Asp Ser Asp
            180                 185                 190

Ile Phe Asn Gly Asp Glu Thr Arg Leu Lys Ala Leu Ala Ser Gly Ala
        195                 200                 205
```

<210> SEQ ID NO 49
<211> LENGTH: 203
<212> TYPE: PRT
<213> ORGANISM: Simplicillium obclavatum

<400> SEQUENCE: 49

```
Ala Pro Lys Gly Ile Asp Val Ser His Trp Gln Gly Ser Ile Asn Trp
1               5                   10                  15

Gly Ala Val Lys Ala Asn Gly Ile Glu Trp Ala Tyr Ile Lys Ala Thr
                20                  25                  30

Glu Ser Thr Asn Tyr Lys Asp Pro Asn Phe Asn Ala Asn Tyr Val Gly
            35                  40                  45

Ala Thr Asn Ala Gly Leu Ile Arg Gly Ala Tyr His Phe Ala Arg Pro
        50                  55                  60

Gly Asp Ser Ser Gly Ala Ala Gln Ala Asn Tyr Phe Ala Ser Asn Gly
65                  70                  75                  80

Gly Gly Trp Ser Ala Asp Gly Ile Thr Leu Pro Gly Ala Val Asp Leu
                85                  90                  95

Glu Ala Gly Cys Ser Gly Leu Ser Gln Ser Ala Met Thr Ala Trp Ile
            100                 105                 110

Lys Asp Phe Ser Asn Thr Tyr His Ala Arg Thr Gly Arg Tyr Pro Ala
        115                 120                 125

Ile Tyr Thr Thr Thr Ser Trp Trp Lys Gln Cys Thr Gly Asn Ala Ser
130                 135                 140

Gly Phe Gln Asn Asn Pro Leu Trp Ile Ala Arg Trp Ala Ser Ser
145                 150                 155                 160

Val Gly Glu Leu Pro Ala Gly Tyr Ser Tyr His Thr Phe Trp Gln Tyr
                165                 170                 175

Ala Asp His Gly Pro Asn Pro Gly Asp Gln Asp Val Phe Asn Gly Asp
            180                 185                 190

Ser Ala Gly Leu Lys Arg Met Ala Lys Gly Ser
        195                 200
```

<210> SEQ ID NO 50
<211> LENGTH: 216
<212> TYPE: PRT
<213> ORGANISM: Aspergillus inflatus

<400> SEQUENCE: 50

```
Ala Pro Leu Glu Ala Arg Ala Asn Thr Val Gln Gly Phe Asp Ile Ser
1               5                   10                  15
```

```
Ser Phe Gln Pro Asn Val Asp Phe Ala Ala Ala Tyr Lys Ala Gly Ala
            20                  25                  30

Arg Phe Val Met Met Lys Ala Thr Gln Asn Thr Asn Tyr Val Asp Lys
            35                  40                  45

Thr Phe Asn Ala His Tyr Glu Gly Ala Thr Lys Ala Gly Leu Ile Arg
 50                  55                  60

Gly Gly Tyr His Phe Ala Ile Pro Asn Gly Pro Ser Gly Ala Ala Gln
 65                  70                  75                  80

Ala Glu Tyr Phe Leu Ala His Gly Gly Trp Ser Asp Asp Gly Lys
                85                  90                  95

Thr Leu Pro Gly Met Ile Asp Leu Glu Tyr Asn Pro Tyr Gly Gln Thr
            100                 105                 110

Cys Tyr Asp Leu Ser Ala Ala Lys Met Val Asp Trp Ile Lys Asp Phe
            115                 120                 125

Ser Asn Thr Tyr His Ala Lys Thr Lys Arg Tyr Pro Met Ile Tyr Thr
130                 135                 140

Thr Ala Asn Trp Trp Lys Glu Cys Thr Gly Asp Ser Lys Glu Phe Ser
145                 150                 155                 160

Gln Thr Asn Pro Leu Val Leu Ala Arg Tyr Ser Ser Ala Gly Thr
                165                 170                 175

Val Pro Gly Gly Trp Pro Ala Tyr Ser Phe Trp Gln Asn Ala Asp Lys
            180                 185                 190

Tyr Lys Phe Gly Gly Asp Ser Asp Ile Trp Asn Gly Ser Glu Asp Asn
            195                 200                 205

Leu Lys Lys Phe Ala Lys Gly Ala
            210                 215

<210> SEQ ID NO 51
<211> LENGTH: 207
<212> TYPE: PRT
<213> ORGANISM: Paracremonium inflatum

<400> SEQUENCE: 51

Lys Val Leu Gly Phe Asp Ile Ser His Tyr Gln Ala Thr Val Asp Phe
1               5                   10                  15

Asn Ala Ala Lys Asp Ala Gly Ala Arg Phe Val Ile Ile Lys Ala Thr
            20                  25                  30

Glu Gly Thr Thr Tyr Lys Asp Pro Ala Phe Ser Lys His Tyr Thr Gly
            35                  40                  45

Ala Thr Lys Ala Gly Leu Ile Arg Gly Gly Tyr His Phe Ala Gln Pro
 50                  55                  60

Ala Ser Ser Gly Ala Ala Gln Ala Thr Phe Phe Leu Ala His Gly
 65                  70                  75                  80

Gly Gly Trp Ser Ser Asp Gly Ile Thr Leu Pro Gly Met Leu Asp Leu
            85                  90                  95

Glu Tyr Asn Pro Ser Gly Ser Thr Cys Tyr Gly Leu Ser Gln Ser Ser
            100                 105                 110

Met Val Gln Trp Ile Ser Asp Phe Ile Asp Thr Tyr His Ser Lys Thr
            115                 120                 125

Gly Arg Tyr Pro Leu Ile Tyr Thr Ser Thr Ser Trp Trp Lys Thr Cys
130                 135                 140

Thr Gly Asn Ser Ser Lys Phe Ala Ala Asn Cys Pro Leu Val Val Ala
145                 150                 155                 160
```

Arg Tyr Ser Ser Ser Val Gly Glu Leu Pro Ala Gly Trp Thr Tyr Tyr
            165                 170                 175

Thr Ile Trp Gln Asn Ser Asp Ser Tyr Lys Tyr Gly Gly Asp Ser Asp
            180                 185                 190

Ile Phe Asn Gly Asp Glu Ser Gln Leu Gln Lys Leu Ala Lys Gly
            195                 200                 205

<210> SEQ ID NO 52
<211> LENGTH: 208
<212> TYPE: PRT
<213> ORGANISM: Westerdykella sp

<400> SEQUENCE: 52

Ala Val Ser Gly Met Asp Ile Ser His Tyr Gln Gly Thr Asn Tyr Asn
1               5                   10                  15

Phe Ala Gly Ala Tyr Ser Ser Gly Ala Arg Phe Val Ile Ile Lys Ala
            20                  25                  30

Thr Glu Gly Thr Thr Tyr Thr Asp Pro Gln Phe Ser Ala Asn Tyr Ile
        35                  40                  45

Ala Ala Thr Asn Ala Gly Phe Ile Arg Gly Gly Tyr His Phe Ala Arg
    50                  55                  60

Pro Ala Asp Ser Thr Gly Ala Ala Gln Ala Lys Tyr Phe Val Ser His
65                  70                  75                  80

Gly Gly Gly Trp Ser Ser Asp Gly Ile Thr Leu Pro Gly Met Leu Asp
                85                  90                  95

Leu Glu Tyr Gly Ser Ser Ser Ala Cys His Gly Leu Ser Val Ser Ala
            100                 105                 110

Met Asn Thr Trp Ile Ala Ser Phe Ile Asn Gln Tyr Arg Ser Leu Thr
        115                 120                 125

Gly Ala Tyr Pro Met Ile Tyr Thr Thr Ala Asp Trp Trp Lys Thr Cys
    130                 135                 140

Thr Gly Asp Ser Gln Ala Trp Asn Thr Lys Cys Pro Leu Val Leu Ala
145                 150                 155                 160

Arg Tyr Ser Ser Ser Val Gly Thr Ile Pro Gly Gly Trp Pro Tyr Gln
            165                 170                 175

Thr Ile Trp Gln Phe Asn Asp Ser Tyr Lys Tyr Gly Gly Asp Ser Asp
            180                 185                 190

Thr Phe Asn Gly Asp Leu Ala Gly Leu Lys Arg Leu Ala Lys Gly Ser
            195                 200                 205

<210> SEQ ID NO 53
<211> LENGTH: 207
<212> TYPE: PRT
<213> ORGANISM: Stropharia semiglobata

<400> SEQUENCE: 53

Leu Thr Tyr Ala Val Asp Ser Ser Thr Leu Val Ser Val Ala Thr Tyr
1               5                   10                  15

Thr Lys Ala Lys Ser Gln Gly Phe Thr Lys Ala Ile Ile Arg Gly Tyr
            20                  25                  30

Gln Glu Ala Cys Gly Ser Gly Gly Ala Val Asp Pro Asn Phe Val Gln
        35                  40                  45

Thr Tyr Lys Asn Ala Arg Ala Ala Gly Tyr Thr Asp Ile Asp Met Tyr
    50                  55                  60

Trp Phe Pro Cys Asn Gly Ser Thr His Asn Cys Lys Ser Tyr Ala Thr
65                  70                  75                  80

```
Gln Ile Ala Ala Ile Ala Ala Thr Phe Ser Ala Asn Ser Met Lys Ile
                85                  90                  95

Gly Arg Ile Trp Ile Asp Ile Glu Lys Asp Ala Ala Val Cys Asn Asn
            100                 105                 110

Trp Asn Tyr Gly Thr Ala Gly Asn Leu Ser Gln Ala Lys Ala Leu Ile
        115                 120                 125

Ser Ala Ile Lys Ala Ser Gly Phe Val Tyr Gly Ile Tyr Ser Ser Pro
    130                 135                 140

Gly Glu Trp Gly Asn Ile Phe Gly Ser Thr Ser Val Val Asp Asn
145                 150                 155                 160

Ser Ala Pro Leu Trp Phe Ala Thr Trp Asn Asn Val Gln Thr Leu Thr
                165                 170                 175

Met Gly Thr Lys Phe Gly Gly Trp Thr Ser Ala Met Gly His Gln Tyr
            180                 185                 190

Thr Asp Val Ser Ala Ser Gly Gln Phe Asp Leu Ser Val Phe Ala
        195                 200                 205
```

<210> SEQ ID NO 54
<211> LENGTH: 208
<212> TYPE: PRT
<213> ORGANISM: Gelasinospora cratophora

<400> SEQUENCE: 54

```
Thr Val Gln Gly Phe Asp Ile Ser His Tyr Gln Ser Ser Val Asn Phe
1               5                   10                  15

Ala Gly Ala Tyr Ser Ser Gly Ala Arg Phe Val Ile Ile Lys Ala Thr
            20                  25                  30

Glu Gly Thr Thr Tyr Ile Asp Ser Ser Phe Ser Ser His Tyr Thr Gly
        35                  40                  45

Ala Thr Ser Ala Gly Leu Ile Arg Gly Tyr His Phe Ala His Pro
    50                  55                  60

Asp Ser Ser Thr Gly Ala Ala Gln Ala Asp Tyr Phe Leu Ala His Gly
65                  70                  75                  80

Gly Gly Trp Ser Ala Asp Gly Ile Thr Leu Pro Gly Met Ile Asp Leu
                85                  90                  95

Glu Ser Val Ser Gly Lys Ala Thr Cys Phe Gly Leu Ser Thr Ser Ala
            100                 105                 110

Met Val Ser Trp Ile Lys Ser Phe Ser Asp Arg Tyr Tyr Ala Lys Thr
        115                 120                 125

Gly Arg Tyr Pro Met Ile Tyr Thr Asn Tyr Ser Trp Trp Asn Gln Cys
    130                 135                 140

Thr Gly Asn Ser Ala Ser Phe Ala Ala Thr Asn Pro Leu Val Leu Ala
145                 150                 155                 160

Arg Trp Ser Ser Thr Val Gly Thr Leu Pro Gly Gly Trp Ser Val Gln
                165                 170                 175

Thr Ile Trp Gln Asn Ala Asp Thr Tyr Thr Tyr Gly Gly Asp Ser Asp
            180                 185                 190

Val Phe Asn Gly Ser Leu Asp Arg Leu Lys Ala Leu Ala Lys Gly Ser
        195                 200                 205
```

<210> SEQ ID NO 55
<211> LENGTH: 207
<212> TYPE: PRT
<213> ORGANISM: Flammulina velutipes -continued

<400> SEQUENCE: 55

Arg Leu Asn Gly Ile Asp Val Ser Gly Tyr Gln Pro Asn Val Asn Trp
1               5                  10                  15

Ala Thr Val Lys Ala Asn Gly Val Ser Phe Ala Tyr Ile Lys Ala Thr
            20                  25                  30

Glu Gly Thr Thr Tyr Thr Asn Pro Ser Phe Ser Ser Gln Tyr Thr Gly
        35                  40                  45

Ala Thr Lys Ala Gly Leu Ile Arg Gly Ser Tyr His Phe Ala His Pro
    50                  55                  60

Ser Ser Ser Thr Gly Ala Ala Gln Ala Arg Tyr Phe Val Ala His Gly
65                  70                  75                  80

Gly Gly Trp Ser Gly Asp Gly Ile Thr Leu Pro Gly Ala Leu Asp Ile
                85                  90                  95

Glu Tyr Asn Pro Ser Gly Ala Thr Cys Tyr Gly Leu Ser Thr Ser Ser
            100                 105                 110

Met Val Asn Trp Ile Ala Asp Phe Ser Asn Thr Tyr His Ser Leu Thr
        115                 120                 125

Gly Arg Tyr Pro Val Ile Tyr Thr Thr Ala Asp Trp Trp Arg Thr Cys
    130                 135                 140

Thr Gly Asn Ser Ala Ser Phe Ala Asn Asn Ser Pro Leu Trp Ile Ala
145                 150                 155                 160

Arg Tyr Ala Ser Thr Ile Gly Thr Leu Pro Ala Gly Trp Ser Tyr Ala
                165                 170                 175

Thr Phe Trp Gln Tyr Ala Asp Ser Gly Ser Asn Pro Gly Asp Gln Asp
            180                 185                 190

Tyr Phe Asn Gly Asp Ala Ala Gly Leu Lys Arg Leu Ala Thr Ser
        195                 200                 205

<210> SEQ ID NO 56
<211> LENGTH: 207
<212> TYPE: PRT
<213> ORGANISM: Deconica coprophila

<400> SEQUENCE: 56

Leu Val His Ala Val Asp Ser Ser Leu Val Ser Thr Ala Thr Phe
1               5                  10                  15

Ser Lys Ala Lys Ser Glu Gly Phe Thr Lys Ala Val Ile Arg Gly Tyr
            20                  25                  30

Gln Glu Ala Cys Gly Ser Gly Gly Arg Val Asp Pro Asn Phe Val Gln
        35                  40                  45

Thr Tyr Lys Asn Ala Arg Ala Ala Gly Ile Thr Asn Ile Asp Thr Tyr
    50                  55                  60

Trp Tyr Pro Cys Asn Gly Ser Gly Asn Ser Cys Lys Ser Tyr Ala Lys
65                  70                  75                  80

Gln Ile Ala Gly Ile Ser Ala Thr Phe Asn Ala His Ser Met Lys Ile
                85                  90                  95

Gly Arg Ile Trp Ile Asp Ile Glu Lys Asp Ser Ile Cys Asn Asn Trp
            100                 105                 110

Asn Tyr Gly Thr Ser Gly Asn Arg Asp His Ala Lys Lys Leu Ile Thr
        115                 120                 125

Ala Ile Lys Asn Ser Gly Phe Lys Tyr Gly Ile Tyr Ser Ser Pro Gly
    130                 135                 140

Glu Trp Ser Thr Ile Phe Gly Ser Glu Ser Phe Asp Leu Asp Ser Gly
145                 150                 155                 160

```
Ala Pro Leu Trp Phe Ala Thr Trp Asn Asn Val Gln Thr Leu Thr Leu
            165                 170                 175

Gly Thr His Phe Gly Gly Trp Thr Ser Ala His Gly His Gln Tyr Thr
            180                 185                 190

Asp Lys Ser Ala Ser Gly Gln Phe Asp Leu Asn Val Phe Ser Ser
            195                 200                 205

<210> SEQ ID NO 57
<211> LENGTH: 208
<212> TYPE: PRT
<213> ORGANISM: Rhizomucor pusillus

<400> SEQUENCE: 57

Tyr Glu Thr Gly Val Asp Val Ser Ala Leu Thr Ser Thr Ser Ala Trp
1               5                  10                  15

Ser Cys Ala Lys Lys Leu Gly Tyr Asp His Ala Ile Val Arg Cys Tyr
            20                  25                  30

Ile Glu Ala Tyr Gly Gly Asn Pro Gly Gly Lys Ile Asp Ser Asn Cys
        35                  40                  45

Phe Gln Asn Tyr Lys Asn Ala Lys Ala Gly Gly Phe Thr Ser Val Asp
    50                  55                  60

Ile Tyr Met Phe Pro Cys Thr Gly Arg Ser Thr Cys Lys Ser Pro Ala
65                  70                  75                  80

Ala Gln Val Lys Glu Val Val Asp Tyr Val Gly Ser Asn Lys Met Thr
                85                  90                  95

Val Gly Arg Leu Trp Leu Asp Val Glu Ile Asp Pro Ser Ala Asn Asn
            100                 105                 110

Trp Pro Ser Ala Ser Ser Ala Arg Ser Thr Leu Lys Ser Phe Lys Ser
        115                 120                 125

Ala Leu Asp Ser Thr Gly Trp Lys Tyr Gly Ile Tyr Ser Ser Ala Ser
    130                 135                 140

Gln Trp Ser Gln Ile Thr Gly Ser Ser Ser Trp Glu Leu Asp Ser Ser
145                 150                 155                 160

Leu Pro Leu Trp Tyr Ala His Tyr Asp Ala Ser Leu Ser Phe Ser Asp
                165                 170                 175

Phe Ser Pro Phe Gly Gly Trp Thr Lys Pro Thr Ile Lys Gln Tyr Ala
            180                 185                 190

Gly Ser Val Ser Phe Cys Ser Ala Gly Trp Asp Lys Asn Tyr Tyr Gly
        195                 200                 205

<210> SEQ ID NO 58
<211> LENGTH: 207
<212> TYPE: PRT
<213> ORGANISM: Stropharia semiglobata

<400> SEQUENCE: 58

Leu Val Tyr Gly Val Asp Ser Ser Thr Leu Val Ser Thr Ala Thr Tyr
1               5                  10                  15

Ser Lys Ala Lys Ser Glu Gly Phe Thr Lys Ala Ile Ile Arg Gly Tyr
            20                  25                  30

Gln Glu Ala Cys Gly Ser Gly Arg Val Asp Pro Asn Phe Val Ala
        35                  40                  45

Thr Tyr Lys Asn Ala Arg Ala Ala Gly Ile Thr Asp Ile Asp Met Tyr
    50                  55                  60

Trp Phe Pro Cys Asn Gly Ser Gly Asn Ser Cys Lys Ser Tyr Ala Lys
65                  70                  75                  80
```

```
Gln Leu Ser Glu Ile Ala Asn Val Phe Ser Ala Asn Ser Met Lys Ile
                85                  90                  95

Gly Thr Ile Trp Ile Asp Phe Glu Lys Asp Ser Gly Cys Asn Asn Trp
            100                 105                 110

Asn Tyr Gly Thr Thr Gly Asn Leu Asn His Ala Lys Ala Leu Ile Ser
        115                 120                 125

Ala Ile Lys Ala Thr Gly Phe Lys Phe Gly Ile Tyr Ser Ser Pro Gly
    130                 135                 140

Glu Trp Gly Thr Leu Phe Gly Ser Thr Gly Val Val Leu Asp Ser Ser
145                 150                 155                 160

Ala Pro Leu Trp Phe Ala Thr Trp Asn Asn Val Lys Thr Leu Thr Leu
                165                 170                 175

Gly Thr His Phe Gly Gly Trp Thr Lys Ala Val Gly His Gln Tyr Thr
            180                 185                 190

Asp Val Ser Ala Ser Gly Gln Phe Asp Leu Asn Val Phe Ala Asn
        195                 200                 205

<210> SEQ ID NO 59
<211> LENGTH: 207
<212> TYPE: PRT
<213> ORGANISM: Stropharia semiglobata

<400> SEQUENCE: 59

Leu Val Tyr Gly Val Asp Ser Ser Thr Leu Val Ser Thr Ala Thr Tyr
1               5                   10                  15

Lys Lys Ala Lys Ser Glu Gly Phe Thr Lys Ala Ile Ile Arg Gly Tyr
            20                  25                  30

Gln Glu Ala Cys Gly Ser Gly Gly Arg Val Asp Pro Asn Phe Val Ala
        35                  40                  45

Thr Tyr Lys Asn Ala Arg Ala Ala Gly Ile Thr Asp Ile Asp Met Tyr
    50                  55                  60

Trp Phe Pro Cys Asn Gly Ser Gly Asn Ser Cys Lys Ser Tyr Ala Lys
65                  70                  75                  80

Gln Leu Ser Glu Ile Ala Asn Val Phe Ser Ala Asn Ser Met Lys Ile
                85                  90                  95

Gly Thr Ile Trp Ile Asp Phe Glu Lys Asp Ser Gly Cys Asn Asn Trp
            100                 105                 110

Asn Tyr Gly Thr Thr Gly Asn Leu Asn His Ala Lys Ala Leu Ile Ser
        115                 120                 125

Ala Ile Lys Ala Thr Gly Phe Lys Phe Gly Ile Tyr Ser Ser Pro Gly
    130                 135                 140

Glu Trp Gly Thr Leu Phe Gly Ser Thr Gly Val Val Leu Asp Ser Ser
145                 150                 155                 160

Ala Pro Leu Trp Phe Ala Thr Trp Asn Asn Val Lys Thr Leu Thr Leu
                165                 170                 175

Gly Thr His Phe Gly Gly Trp Thr Thr Ala Ala Gly His Gln Tyr Thr
            180                 185                 190

Asp Val Ser Ser Ser Gly Gln Phe Asp Leu Asn Val Phe Ala Asn
        195                 200                 205

<210> SEQ ID NO 60
<211> LENGTH: 207
<212> TYPE: PRT
<213> ORGANISM: Myceliophthora fergusii
```

<400> SEQUENCE: 60

```
Ala Val Gln Gly Phe Asp Ile Ser His Trp Gln Ser Ser Val Asp Phe
1               5                   10                  15

Lys Ala Ala Tyr Asn Ser Gly Ala Arg Phe Val Ile Ile Lys Ala Thr
            20                  25                  30

Glu Gly Thr Ser Phe Ile Asp Pro Lys Phe Ser Ser His Tyr Thr Gly
        35                  40                  45

Ala Thr Asn Ala Gly Phe Ile Arg Gly Ala Tyr His Phe Ala His Pro
    50                  55                  60

Gly Gln Ser Ser Gly Glu Ala Gln Ala Asp Tyr Phe Leu Ala His Gly
65                  70                  75                  80

Gly Gly Trp Thr Pro Asp Gly Ile Thr Leu Pro Gly Met Leu Asp Leu
                85                  90                  95

Glu Ala Tyr Asn Ala Gly Glu Cys Trp Gly Leu Ser Gln Ser Ala Met
            100                 105                 110

Val Ala Trp Ile Lys Ala Phe Ser Asp Arg Tyr His Ala Arg Thr Gly
        115                 120                 125

Val Tyr Pro Met Leu Tyr Thr Asn Leu Ser Trp Trp Lys Thr Cys Thr
    130                 135                 140

Gly Asn Ser Lys Ala Phe Val Asn Thr Asn Pro Leu Val Leu Ala Arg
145                 150                 155                 160

Trp Ala Ser Ser Pro Gly Glu Ile Pro Gly Trp Pro Trp Gln Thr
                165                 170                 175

Ile Trp Gln Asn Ser Asp Ser Tyr Arg Tyr Gly Gly Asp Ser Asp Ile
            180                 185                 190

Phe Asn Gly Asp Met Asn Gln Leu Arg Arg Leu Ala Thr Ala Ala
            195                 200                 205
```

<210> SEQ ID NO 61
<211> LENGTH: 204
<212> TYPE: PRT
<213> ORGANISM: Mortierella alpina

<400> SEQUENCE: 61

```
Ala Leu Pro Lys Gly Ile Asp Val Ser His Trp Gln Gly Asp Val Asn
1               5                   10                  15

Trp Asn Ser Val Lys Ala Ala Gly Ile Glu Phe Val Tyr Ile Lys Ala
            20                  25                  30

Thr Glu Ser Ile Asn Tyr Ile Asp Ser Lys Phe Asp Ala Asn Tyr Val
        35                  40                  45

Gly Ala Thr Asn Ala Gly Leu Ile Arg Gly Gly Tyr His Phe Ala Arg
    50                  55                  60

Pro Ala Ala Ser Ser Gly Ala Val Gln Ala Asn Tyr Phe Leu Ala Asn
65                  70                  75                  80

Gly Gly Gly Trp Ser Ser Asp Gly Ile Thr Leu Pro Gly Ala Leu Asp
                85                  90                  95

Leu Glu Ala Gly Cys Ser Gly Leu Ser Gln Ala Ala Met Thr Ala Trp
            100                 105                 110

Val Arg Asp Phe Ser Asp Thr Tyr His Ala Arg Thr Gly Arg Tyr Pro
        115                 120                 125

Val Ile Tyr Thr Thr Thr Ser Trp Trp Lys Gln Cys Thr Gly Asn Ala
    130                 135                 140

Ser Gly Phe Gln Asn Asn Asn Pro Leu Trp Ile Ala Arg Trp Ala Ser
145                 150                 155                 160
```

Ser Ala Gly Glu Leu Pro Ala Gly Tyr Ala Phe His Thr Phe Trp Gln
            165                 170                 175

Tyr Ala Asp Lys Gly Pro Asn Pro Gly Asp Gln Asp Tyr Phe Asn Gly
            180                 185                 190

Asp Ser Ala Gly Leu Arg Arg Phe Ala Lys Gly Ser
            195                 200

<210> SEQ ID NO 62
<211> LENGTH: 216
<212> TYPE: PRT
<213> ORGANISM: Penicillium atrovenetum

<400> SEQUENCE: 62

Thr Pro Leu Glu Ser Arg Ala Ser Gly Val Gln Gly Phe Asp Ile Ser
1               5                   10                  15

Ser Tyr Gln Gly Thr Val Asp Phe Ala Gly Ala Tyr Ala Ala Gly Ala
            20                  25                  30

Arg Phe Val Met Ile Lys Ala Thr Glu Gly Thr Thr Tyr Thr Asp Lys
        35                  40                  45

Thr Phe Ser Ser His Tyr Glu Gly Ala Ser Ser Ala Gly Leu Ile Arg
    50                  55                  60

Gly Gly Tyr His Phe Ala His Pro Asp Ser Ser Ser Gly Ala Lys Gln
65                  70                  75                  80

Ala Glu Tyr Phe Leu Ala His Gly Gly Gly Trp Ser Asn Asp Gly Lys
                85                  90                  95

Thr Leu Pro Gly Met Leu Asp Ile Glu Tyr Asn Pro Ser Gly Ala Thr
            100                 105                 110

Cys Tyr Gly Ile Ser Lys Ser Ala Met Val Ala Trp Val Lys Asp Phe
        115                 120                 125

Gly Glu Thr Tyr Lys Gly Lys Thr Gly Arg Tyr Pro Met Ile Tyr Thr
    130                 135                 140

Thr Ala Asp Trp Trp Asn Thr Cys Thr Gly Gly Ser Thr Ala Phe Ser
145                 150                 155                 160

Lys Asp Tyr Pro Leu Val Leu Ala Arg Tyr Ser Ser Ser Val Gly Thr
                165                 170                 175

Ile Pro Gly Gly Trp Pro Tyr Gln Ser Phe Trp Gln Asn Ser Asp Lys
            180                 185                 190

Tyr Thr Tyr Gly Gly Asp Ser Asp Leu Trp Asn Gly Ser Glu Ala Ser
        195                 200                 205

Leu Lys Thr Phe Ala Lys Gly Ala
    210                 215

<210> SEQ ID NO 63
<211> LENGTH: 245
<212> TYPE: PRT
<213> ORGANISM: Trichophaea saccata

<400> SEQUENCE: 63

Tyr Pro Val Lys Thr Asp Leu His Cys Arg Ser Ser Pro Ser Thr Ser
1               5                   10                  15

Ala Ser Ile Val Arg Thr Tyr Ser Gly Thr Glu Val Gln Ile Gln
            20                  25                  30

Cys Gln Thr Thr Gly Thr Ser Val Gln Gly Ser Asn Val Trp Asp Lys
        35                  40                  45

Thr Gln His Gly Cys Tyr Val Ala Asp Tyr Tyr Val Lys Thr Gly His
    50                  55                  60

```
Ser Gly Ile Phe Thr Thr Lys Cys Gly Ser Ser Gly Gly Ser
 65                  70                  75                  80

Cys Lys Pro Pro Ile Asn Ala Ala Thr Val Ala Leu Ile Lys Glu
                 85                  90                  95

Phe Glu Gly Phe Val Pro Lys Pro Ala Pro Asp Pro Ile Gly Leu Pro
             100                 105                 110

Thr Val Gly Tyr Gly His Leu Cys Lys Thr Lys Gly Cys Lys Glu Val
             115                 120                 125

Pro Tyr Ser Phe Pro Leu Thr Gln Glu Thr Ala Thr Lys Leu Leu Gln
130                 135                 140

Ser Asp Ile Lys Thr Phe Thr Ser Cys Val Ser Asn Tyr Val Lys Asp
145                 150                 155                 160

Ser Val Lys Leu Asn Asp Asn Gln Tyr Gly Ala Leu Ala Ser Trp Ala
                165                 170                 175

Phe Asn Val Gly Cys Gly Asn Val Gln Thr Ser Ser Leu Ile Lys Arg
             180                 185                 190

Leu Asn Ala Gly Glu Asn Pro Asn Thr Val Ala Ala Gln Glu Leu Pro
             195                 200                 205

Lys Trp Lys Tyr Ala Gly Gly Lys Val Met Pro Gly Leu Val Arg Arg
210                 215                 220

Arg Asn Ala Glu Val Ala Leu Phe Lys Lys Pro Ser Ser Val Gln Ala
225                 230                 235                 240

His Pro Pro Lys Cys
                245

<210> SEQ ID NO 64
<211> LENGTH: 249
<212> TYPE: PRT
<213> ORGANISM: Chaetomium thermophilum

<400> SEQUENCE: 64

Pro Ala Ser Ala Tyr Ala Ile Thr Gly Asp Asn Val Asn Cys Arg Ser
 1               5                  10                  15

Gly Pro Gly Thr Ser Tyr Ala Val Lys Lys Val Tyr Lys Lys Gly Thr
                 20                  25                  30

Asp Val Lys Ile Ser Cys Gln Thr Thr Gly Thr Asn Ile Asn Gly Asn
             35                  40                  45

Asn Leu Trp Asp Lys Thr Ser Asp Gly Cys Tyr Val Ser Asp Tyr Tyr
 50                  55                  60

Val Lys Thr Gly Ser Asn Gly Tyr Val Thr Ser Lys Cys Ser Ser Ser
 65                  70                  75                  80

Gly Gly Ser Thr Cys Ala Ala Pro Lys Ser Asn Gln Ala Thr Val Asp
                 85                  90                  95

Leu Ile Ala Glu Phe Glu Gly Phe Arg Ala Asn Ile Tyr Thr Asp Ala
             100                 105                 110

Ala Gly Tyr Ala Thr Val Gly Tyr Gly His Lys Cys Gln Lys Ala Lys
             115                 120                 125

Cys Ala Glu Val Lys Tyr Lys Ile Pro Leu Ser Lys Ala Asp Gly Lys
130                 135                 140

Lys Leu Leu Ala Asp Asp Met Arg Ser Phe Glu Val Cys Ile Thr Asn
145                 150                 155                 160

Met Leu Asn Ser Lys Ala Lys Leu Asn Tyr Asn Gln Phe Gly Ala Leu
                165                 170                 175
```

```
Val Ser Trp Ser Phe Asn Val Gly Cys Gly Ala Ala Lys Ser Ser Thr
            180                 185                 190

Leu Ile Lys Arg Leu Asn Asn Gly Glu Asn Val Asn Lys Val Leu Ser
            195                 200                 205

Glu Glu Leu Pro Lys Trp Asn Lys Ala Gly Gly Lys Val Leu Gln Gly
210                 215                 220

Leu Val Arg Arg Ala Ala Glu Val Ala Leu Ala Lys Lys Ser Gly
225                 230                 235                 240

Ser Ser Gln Ala Leu Pro Val Lys Cys
                245

<210> SEQ ID NO 65
<211> LENGTH: 248
<212> TYPE: PRT
<213> ORGANISM: Trichoderma harzianum

<400> SEQUENCE: 65

Tyr Pro Ile Thr Gly Asp Val Val Asn Cys Arg Thr Gly Pro Gly Thr
1               5                   10                  15

Ser Tyr Ala Ile Lys Lys Ser Tyr Lys Lys Asn Gln Asp Ile Ser Ile
            20                  25                  30

Ser Cys Gln Thr Ala Gly Thr Ser Val Asn Gly Asn Ser Ile Trp Asp
        35                  40                  45

Lys Thr Ala Asp Gly Cys Tyr Val Ala Asp Tyr Tyr Val Lys Thr Gly
    50                  55                  60

Ser Ser Gly Tyr Val Thr Lys Lys Cys Thr Ala Ser Ser Gly Gly Gly
65                  70                  75                  80

Ser Ser Ser Ser Tyr Cys Lys Thr Ile Asn Ser Ala Gly Val Asp Leu
                85                  90                  95

Ile Ala Lys Trp Glu Gly Phe Val Ala Ser Pro Lys Pro Asp Pro Ile
            100                 105                 110

Gly Leu Pro Thr Val Gly Tyr Gly His Leu Cys Gln Gln Lys Asn Cys
            115                 120                 125

Arg Glu Val Lys Tyr Lys Phe Pro Leu Thr Lys Thr Thr Ala Lys Glu
130                 135                 140

Leu Leu Leu Asp Asp Leu Pro Lys Tyr Thr Lys Cys Leu Ala Asp Tyr
145                 150                 155                 160

Leu Asn Asp Lys Pro Lys Leu Asn Ala Asn Gln Trp Ala Ala Leu Thr
                165                 170                 175

Ser Trp Val Phe Asn Val Gly Cys Gly Asn Ala Lys Thr Ser Thr Leu
            180                 185                 190

Val Lys Arg Leu Asn Asn Gly Glu Ala Ala Asn Thr Val Ala Ala Glu
            195                 200                 205

Glu Leu Pro Lys Trp Arg Met Ala Gly Gly Lys Val Leu Pro Gly Leu
210                 215                 220

Glu Ala Arg Arg Lys Asp Glu Val Lys Leu Phe Lys Thr Ala Ser Ser
225                 230                 235                 240

Lys Gln Ala Tyr Pro Lys Cys Gln
                245

<210> SEQ ID NO 66
<211> LENGTH: 245
<212> TYPE: PRT
<213> ORGANISM: Trichophaea minuta
```

<400> SEQUENCE: 66

```
Tyr Pro Ala Lys Val Asp Leu Arg Cys Arg Ser Ser Pro Ser Thr Ser
1               5                   10                  15

Ala Ser Val Val Arg Thr Tyr Ser Lys Gly Ser Glu Ile Gln Ile Ser
            20                  25                  30

Cys Gln Thr Thr Gly Thr Ser Val Glu Gly Ser Asn Val Trp Asp Lys
        35                  40                  45

Thr Gln His Gly Cys Tyr Val Ala Asp Tyr Tyr Val Lys Thr Gly His
    50                  55                  60

Ser Gly Ile Phe Thr Thr Lys Cys Gly Ser Ser Gly Gly Gly Ser
65                  70                  75                  80

Cys Lys Pro Pro Ile Asn Ala Ala Thr Val Ala Leu Ile Lys Glu
                85                  90                  95

Phe Glu Gly Phe Val Ala Lys Pro Ala Pro Asp Pro Ile Gly Leu Pro
                100                 105                 110

Thr Val Gly Tyr Gly His Leu Cys Lys Thr Lys Gly Cys Lys Glu Val
            115                 120                 125

Pro Tyr Ser Phe Pro Leu Thr Gln Thr Thr Ala Thr Lys Leu Leu Gln
130                 135                 140

Ser Asp Ile Lys Thr Phe Thr Ser Cys Val Ser Asn Tyr Val Lys Asp
145                 150                 155                 160

Ser Val Lys Leu Asn Asp Asn Gln Phe Gly Ala Leu Ser Ser Trp Ala
                165                 170                 175

Phe Asn Val Gly Cys Gly Asn Ile Gln Thr Ser Ser Leu Ile Lys Arg
            180                 185                 190

Leu Asn Ala Gly Glu Asn Pro Asn Thr Val Ala Ala Gln Glu Leu Pro
        195                 200                 205

Lys Trp Lys Tyr Ala Gly Gly Lys Val Leu Pro Gly Leu Val Arg Arg
    210                 215                 220

Arg Lys Ala Glu Val Ala Leu Phe Lys Lys Pro Ser Ser Val Gln Ala
225                 230                 235                 240

His Pro Pro Lys Cys
                245
```

<210> SEQ ID NO 67
<211> LENGTH: 249
<212> TYPE: PRT
<213> ORGANISM: Chaetomium sp. ZY287

<400> SEQUENCE: 67

```
Tyr Lys Ile Ser Gly Ser Ser Val Asn Cys Arg Ser Gly Pro Gly Thr
1               5                   10                  15

Asn Tyr Pro Val Lys Lys Thr Tyr Ala Asn Gly Asp Glu Val Thr Ile
            20                  25                  30

Ser Cys Gln Thr Thr Gly Thr Asn Val Glu Gly Asn Asn Ile Trp Asp
        35                  40                  45

Lys Thr Gln His Gly Cys Tyr Val Ala Asp Lys Tyr Val Lys Thr Gly
    50                  55                  60

Lys Asp Gly Phe Val Thr Lys Lys Cys Gly Ser Ser Gly Gly Gly Gly
65                  70                  75                  80

Gly Gly Lys Thr Cys Lys Ala Pro Lys Ser Asn Ala Ala Thr Val Asp
                85                  90                  95

Leu Ile Ala Ser Phe Glu Gly Phe Arg Ala Asn Ile Tyr Thr Asp Ala
                100                 105                 110
```

-continued

```
Thr Gly His Pro Thr Val Gly Tyr Gly His Met Cys Thr Lys Ser Arg
        115                 120                 125

Cys Ala Glu Val Lys Tyr Lys Ile Pro Leu Ser Lys Ala Asp Gly Lys
    130                 135                 140

Lys Leu Leu Ala Asp Asp Met Ala Lys Phe Glu Lys Cys Ile Lys Glu
145                 150                 155                 160

Met Leu Asn Ser Lys Ala Lys Leu Asn Leu Asn Gln Tyr Gly Ala Leu
                165                 170                 175

Val Ser Trp Ser Phe Asn Val Gly Cys Gly Ala Ala Lys Gly Ser Gln
            180                 185                 190

Leu Val Ser Arg Leu Asn Lys Gly Glu Asn Pro Asn Thr Val Leu Ser
        195                 200                 205

Asn Glu Leu Pro Lys Trp Val His Gly Asn Gly Lys Val Leu Pro Gly
    210                 215                 220

Leu Val Arg Arg Arg Asn Ala Glu Ile Ala Leu Ala Lys Lys Ser Gly
225                 230                 235                 240

Ser Gly Ala Ala Leu Pro Val Lys Cys
                245

<210> SEQ ID NO 68
<211> LENGTH: 245
<212> TYPE: PRT
<213> ORGANISM: Mortierella sp. ZY002

<400> SEQUENCE: 68

Tyr Pro Ile Thr Gly Ala Asp Ala Leu His Cys Arg Ser Gly Pro Gly
1               5                   10                  15

Thr Ser Tyr Pro Ile Gln Lys Thr Leu Arg Pro Pro Gln Asp Ile Lys
            20                  25                  30

Ile Gln Cys Gln Glu Pro Gly Thr Val Val Asn Gly Val Ser Leu Trp
        35                  40                  45

Asp Lys Thr Gln Phe Gly Cys Tyr Val Ser Asp Tyr Tyr Val Lys Thr
    50                  55                  60

Gly Thr Gly Asn Tyr Val Ala Pro Arg Cys Asn Ser Gly Gly Ser Ser
65                  70                  75                  80

Ser Ala Cys Thr Gly Leu Asn Asp Ala Gly Ile Asn Leu Ile Lys Glu
                85                  90                  95

Phe Glu Gly Phe Val Pro Arg Pro Ala Pro Asp Pro Ile Gly Leu Pro
            100                 105                 110

Thr Val Gly Tyr Gly His Leu Cys Gln Thr Lys Gly Cys Gly Glu Val
        115                 120                 125

Lys Tyr Ser Phe Pro Leu Thr Thr Ala Thr Ala Thr Ala Leu Leu Lys
    130                 135                 140

Asp Asp Leu Pro Lys Tyr Thr Ser Cys Leu Ala Lys Ala Leu Asn Gly
145                 150                 155                 160

Lys Pro Lys Leu Asn Lys Asn Gln Trp Ala Ala Leu Ala Ser Trp Thr
                165                 170                 175

Phe Asn Val Gly Cys Gly Asn Met Lys Ser Ser Ser Leu Ile Thr Arg
            180                 185                 190

Leu Asn Ala Gly Gln Asn Pro Asn Thr Val Ala Thr Glu Glu Leu Pro
        195                 200                 205

Lys Trp Lys Leu Ala Gly Gly Lys Val Leu Pro Gly Leu Val Arg Arg
    210                 215                 220
```

Arg Ala Ala Glu Val Lys Leu Phe Lys Thr Ala Asn Ser Ser Gln Gly
225                 230                 235                 240

Tyr Pro Lys Cys Ala
                245

<210> SEQ ID NO 69
<211> LENGTH: 247
<212> TYPE: PRT
<213> ORGANISM: Metarhizium sp. XZ2431

<400> SEQUENCE: 69

Tyr Pro Val Ser Ala Asp Ser Leu Asn Cys Arg Ala Glu Pro Asn Thr
1               5                   10                  15

Ser Ser Ala Ile Lys Thr Thr Tyr Lys Lys Gly Glu Asp Val Lys Ile
            20                  25                  30

Ser Cys Gln Thr Glu Gly Pro Ser Ile Asn Gly Asn Thr Ile Trp Asp
        35                  40                  45

Lys Thr Gln Asp Gly Cys Tyr Val Ala Asp Tyr Tyr Val Lys Thr Gly
    50                  55                  60

Ser Ser Gly Tyr Val Thr Gly Lys Cys Gly Ser Ser Pro Pro Ser
65                  70                  75                  80

Gly Ser Gly Phe Cys Lys Thr Val Asn Lys Ala Gly Leu Asp Leu Ile
                85                  90                  95

Thr Lys Trp Glu Gly Phe Val Ser Ser Pro Arg Gly Asp Pro Ile Gly
            100                 105                 110

Leu Pro Thr Val Gly Tyr Gly His Leu Cys Gln Lys Lys Gly Cys Ala
        115                 120                 125

Glu Val Lys Tyr Lys Phe Pro Leu Thr Lys Ala Thr Ala Leu Gln Leu
    130                 135                 140

Leu Asn Asp Asp Leu Pro Lys Tyr Thr Gly Cys Leu Gly Lys Leu Leu
145                 150                 155                 160

Asn Ser Lys Val Lys Leu Asn Asp Asn Gln Trp Ala Ala Leu Thr Ser
                165                 170                 175

Trp Val Phe Asn Val Gly Cys Gly Asn Ala Gln Ser Ser Ser Leu Val
            180                 185                 190

Arg Arg Leu Asn Asn Gly Glu Asn Pro Asn Thr Val Ala Pro Ser Glu
        195                 200                 205

Leu Pro Lys Trp Lys Met Ala Gly Gly Lys Val Leu Glu Gly Leu Val
    210                 215                 220

Lys Arg Arg Ala Asp Glu Val Arg Leu Phe Lys Val Ser Ser Ser Lys
225                 230                 235                 240

Gly Ala Phe Pro Lys Cys Gln
                245

<210> SEQ ID NO 70
<211> LENGTH: 250
<212> TYPE: PRT
<213> ORGANISM: Geomyces auratus

<400> SEQUENCE: 70

Ala Phe Pro Ile Thr Gly Ser Thr Val Asn Cys Arg Thr Gly Pro Gly
1               5                   10                  15

Thr Ser His Gly Val Lys Thr Ser Tyr Lys Lys Gly His Glu Val Thr
            20                  25                  30

Val Ser Cys Gln Thr Gly Gly Thr Ser Val Asn Gly Asn Ser Ile Trp
        35                  40                  45

```
Asp Lys Thr Ser Asp Gly Cys Tyr Val Ala Asp Tyr Tyr Lys Thr
    50                  55                  60

Gly Ser Ser Gly Tyr Val Lys Pro Lys Cys Gly Ser Ser Ser Gly Gly
65                  70                  75                  80

Gly Gly Gly Ser Ser Cys Gly Ala Pro Lys Ser Asn Ala Ala Thr Val
                85                  90                  95

Asn Leu Ile Ala Glu Phe Glu Gly Phe Val Ser His Val Tyr Thr Asp
            100                 105                 110

Ala Thr Gly His Pro Thr Val Gly Tyr Gly His Leu Cys Ser Asn Ser
        115                 120                 125

Lys Cys Ser Gly Ile Gly Tyr Ser Ile Pro Ile Ser Lys Ala Asn Ala
    130                 135                 140

Lys Lys Leu Leu Ala Lys Asp Met Ala Ile Ala Glu Lys Cys Ile Thr
145                 150                 155                 160

Ala Met Ile Asn Lys Ser Arg Thr Leu Asn Leu Asn Gln Tyr Gly Ala
                165                 170                 175

Leu Val Ser Trp Ala Phe Asn Glu Gly Cys Gly Ala Ala Lys Ser Ser
            180                 185                 190

Thr Leu Ile Lys Arg Ile Asn Asn Gly Glu Lys Pro Ser Thr Val Ile
        195                 200                 205

Pro Gln Glu Leu Pro Lys Trp Val Tyr Gly Gly Ser Ser Val Leu Pro
    210                 215                 220

Gly Leu Val Arg Arg Asn Ala Glu Ile Ala Leu Ala Lys Lys Ala
225                 230                 235                 240

Thr Ser Ser Lys Ala Leu Pro Ala His Cys
                245                 250

<210> SEQ ID NO 71
<211> LENGTH: 240
<212> TYPE: PRT
<213> ORGANISM: Ilyonectria rufa

<400> SEQUENCE: 71

Tyr Lys Ile Thr Gly Asp Asn Val Asn Cys Arg Ser Gly Pro Gly Thr
1               5                   10                  15

Ser Tyr Ser Val Lys Arg Ser Phe Lys Lys Gly Thr Asp Val Thr Leu
            20                  25                  30

Ser Cys Gln Thr Thr Gly Glu Asn Val Leu Gly Thr Ser Ile Trp Asp
        35                  40                  45

Lys Thr Ser Tyr Gly Cys Tyr Val Ser Asp Tyr Tyr Val Lys Thr Gly
    50                  55                  60

Ser Ser Gly Phe Val Val Lys Lys Cys Gly Thr Cys Gly Ala Pro Lys
65                  70                  75                  80

Ser Asn Ala Ala Thr Val Asn Leu Ile Ser Asp Phe Glu Gly Phe Arg
                85                  90                  95

Ala Asn Ile Tyr Lys Asp Ala Ala Gly Tyr Pro Thr Val Gly Tyr Gly
            100                 105                 110

His Leu Cys Ser Asn Ser Arg Cys Thr Asp Val Pro Tyr Ser Ile Pro
        115                 120                 125

Leu Ser Lys Ala Asn Gly Lys Asn Leu Leu Ala Thr Asp Met Thr Lys
    130                 135                 140

Phe Glu Lys Cys Ile Thr Ala Met Val Ser Ser Ser Val Thr Leu Asn
145                 150                 155                 160
```

```
Lys Asn Gln Tyr Gly Ala Leu Val Ser Trp Ala Phe Asn Met Gly Cys
            165                 170                 175

Gly Ala Thr Lys Thr Ser Thr Leu Ile Lys Arg Leu Asn Gln Gly Gln
            180                 185                 190

Asn Val Asn Thr Val Leu Ser Thr Glu Leu Pro Lys Trp Val Tyr Ala
        195                 200                 205

Gly Gly Lys Lys Leu Asn Gly Leu Val Arg Arg Asn Ala Glu Ile
        210                 215                 220

Ala Leu Ala Lys Lys Thr Thr Glu Lys Ala Leu Pro Asn Lys Cys
225                 230                 235                 240
```